(12) United States Patent
Pfeifer et al.

(10) Patent No.: US 6,596,488 B2
(45) Date of Patent: Jul. 22, 2003

(54) TUMOR SUPPRESSOR GENE

(75) Inventors: Gerd P. Pfeifer, Bradbury, CA (US); Reinhard Dammann, Duarte, CA (US)

(73) Assignee: City of Hope, Duarte, CA (US)

( * ) Notice: Subject to any disclaimer, the term of this patent is extended or adjusted under 35 U.S.C. 154(b) by 0 days.

(21) Appl. No.: 09/821,803

(22) Filed: Mar. 30, 2001

(65) Prior Publication Data

US 2002/0098530 A1 Jul. 25, 2002

Related U.S. Application Data

(60) Provisional application No. 60/193,268, filed on Mar. 30, 2000.

(51) Int. Cl.$^7$ .................................................. C12Q 1/68
(52) U.S. Cl. .............................. 435/6; 436/64; 536/24.1
(58) Field of Search ................... 435/6, 7.23; 536/23.3, 536/24.1; 530/324

(56) References Cited

PUBLICATIONS

GenBank, Accession No. AF102770, Feb. 21, 2000, (2 pages).
GenBank, Accession No. AF061836, May 9, 1998, (2 pages).
GenBank, Accession No. NM_007182, Sep. 26, 1999, (2 pages).
Baylin, S. B. et al., " Alterations in DNA Methylation: a Fundamental Aspect of Neoplasia", *Adv. Cancer Res.*, 1998, 72: 141–196.
Clark, S. J. et al., "High Sensitivity Mapping of Methylated Cytosines", *Nucleic Acids Res.* 1994, 22: 2990–2997.
Dammann, R. et al., "Epigenetic Inactivation of a RAS Association Domain Family Protein From the Lung Tumour Suppressor Locus 3p21.3" *Nature Genetics* Jul. 2000, 25: 315–319.
Costello, J. F., et al., "Aberrant CpG–Island Methylation has Non–random and Tumour Type–Specific Patterns", *Nature Genet.*, Feb. 2000, 25: 132–138.
Matsumoto, S. et al., "Detailed Deletion Mapping of Chromosome Arm 3p in Breast Cancers: a 2– cM Region on 3p14.3–21.1 and a 5–cM region on 3p24.3–25.1 Commonly Deleted in Tumors", *Genes Chromosomes Cancer,* 1997, 20: 268–274.
Vavvas, D. et al., "Identification of Nore1 as a Potential Ras effector", *J. Biol. Chem.,* Mar. 1998, 273: No. 10 5439–5442.
Whang–Peng, J. et al., "Specific Chromosome Defect Associated with Human Small–Cell Lung Cancer: Deletion 3p(14–23)", *Science* Jan. 1982, 215: 181–182..
Xiong, Z. and Laird, P.W. "Cobra: a Sensitive and Quantitative DNA Methylation Assay", *Nucleic Acids Res.* 1997, 25: No. 12 2532–2534.
GenBank Accession No. AF132675 Jun. 29, 2000, (2 pages).
GenBank Accession No. AF132676 Jun. 29, 2000, (2 pages).
GenBank Accession No. AF132677 Jun. 29, 2000, (2 pages).

*Primary Examiner*—Sheela Huff
*Assistant Examiner*—Yu Misook
(74) *Attorney, Agent, or Firm*—Rothwell, Figg, Ernst & Manbeck, PC

(57) ABSTRACT

The present invention relates generally to the field of human genetics. Specifically, the present invention relates to methods and materials used to isolate and detect a human tumor suppressor gene, termed RASSF1 herein. More specifically, the invention relates to the analysis of the RASSF1 gene and its use in the diagnosis of predisposition to cancer. The invention also relates to the prophylaxis and/or therapy of cancer associated with the RASSF1 gene. The invention further relates to the screening of drugs for cancer therapy. Finally, the invention relates to the screening of the RASSF1 gene for methylation, loss of heterozygosity or mutations, which are useful for diagnosing the predisposition to cancer.

8 Claims, 16 Drawing Sheets

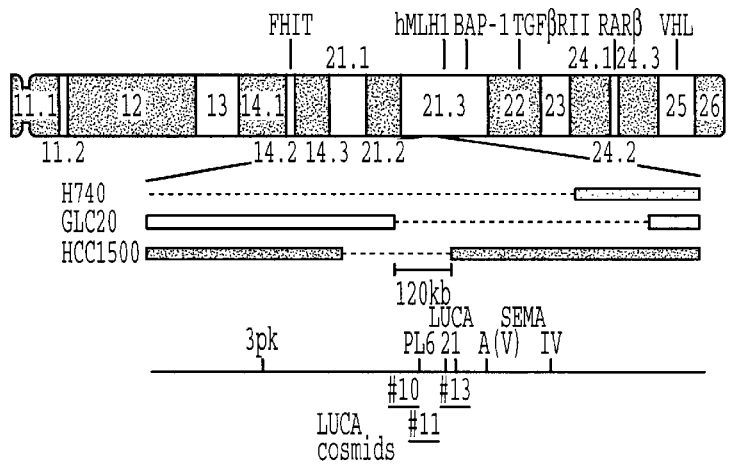

FIG. 1A

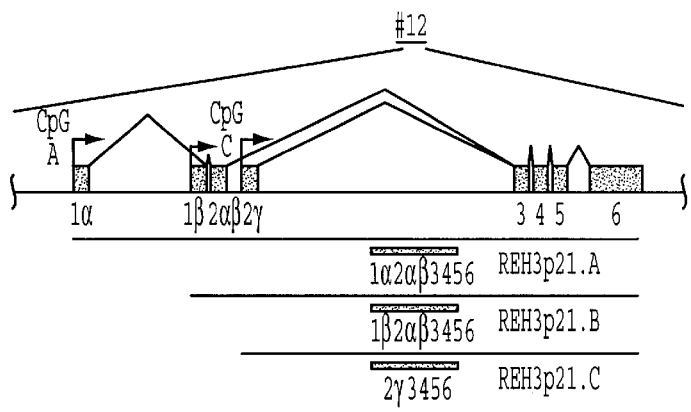

FIG. 1B

```
REH3p21.A    ------------------------------------------------------------------MSGE    4
Norel        MASPAIGQRPYPLLLDPEPPRYLQSLGGTEPPPPARPRRCIPTALIPAAGASEDRGGRRSGRRDPEPTPR   70
Maxp1        MASPAIGQRPYPLLLDPEPPRYLQSLGGTEPPPPARPRRCIPTALISASGASEGRGSRRNARGDPEPTPR   70

REH3p21.A    PELIELRELAPAGRAGKGRTRLERANALRIARGTACNPTRQLVPGRGHRF-QPAGPATHTWCDLCGDFIW   73
Norel        DCRHARPVRPGLQPRLRLRPGSHRPRDVRSIFEQPQDPRVLAERGEGHRFVELALRGGPGWCDLCG---R  137
Maxp1        DCRHARPVRPGLQQRLRRRPGSHRPRDVRSIFEQPQDPRVLAERGEGHRFAELALRGGPGWCDLCG---R  137

REH3p21.C    ----MGEAEAPSFEMTWSSTTSSGYCSQEDSDSELEQYFTARTSLARRPRRDQDEPVEWETPDLSQAEIE   66
REH3p21.A    GVVRKGLOCAHCKFTCHYRCRALVCLDC----CGP----RDLGWEPAVERDTNVDEPVEWETPDLSQAEIE 136
Norel        EVLRQALRCANCKFTCHSECRSLIQLDCRQKGGPALDRRSPGSTLTPTLNQNVCKAVEETQHPPTIQEIK  207
Maxp1        EVLRQALRCANCKFTCHPECRSLIQLDCRQKEGPALDRQSPESTLTPTENKNVCKAVEETQHPPTIQEIK  207

REH3p21.A/C  QKIKEYNAQINSNLFMSLNKDGSYTGFIKVQLKLVRPVSVPSSKKPPSLQDARRGPGRGTSVRRRTSFYL  206/136
Norel        QKIDSYNSREKHCLGMKLSEDGTYTGFIKVHLKLRRPVTVPAGSGPSPSMDAIKEVNPAATTDKRTSFYL  277
Maxp1        QKIDSYNSREKHCLGMKLSEDGTYTGFIKVHLKLRRPVTVPAGIRPQSIYDAIKEVNPAATTDKRTSFYL  277

REH3p21.A/C  PKDAVKHLHVLSRTRAREVIEALLRKFLVVDDPRKFALFERAERHGQVYLRKLLDDEQPLRLRLLAGPSD  276/206
Norel        PLDAIKQLHISSTTTVSEVIQGLLKKFMVVDNPQKFALFKRIHKDGQVLFQKLSIADYPLYLRLLAGPDT  347
Maxp1        PLDAIKQLHISSSTTVSEVIQGLLKKFMVVDNPQKFALFKRIHKDGQVLFQKLSIADCPLYLRLLAGPDT  347

REH3p21.A/C  KALSFVLKENDSGEVNWDAFSMPELHNFLRILQREEEEHLRQILQKYSYCRQKIQEALHACPLG        340/270
Norel        DVLSFVLKENETGEVEWDAFSIPELQNFLTILEKEEQDKIHQLQKKYNKFRQKLEEALRESQGKPG      413
Maxp1        DVLSFVLKENETGDVEWDAFSIPELQNFLTILEKEEQDKIHQLQKKYNKFRQKLEEALRESQGKPG      413
```

FIG. 1C

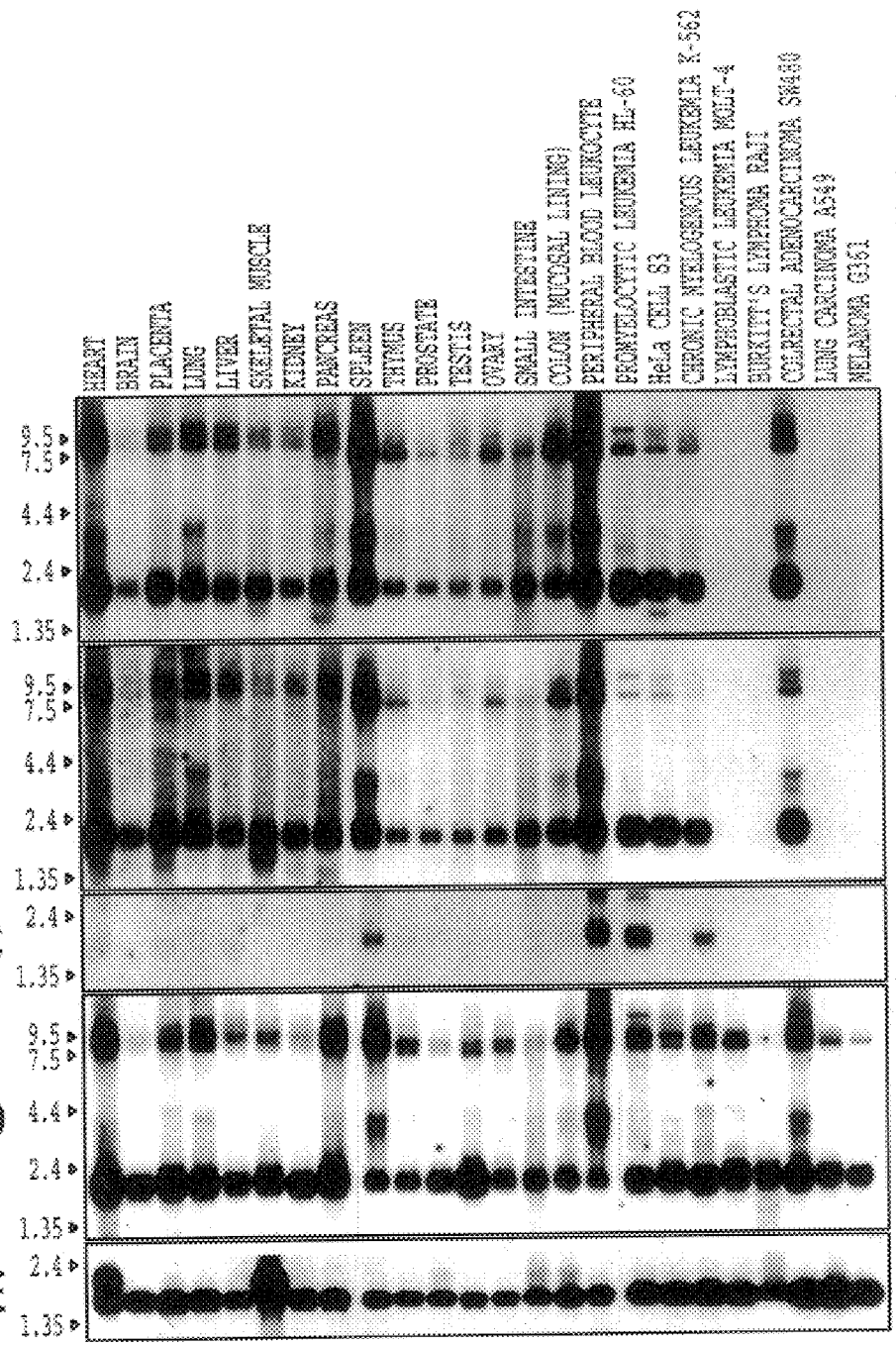

```
primer ML561
CCCCACAGTCCCTGCACCCAGGTTTCCATTGCGCGGCTCTCCTCAGCTCCTTCCCGCCGCCCAGTCTGG
                                1 2                              3 4
                                                Sp1
                                         Sp1
ATCCTGGGGGAGGCGCTGAAGTCGGGGCCGCCCTGTGGCCCGCCCGGCCCGCGCTTGCTAGCGCCCA
           5         6       7          8   9    1011            12

AAGCCAGCGAAGCACGGGCCCAACCGGGCCATGTCGGGGGAGCCTGAGCTCATTGAGCTGCGGGAGC
       13       14          15          16                  primer MU379
```

FIG. 4A

TUMOR SUPPRESSOR GENE

CROSS-REFERENCE TO RELATED APPLICATION

The present application is related to U.S. provisional patent application No. 60/193,268 filed on Mar. 30, 2000, incorporated herein by reference.

This application was made with Government support under Grant No. ES 06070 funded by the National Institutes of Health, Bethesda, Md. The federal government may have certain rights in this invention.

BACKGROUND OF THE INVENTION

The present invention relates generally to the field of human genetics. Specifically, the present invention relates to methods and materials used to isolate and detect a human tumor suppressor gene, termed RASSF1 herein (sometimes also referred to as REH3P21). More specifically, the invention relates to the analysis of the RASSF1 gene and its use in the diagnosis of predisposition to cancer. The invention also relates to the prophylaxis and/or therapy of cancer associated with the RASSF1 gene. The invention further relates to the screening of drugs for cancer therapy. Finally, the invention relates to the screening of the RASSF1 gene for methylation, loss of heterozygosity or mutations, which are useful for diagnosing the predisposition to cancer.

The publications and other materials used herein to illuminate the background of the invention or provide additional details respecting the practice, are incorporated by reference, and for convenience are respectively grouped in the appended Lists of References.

Primary carcinoma of the lung is the leading cause of cancer death in the United States. Every year, more than 100,000 males and 50,000 females develop lung cancer, and most of them die within twelve months. There is a clinical need for a screening test which can detect lung cancer in its earliest stages because prompt treatment of localized disease improves the 5-year survival rate to 30% in males and 50% in females. However, most cases are not detected until local or metastatic growth causes symptoms, and prospective screening with frequent radiography and sputum cytology has not improved the survival rate in smoking males aged 45 years or older. Since early detection of lung cancer can potentially reduce mortality, researchers have investigated alternative diagnostic technologies such as identification of genes for determining risk for developing lung cancer.

Breast cancer is one of the most common malignancies in the world (Hunter, 2000). Only about 7% of breast cancer cases in the United States are thought to be due to the presence of an autosomal dominant susceptibility allele (Black and Weber, 1998). Two familial breast cancer genes (BRCA1 and BRCA2) have been identified (Ford and Easton, 1995). However mutations in these genes are relatively rare in the general population (Peto et al., 1999), and mutations are extremely uncommon in sporadic breast cancers (Futreal et al., 1994; Teng et al., 1996; Lancaster et al., 1996; Miki et al., 1996)). Alterations or changes in expression levels have been described for several other genes, including p53, E-cadherin, and HER-2/neu (Ingvarsson, 1999). It is very likely that additional genes contribute to inherited and sporadic breast cancer.

In general, both alleles of a tumor suppressor gene need to be inactivated by genetic alterations such as chromosomal deletions or loss-of-function mutations in the coding region of a gene (Knudson, 1971). As an alternative mechanism, epigenetic alterations of tumor suppressor genes may occur in human cancers resulting in gene inactivation. Recent studies have demonstrated that the CpG islands in the RB, p16, VHL, APC, and BRCA1 genes are frequently methylated in a variety of human cancers (Baylin et al., 1998; Jones and Laird, 1999; Herman and Baylin, 2000).

CpG islands that are hypermethylated in breast cancer are those of the genes coding for estrogen receptor (Ottaviano et al., 1994; Nass et al., 2000; Yoshida et al., 2000), retinoic acid receptor beta2 (Widschwendter et al., 2000), E-cadherin (Nass et al., 2000; Graff et al., 1995; Graff et al., 2000), BRCA1 (Rice et al., 1998; Catteau et al., 1999; Esteller et al., 2000; Rice et al., 2000), HIC-1 (Fuji e tla., 1998), 14.3.3 sigma (Ferguson et al., 2000), HOXA5 (Raman et al., 2000), and TMS1 (Conway et al., 2000).

Allelic loss at the short arm of chromosome 3 is one of the most common and earliest events in the pathogenesis of lung cancer (Witsuba et al., 2000) and is observed in >90% of small-cell lung cancers (SCLCs) and in 50 to 80% of non-small-cell lung cancers (NSCLCs) (Whang-Peng et al., 1982; Kok et al., 1997). Frequent and early loss of heterozygosity and the presence of homozygous deletions suggest a critical role of the region 3p21.3 in tumorigenesis (Kok et al., 1997; Hung et al., 1995; Wistuba et al., 1999). Loss of heterozygosity (LOH) at 3p21.3 is not limited to lung tumors indicating that this region may harbor a broad-spectrum tumor suppressor gene (Kok et al., 1997). In breast cancer, LOH frequencies have been reported that are in the range of 25-35% using 3p21 markers (Sato et al., 1991; Deng et al., 1994; Matsumoto et al., 1997; Driouch et al., 1998; Braga et al., 1999; Osborne et al., 2000). Frequent loss of heterozygosity and the presence of homozygous deletions suggest a critical role of the region 3p21.3 in tumorigenesis, and recently a region of common homozygous deletion in 3p21.3 was narrowed to 120 kb using several lung cancer and a breast cancer cell line (Sekido et al., 1998). Several putative tumor suppressor genes located at 3p21 have been characterized but none of these genes appears to be significantly altered in lung or breast cancer.

Thus, it is desired to identify a tumor suppressor gene located at chromosme 3p21 which is involved with cancer.

SUMMARY OF THE INVENTION

The present invention relates generally to the field of human genetics. Specifically, the present invention relates to methods and materials used to isolate and detect a human tumor suppressor gene, termed RASSF1 herein. More specifically, the invention relates to the analysis of the RASSF1 gene and its use in the diagnosis of predisposition to cancer. The invention also relates to the prophylaxis and/or therapy of cancer associated with the RASSF1 gene. The invention further relates to the screening of drugs for cancer therapy. Finally, the invention relates to the screening of the RASSF1 gene for methylation, loss of heterozygosity or mutations, which are useful for diagnosing the predisposition to cancer. Examples of cancers include, but are not limited to, lung cancer, breast cancer, kidney cancer, ovarian cancer, head and neck cancer and melanoma.

In one aspect of the invention, novel nucleic acids directed to the RASSF1 gene are provided. The nucleotide sequences and corresponding amino acid sequences are set forth as follows: RASSF1.A-SEQ ID Nos:1 and 2, respectively for nucleotide sequence and amino acid sequence; RASSF1.B-SEQ ID Nos:3 and 4, respectively for nucleotide sequence and amino acid sequence; and RASSF1.C-SEQ ID Nos:5 and 6, respectively for nucleotide sequence and amino acid sequence. Novle nucleic acids which hybridize under stringent hybridization conditions to the nucleic acids RASSF1.A, RASSF1.B and RASSF1.C.

In a second aspect of the invention, a method for detecting a susceptibility in an individual to cancer is provided. Thus, the present invention provides methods for determining whether a subject is at risk for developing cancer. This method relies on the fact that methylation of the RASSF1 gene has been correlated by the inventors with many different kinds of cancer. Mutations in the RASSF1 gene have also been discovered and provide an additional basis for establishing a risk for developing cancer. It will be understood by those of skill in the art, given the disclosure of the invention, that a variety of methods may be utilized to detect mutations in the RASSF1 gene, including the mutations disclosed herein, which are associated with a susceptability to cancer. Similarly, a variety of methods may be utilized to detect the presence of a methylated RASSF1 gene or lack of expression of this gene as a result of such methylation.

The method can include detecting, in a tissue or body fluid of the subject, the presence or absence of methylation of the RASSF1 gene. The detection of the methylation may include the detection of methylation, the detection of an aberrant level of mRNA or the detection of an aberrant level of RASSF1 protein.

The method can include detecting, in a tissue of the subject, the presence or absence of a polymorphism of the RASSF1 gene. The detection of a polymorphism in the RASSF1 gene may include ascertaining the existence of at least one of: a deletion of one or more nucleotides; an addition of one or more nucleotides, a substitution of one or more nucleotides; a gross chromosomal rearrangement; an alteration in the level of a messenger RNA transcript; the presence of a non-wild type splicing pattern of a messenger RNA transcript; a non-wild type level of an RASSF1 protein; and/or an aberrant level of an RASSF1 protein.

For example, detecting the polymorphism can include (i) providing a probe/primer comprised of an oligonucleotide which hybridizes to a sense or antisense sequence of an RASSF1 gene or naturally occurring mutants thereof, or 5' or 3' flanking sequences naturally associated with an RASSF1 gene; (ii) contacting the probe/primer to an appropriate nucleic acid containing sample; and (iii) detecting, by hybridization of the probe/primer to the nucleic acid, the presence or absence of the polymorphism; e.g. wherein detecting the polymorphism comprises utilizing the probe/primer to determine the nucleotide sequence of an RASSF1 gene and, optionally, of the flanking nucleic acid sequences. For instance, the primer can be employed in a polymerase chain reaction (PCR), in a ligase chain reaction (LCR) or other amplification reactions known to a skilled artisan. In alternate embodiments, the level of an RASSF1 protein is detected in an immunoassay using an antibody which is specifically immunoreactive with the RASSF1 protein.

In a third aspect of the invention, compounds that are agonists of a normal (functional) RASSF1 bioactivity and their use in preventing or treating cancer are provided. For example, to ameliorate disease symptoms involving insufficient expression of an RASSF1 gene and/or inadequate amount of functional RASSF1 bioactivity in a subject, a gene therapeutic (comprising a gene encoding a functional RASSF1 protein) or a protein therapeutic (comprising a functional RASSF1 protein) can be administered to the subject. Alternatively, agonists of RASSF1 function, such as small molecule, peptide, or peptidomimetic, or an RASSF1 receptor can be administered.

In fourth aspect of the invention, assays, e.g., for screening test compounds to identify agonists of the biological function of an RASSF1 protein, are provided. The agonists may bind to and activate a protein or nucleic acid that binds to the RASSF1 protein. An exemplary method includes the steps of (i) combining an RASSF1 protein or bioactive fragments thereof and an RASSF1 target molecule (such as an RASSF1 ligand or nucleic acid), e.g., under conditions wherein the RASSF1 protein and its target molecule are able to interact and measuring the biological acitivity of the target molecule; (ii) combining an RASSF1 target molecule and a test compound under conditions wherein the target molecule and the test compound are able to interact and measuring the biological activity of the RASSF1 target molecule; and (iii) comparing the biological activity of the RASSF1 target molecule in (i) and (ii). The test compound is suitable for preventing or treating cancer if it activates the RASSF1 target molecule.

BRIEF DESCRIPTION OF THE FIGURES

FIGS. 1A–1C show the location of genes and deletions in 3p21.3 and amino acid comparison. (A) Physical map of chromosome 3p showing the 3p21.3 LOH region. The location of several genes is indicated. The region of homozygous deletions in small-cell lung cancer cell lines H740 and GLC20 and breast cancer cell line HCC1500 are shown as dashed lines. The positions of six selected genes (3pk, PL6, LUCA 2, LUCA 1, semaphorin A(V) and semaphorin IV) and of four LUCA cosmids are indicated. (B) Map of the RASSF1 gene locus. Black bars indicate exons. Two CpG islands A and C and the transcription initiation areas (arrows) are shown. The three transcripts RASSF1.A, B and C are outlined. (C) Amino acid comparison of RASSF1.A (SEQ ID NO:2), RASSF1.C (SEQ ID NO:6), Nore1 (SEQ ID NO:7) and Maxp1 (SEQ ID NO:8). Identical and similar amino acids are boxed black and gray, respectively.

FIGS. 2A–2E show Northern blot analysis of RASSF1.A, B and C transcripts in various human tissues and cancer cell lines. Northern blots were hybridized with (A) a probe specific for exon $2\alpha\beta$, (B) a probe from exon $1\alpha$, (C) a probe specific for exon $1\beta$, (D) a probe specific for exon $2\gamma$, and (E) a $\beta$-actin probe was used as a control. The sizes of molecular weight markers are shown on the left in kilobases.

FIGS. 4A–4C show methylation analysis. FIG. 4A: Methylated CpG sequences in the CpG island of RASSF1A are shown. Bisulfite sequencing was used to determine the methylation pattern (black squares) of CpGs in SCLC samples. Mosaic patterns (i.e. methylated sequences flanked by unmethylated ones) were not observed. The CpG sequences are underlined and numbered. Sp1 consensus sequences are boxed. The ATG codon is shown in italics. The sequences of primers used in the PCR reaction are marked by boxes. The sequence in FIG. 4A is set forth in SEQ ID NO:9. FIG. 4B: Sequences of PCR products from bisulfite treated DNA for CpG island A obtained from different normal and cancer samples. Methylated cytosines appear as a G signal in the complementary strand (bold Gs). FIG. 4C: Summary of the methylation data. Data were obtained by sequencing of PCR products from bisulfite-treated DNA. White and black squares represent unmethylated and methylated CpGs, respectively. Their numbers correspond to those in FIG. 4A. Gray squares represent partially methylated CpGs. The 16 small-cell lung cancer cell lines are identical to those shown in FIG. 3B.

FIG. 9A: Sequencing data for two breast cancer cell lines (T47D and ZR75-1) and one primary breast carcinoma (BC11) and its matching normal tissue are shown. Data were obtained by direct sequencing of PCR products from bisulfite-treated DNA or from PCR products subcloned into plasmids. FIG. 9B: Sequences of PCR products from bisulfite-treated DNA of 12 primary breast tumors. The percentage of methylated alleles for the three CpG sites (+/−S.D.) was estimated from the relative peak heights of the G and A peaks.

DETAILED DESCRIPTION OF THE INVENTION

Figure 3A:
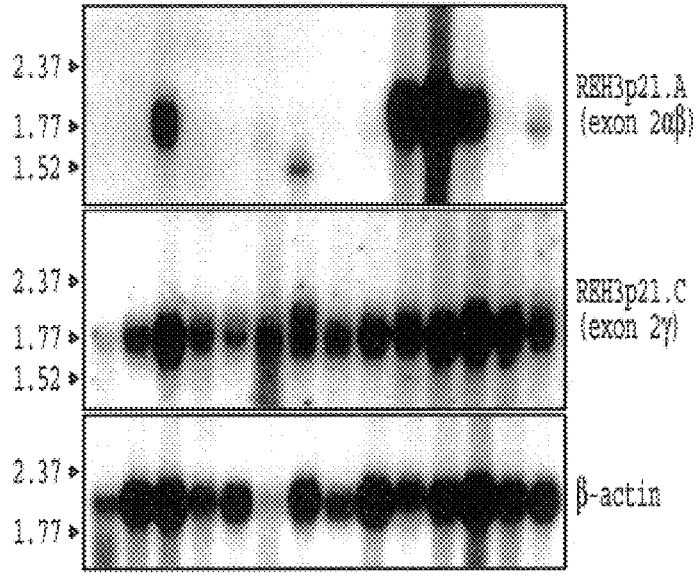
FIGS. 3A and 3B show expression of RASSF1 in various normal and tumor cell lines. (A) Northern blot analysis. Two $\mu$g of poly(A)RNA was separated on a 1% agarose-formaldehyde gel, blotted and hybridized with different probes specific for exon $2\alpha\beta$, exon $2\gamma$, or $\beta$-actin, respectively. The sizes of molecular weight markers are shown on the left in kilobases. B) RT-PCR analysis of RASSF1 expression in small-cell lung cancer cell lines. A 242 bp RT-PCR fragment was visualized using a probe specific for exon $2\alpha\beta$. A 272 bp RT-PCR product was analyzed using a probe specific for exon $2\gamma$. Expression of GAPDH was determined as a control for RNA integrity.

The present invention relates generally to the field of human genetics. Specifically, the present invention relates to methods and materials used to isolate and detect a human tumor suppressor gene, termed RASSF1 herein. More specifically, the invention relates to the analysis of the RASSF1 gene and its use in the diagnosis of predisposition to cancer. The invention also relates to the prophylaxis and/or therapy of cancer associated with the RASSF1 gene. The invention further relates to the screening of drugs for cancer therapy. Finally, the invention relates to the screening of the RASSF1 gene for methylation, loss of heterozygosity or mutations, which are useful for diagnosing the predisposition to cancer.

Here we describe the cloning and characterization of a human Ras effector homologue (REH) located in the 120 kb region of minimal homozygous deletion. Three transcripts A, B and C derived from alternative splicing and promoter usage were identified. In normal tissues the major transcripts A and C were expressed constitutively. Transcript A was missing in all (17/17) small-cell lung cancer cell lines analyzed and in several other cancer cell lines. Loss of expression was correlated with methylation of the CpG island promoter sequence of RASSF1.A. In 24/60 (=40%) primary lung tumors this promoter was also highly methylated and 4/41 primary tumors analyzed carried missense mutations. Re-expression of transcript A in lung carcinoma cells reduced colony formation, suppressed anchorage-independent growth and inhibited tumor formation in nude mice. These characteristics point to the role of RASSF1.A as a tumor suppressor gene in 3p21.3.

According to the diagnostic and prognostic method of the present invention, methylation or lack of expression of the wild-type RASSF1 gene is detected. Alternatively, alteration of the wild-type RASSF1 gene may also be detected. In addition, the method can be performed by detecting the wild-type RASSF1 gene and confirming the lack of a risk factor for cancer. "Alteration of a wild-type gene" encompasses all forms of mutations including deletions, insertions and point mutations in the coding and noncoding regions, particularly those described herein. Deletions may be of the entire gene or of only a portion of the gene. Point mutations may result in stop codons, frameshift mutations or amino acid substitutions. Somatic mutations are those which occur only in certain tissues and are not inherited in the germline. Germline mutations can be found in any of a body's tissues and are inherited. Point mutational events may occur in regulatory regions, such as in the promoter of the gene, leading to loss or diminution of expression of the mRNA. Point mutations may also abolish proper RNA processing, leading to loss of expression of the RASSF1 gene product, or to a decrease in mRNA stability or translation efficiency.

The presence of a risk factor for cancer may be ascertained by testing any tissue of a human for lack of expression or methylation of the RASSF1 gene or for polymorphisms or mutations of the RASSF1 gene. This can be determined by testing DNA from any tissue of the person's body. Most simply, sputum and/or bronchoalveolar lavage fluid can be obtained and DNA extracted from the cells contained therein. Alternatively, blood can be drawn and DNA extracted from the cells of the blood. Alteration of a wild-type RASSF1 allele, whether, for example, by methylation, point mutation or deletion, can be detected by any of the means discussed herein.

One major aspect of the invention is to detect methylation of the RASSF1 gene in sputum and/or bronchoalveolar lavage fluid of smokers to provide an early diagnostic test for those at risk of developing lung cancer. Techniques useful for detecting methylation include, but are not limited to those described by Ahrendt et al. (1999), Belinsky et al. (1998), Clark et al. (1994), Herman et al. (1996) and Xiong, Z. and Laird, P. W. (1997).

The genomic sequencing technique Clark et al., 1994) is capable of detecting every methylated cytosine on both strands of any target sequence, using DNA isolated from fewer than 100 cells. In this method, sodium bisulphite is used to convert cytosine residues to uracil residues in single-stranded DNA, under conditions whereby 5-methylcytosine remains non-reactive. The converted DNA is amplified with specific primers and sequenced. All the cytosine residues remaining in the sequence represent previously methylated cytosines in the genome. This method utilizes defined procedures that maximize the efficiency of denaturation, bisulphite conversion and amplification, to permit methylation mapping of single genes from small amounts of genomic DNA, readily available from germ cells and early developmental stages.

Methylation-specific PCR (MSP; Herman et al., 1996) can rapidly assess the methylation status of virtually any group of CpG sites within a CpG island, independent of the use of methylation-sensitive restriction enzymes. This assay entails initial modification of DNA by sodium bisulfite, converting all unmethylated, but not methylated, cytosines to uracil, and subsequent amplification with primers specific for methylated versus unmethylated DNA. MSP requires only small quantities of DNA, is sensitive to 0.1% methylated alleles of a given CpG island locus, and can be performed on DNA extracted from paraffin-embedded samples. MSP eliminates the false positive results inherent to previous PCR-based approaches which relied on differential restriction enzyme cleavage to distinguish methylated from unmethylated DNA. This method is very simple and can be used on small amounts of tissue or few cells.

The quantitative technique called COBRA (Xiong et al., 1997) can be used to determine DNA methylation levels at specific gene loci in small amounts of genomic DNA. Restriction enzyme digestion is used to reveal methylation-dependent sequence differences in PCR products of sodium bisulfite-treated DNA. Methylation levels in original DNA sample are represented by the relative amounts of digested and undigested PCR product in a linearly quantitative fashion across a wide spectrum of DNA methylation levels. This technique can be reliably applied to DNA obtained from microdissected paraffin-embedded tissue samples. COBRA thus combines the powerful features of ease of use, quantitative accuracy, and compatibility with paraffin sections.

Useful diagnostic techniques for detecting alterations in the wild-type RASSF1 gene include, but are not limited to fluorescent in situ hybridization (FISH), direct DNA sequencing, PFGE analysis, Southern blot analysis, single stranded conformation analysis (SSCA), RNase protection assay, allele-specific oligonucleotide (ASO), dot blot analysis and PCR SSCP, as discussed in detail further below. Also useful are the recently developed techniques of mass spectroscopy (such as MALDI or MALDI-TOF; Fu et al. 1998) and DNA microchip technology for the detection of mutations.

There are several methods that can be used to detect DNA sequence variation. Direct DNA sequencing, either manual sequencing or automated fluorescent sequencing can detect sequence variation. Another approach is the single-stranded conformation polymorphism assay (SSCP) (Orita et al., 1989). This method does not detect all sequence changes, especially if the DNA fragment size is greater than 200 bp, but can be optimized to detect most DNA sequence variation. The reduced detection sensitivity is a disadvantage, but the increased throughput possible with SSCP makes it an attractive, viable alternative to direct sequencing for mutation detection on a research basis. The fragments which have shifted mobility on SSCP gels are then sequenced to determine the exact nature of the DNA sequence variation. Other approaches based on the detection of mismatches between the two complementary DNA strands include clamped denaturing gel electrophoresis (CDGE) (Sheffield et al., 1991), heteroduplex analysis (HA) (White et al., 1992) and chemical mismatch cleavage (CMC) (Grompe et al., 1989). None of the methods described above will detect large deletions, duplications or insertions, nor will they detect a regulatory mutation which affects transcription or translation of the protein. Other methods which might detect these classes of mutations such as a protein truncation assay or the asymmetric assay, detect only specific types of mutations and would not detect missense mutations. A review of currently available methods of detecting DNA sequence variation can be found in a recent review by Grompe (1993). Once a mutation is known, an allele-specific detection approach such as allele-specific oligonucleotide (ASO) hybridization can be utilized to rapidly screen large numbers of other samples for that same mutation. Such a technique can utilize probes which are labeled with gold nanoparticles to yield a visual color result (Elghanian et al., 1997).

A rapid preliminary analysis to detect polymorphisms in DNA sequences can be performed by looking at a series of Southern blots of DNA cut with one or more restriction enzymes, preferably with a large number of restriction enzymes. Each blot contains a series of normal individuals and a series of LQT cases. Southern blots displaying hybridizing fragments (differing in length from control DNA when probed with sequences near or including the RASSF1 locus) indicate a possible mutation. If restriction enzymes which produce very large restriction fragments are used, then pulsed field gel electrophoresis (PFGE) is employed.

Detection of point mutations may be accomplished by molecular cloning of the RASSF1 alleles and sequencing the alleles using techniques well known in the art. Also, the gene or portions of the gene may be amplified, e.g., by PCR or other amplification technique, and the amplified gene or amplified portions of the gene may be sequenced.

There are six well known methods for a more complete, yet still indirect, test for confirming the presence of a susceptibility allele: 1) single-stranded conformation analysis (SSCP) (Orita et al., 1989); 2) denaturing gradient gel electrophoresis (DGGE) (Wartell et al., 1990; Sheffield et al., 1989); 3) RNase protection assays (Finkelstein et al., 1990; Kinszler et al., 1991); 4) allele-specific oligonucleotides (ASOs) (Conner et al., 1983); 5) the use of proteins which recognize nucleotide mismatches, such as the *E. coli* mutS protein (Modrich, 1991); and 6) allele-specific PCR (Ruano and Kidd, 1989). For allele-specific PCR, primers are used which hybridize at their 3' ends to a particular RASSF1 polymorphism or mutation. If the particular polymorphism or mutation is not present, an amplification product is not observed. Amplification Refractory Mutation System (ARMS) can also be used, as disclosed in European Patent Application Publication No. 0332435 and in Newton et al., 1989. Insertions and deletions of genes can also be detected by cloning, sequencing and amplification. In addition, restriction fragment length polymorphism (RFLP) probes for the gene or surrounding marker genes can be used to score alteration of an allele or an insertion in a polymorphic fragment. Such a method is particularly useful for screening relatives of an affected individual for the presence of the mutation found in that individual. Other techniques for detecting insertions and deletions as known in the art can be used.

In the first three methods (SSCP, DGGE and RNase protection assay), a new electrophoretic band appears. SSCP detects a band which migrates differentially because the sequence change causes a difference in single-strand, intramolecular base pairing. RNase protection involves cleavage of the mutant polynucleotide into two or more smaller fragments. DGGE detects differences in migration rates of mutant sequences compared to wild-type sequences, using a denaturing gradient gel. In an allele-specific oligonucleotide assay, an oligonucleotide is designed which detects a specific sequence, and the assay is performed by detecting the presence or absence of a hybridization signal. In the mutS assay, the protein binds only to sequences that contain a nucleotide mismatch in a heteroduplex between mutant and wild-type sequences.

Mismatches, according to the present invention, are hybridized nucleic acid duplexes in which the two strands are not 100% complementary. Lack of total homology may be due to deletions, insertions, inversions or substitutions. Mismatch detection can be used to detect point mutations in the gene or in its mRNA product. While these techniques are less sensitive than sequencing, they are simpler to perform on a large number of samples. An example of a mismatch cleavage technique is the RNase protection method. In the practice of the present invention, the method involves the use of a labeled riboprobe which is complementary to the human wild-type RASSF1 gene coding sequence. The riboprobe and either mRNA or DNA isolated from the person are annealed (hybridized) together and subsequently digested with the enzyme RNase A which is able to detect some mismatches in a duplex RNA structure. If a mismatch is detected by RNase A, it cleaves at the site of the mismatch. Thus, when the annealed RNA preparation is separated on an electrophoretic gel matrix, if a mismatch has been detected and cleaved by RNase A, an RNA product will be seen which is smaller than the full length duplex RNA for the riboprobe and the mRNA or DNA. The riboprobe need not be the fall length of the mRNA or gene but can be a segment of either. If the riboprobe comprises only a segment of the mRNA or gene, it will be desirable to use a number of these probes to screen the whole mRNA sequence for mismatches.

In similar fashion, DNA probes can be used to detect mismatches, through enzymatic or chemical cleavage. See, e.g., Cotton et al., 1988; Shenk et al., 1975; Novack et al., 1986. Alternatively, mismatches can be detected by shifts in the electrophoretic mobility of mismatched duplexes relative to matched duplexes. See, e.g., Cariello, 1988. With either riboprobes or DNA probes, the cellular mRNA or DNA which might contain a mutation can be amplified using PCR (see below) before hybridization. Changes in DNA of the RASSF1 gene can also be detected using Southern blot hybridization, especially if the changes are gross rearrangements, such as deletions and insertions.

DNA sequences of the RASSF1 gene which have been amplified by use of PCR may also be screened using allele-specific probes. These probes are nucleic acid oligomers, each of which contains a region of the gene sequence harboring a known mutation. For example, one oligomer may be about 30 nucleotides in length, corresponding to a portion of the gene sequence. By use of a battery of such allele-specific probes, PCR amplification products can be screened to identify the presence of a previously identified mutation in the gene. Hybridization of allele-specific probes with amplified RASSF1 sequences can be performed, for example, on a nylon filter. Hybridization to a particular probe under high stringency hybridization conditions indicates the presence of the same mutation in the tissue as in the allele-specific probe.

The newly developed technique of nucleic acid analysis via microchip technology is also applicable to the present invention. In this technique, literally thousands of distinct oligonucleotide probes are built up in an array on a silicon chip. Nucleic acid to be analyzed is fluorescently labeled and hybridized to the probes on the chip. It is also possible to study nucleic acid-protein interactions using these nucleic acid microchips. Using this technique one can determine the presence of mutations or even sequence the nucleic acid being analyzed or one can measure expression levels of a gene of interest. The method is one of parallel processing of many, even thousands, of probes at once and can tremendously increase the rate of analysis. Several papers have been published which use this technique. Some of these are Hacia et al., 1996; Shoemaker et al., 1996; Chee et al., 1996; Lockhart et al., 1996; DeRisi et al., 1996; Lipshutz et al., 1995. This method has already been used to screen individuals for mutations in the breast cancer gene BRCA1 (Hacia et al., 1996). This new technology has been reviewed in a news article in *Chemical and Engineering News* (Borman, 1996) and been the subject of an editorial (Editorial, Nature Genetics, 1996). Also see Fodor (1997).

The most definitive test for mutations in a candidate locus is to directly compare genomic RASSF1 sequences from patients with those from a control population. Alternatively, one could sequence messenger RNA after amplification, e.g., by PCR, thereby eliminating the necessity of determining the exon structure of the candidate gene.

Mutations falling outside the coding region of RASSF1 can be detected by examining the non-coding regions, such as introns and regulatory sequences near or within the genes. An early indication that mutations in non-coding regions are important may come from Northern blot experiments that reveal messenger RNA molecules of abnormal size or abundance in patients as compared to those of control individuals.

Alteration of RASSF1 mRNA expression can be detected by any techniques known in the art. These include Northern blot analysis, PCR amplification and RNase protection. Diminished mRNA expression indicates an alteration of the wild-type gene. The alteration may be the result of methylation of the gene or the result of mutations in the gene. Alteration of wild-type genes can also be detected by screening for alteration of wild-type protein or the lack or reduced expression of the protein. For example, monoclonal antibodies immunoreactive with RASSF1 can be used to screen a tissue. Lack of cognate antigen would indicate a mutation or lack of expression of the RASSF1 protein. Antibodies specific for products of mutant alleles could also be used to detect mutant gene product. Such immunological assays can be done in any convenient formats known in the art. These include Western blots, immunohistochemical assays and ELISA assays. Any means for detecting an altered protein can be used to detect alteration of the wild-type RASSF1 gene. Functional assays, such as protein binding determinations, can be used. In addition, assays can be used which detect RASSF1 biochemical function. Finding a mutant RASSF1 gene product indicates alteration of a wild-type RASSF1 gene.

A mutant RASSF1 gene or corresponding gene products can also be detected in other human body samples which contain DNA, such as serum, stool, urine, sputum and bronchoalveolar lavage fluid. The same techniques discussed above for detection of mutant genes or gene products in tissues can be applied to other body samples. By screening such body samples, a simple early diagnosis can be achieved for a risk to developing cancer.

The primer pairs of the present invention are useful for determination of the nucleotide sequence of a particular RASSF1 allele using PCR. The pairs of single-stranded DNA primers can be annealed to sequences within or surrounding the gene in order to prime amplifying DNA synthesis of the gene itself. A complete set of these primers allows synthesis of all of the nucleotides of the gene coding sequences, i.e., the exons. The set of primers preferably allows synthesis of both intron and exon sequences. Allele-specific primers can also be used. Such primers anneal only to particular RASSF1 polymorphic or mutant alleles, and thus will only amplify a product in the presence of the polymorphic or mutant allele as a template.

In order to facilitate subsequent cloning of amplified sequences, primers may have restriction enzyme site sequences appended to their 5' ends. Thus, all nucleotides of the primers are derived from the gene sequence or sequences adjacent the gene, except for the few nucleotides necessary to form a restriction enzyme site. Such enzymes and sites are well known in the art. The primers themselves can be synthesized using techniques which are well known in the art. Generally, the primers can be made using oligonucleotide synthesizing machines which are commerically available. Given the sequence of each gene and polymorphisms described herein, design of particular primers is well within the skill of the art. The present invention adds to this by presenting data on the intron/exon boundaries thereby allowing one to design primers to amplify and sequence all of the exonic regions completely.

The nucleic acid probes provided by the present invention are useful for a number of purposes. They can be used in Southern blot hybridization to genomic DNA and in the RNase protection method for detecting point mutations already discussed above. The probes can be used to detect PCR amplification products. They may also be used to detect mismatches with the RASSF1 gene or mRNA using other techniques.

Definitions

The present invention employs the following definitions, which are, where appropriate, referenced to RASSF1.

"Amplification of Polynucleotides" utilizes methods such as the polymerase chain reaction (PCR), ligation amplification (or ligase chain reaction, LCR) and amplification methods based on the use of Q-beta replicase. Also useful are strand displacement amplification (SDA), thermophilic SDA, and nucleic acid sequence based amplification (3SR or NASBA). These methods are well known and widely practiced in the art. See, e.g., U.S. Pat. Nos. 4,683,195 and 4,683,202 and Innis et al., 1990 (for PCR); Wu and Wallace, 1989 (for LCR); U.S. Pat. Nos. 5,270,184 and 5,455,166 and Walker et al., 1992 (for SDA); Spargo et al., 1996 (for thermophilic SDA) and U.S. Pat. No. 5,409,818, Fahy et al., 1991 and Compton, 1991 for 3SR and NASBA. Reagents and hardware for conducting PCR are commercially available. Primers useful to amplify sequences from the RASSF1 region are preferably complementary to, and hybridize specifically to, sequences in the RASSF1 region or in regions that flank a target region therein. RASSF1 sequences generated by amplification may be sequenced directly. Alternatively, but less desirably, the amplified sequence(s) may be cloned prior to sequence analysis. A method for the direct cloning and sequence analysis of enzymatically amplified genomic segments has been described by Scharf et al., 1986.

"Analyte polynucleotide" and "analyte strand" refer to a single- or double-stranded polynucleotide which is suspected of containing a target sequence, and which may be present in a variety of types of samples, including biological samples.

"Antibodies." The present invention also provides polyclonal and/or monoclonal antibodies and fragments thereof, and immunologic binding equivalents thereof, which are capable of specifically binding to the RASSF1 polypeptide and fragments thereof or to polynucleotide sequences from the RASSF1 region. The term "antibody" is used both to refer to a homogeneous molecular entity, or a mixture such as a serum product made up of a plurality of different molecular entities. Polypeptides may be prepared synthetically in a peptide synthesizer and coupled to a carrier molecule (e.g., keyhole limpet hemocyanin) and injected over several months into rabbits. Rabbit sera is tested for immunoreactivity to the RASSF1 polypeptide or fragment. Monoclonal antibodies may be made by injecting mice with the protein polypeptides, fusion proteins or fragments thereof. Monoclonal antibodies will be screened by ELISA and tested for specific immunoreactivity with RASSF1 polypeptide or fragments thereof. See, Harlow and Lane, 1988. These antibodies will be useful in assays as well as pharmaceuticals.

Once a sufficient quantity of desired polypeptide has been obtained, it may be used for various purposes. A typical use is in the production of antibodies specific for binding. These antibodies may be either polyclonal or monoclonal, and may be produced by in vitro or in vivo techniques well known in the art. For production of polyclonal antibodies, an appropriate target immune system, typically mouse or rabbit, is selected. Substantially purified antigen is presented to the immune system in a fashion determined by methods appropriate for the animal and by other parameters well known to immunologists. Typical sites for injection are in footpads, intramuscularly, intraperitoneally, or intradermally. Of course, other species may be substituted for mouse or rabbit. Polyclonal antibodies are then purified using techniques known in the art, adjusted for the desired specificity.

An immunological response is usually assayed with an immunoassay. Normally, such immunoassays involve some purification of a source of antigen, for example, that produced by the same cells and in the same fashion as the antigen. A variety of immunoassay methods are well known in the art. See, e.g., Harlow and Lane, 1988, or Goding, 1986.

Monoclonal antibodies with affinities of $10^{-8}$ $M^{-1}$ or preferably $10^{-9}$ to $10^{-10}$ $M^{-1}$ or stronger will typically be made by standard procedures as described, e.g., in Harlow and Lane, 1988 or Goding, 1986. Briefly, appropriate animals will be selected and the desired immunization protocol followed. After the appropriate period of time, the spleens of such animals are excised and individual spleen cells fused, typically, to immortalized myeloma cells under appropriate selection conditions. Thereafter, the cells are clonally separated and the supernatants of each clone tested for their production of an appropriate antibody specific for the desired region of the antigen.

Other suitable techniques involve in vitro exposure of lymphocytes to the antigenic polypeptides, or alternatively, to selection of libraries of antibodies in phage or similar vectors. See Huse et al., 1989. The polypeptides and antibodies of the present invention may be used with or without modification. Frequently, polypeptides and antibodies will be labeled by joining, either covalently or non-covalently, a substance which provides for a detectable signal. A wide variety of labels and conjugation techniques are known and are reported extensively in both the scientific and patent literature. Suitable labels include radionuclides, enzymes, substrates, cofactors, inhibitors, fluorescent agents, chemiluminescent agents, magnetic particles and the like. Patents teaching the use of such labels include U.S. Pat. Nos. 3,817,837; 3,850,752; 3,939,350; 3,996,345; 4,277,437; 4,275,149 and 4,366,241. Also, recombinant immunoglobulins may be produced (see U.S. Pat. No. 4,816,567).

"Binding partner" refers to a molecule capable of binding a ligand molecule with high specificity, as for example, an antigen and an antigen-specific antibody or an enzyme and its inhibitor. In general, the specific binding partners must bind with sufficient affinity to immobilize the analyte copy/complementary strand duplex (in the case of polynucleotide hybridization) under the isolation conditions. Specific binding partners are known in the art and include, for example, biotin and avidin or streptavidin, IgG and protein A, the numerous, known receptor-ligand couples, and complementary polynucleotide strands. In the case of complementary polynucleotide binding partners, the partners are normally at least about 15 bases in length, and may be at least 40 bases in length. It is well recognized by those of skill in the art that lengths shorter than 15 (e.g., 8 bases), between 15 and 40, and greater than 40 bases may also be used. The polynucleotides may be composed of DNA, RNA, or synthetic nucleotide analogs. Further binding partners can be identified using, e.g., the two-hybrid yeast screening assay as described herein.

A "biological sample" refers to a sample of tissue or fluid suspected of containing an analyte polynucleotide or polypeptide from an individual including, but not limited to, e.g., plasma, serum, spinal fluid, lymph fluid, the external sections of the skin, respiratory, intestinal, and genitourinary tracts, tears, saliva, blood cells, tumors, organs, tissue and samples of in vitro cell culture constituents.

"Encode". A polynucleotide is said to "encode" a polypeptide if, in its native state or when manipulated by methods well known to those skilled in the art, it can be transcribed and/or translated to produce the mRNA for and/or the polypeptide or a fragment thereof The anti-sense strand is the complement of such a nucleic acid, and the encoding sequence can be deduced therefrom.

"Isolated" or "substantially pure". An "isolated" or "substantially pure" nucleic acid (e.g., an RNA, DNA or a mixed polymer) is one which is substantially separated from other cellular components which naturally accompany a native human sequence or protein, e.g., ribosomes, polymerases, many other human genome sequences and proteins. The term embraces a nucleic acid sequence or protein which has been removed from its naturally occurring environment, and includes recombinant or cloned DNA isolates and chemically synthesized analogs or analogs biologically synthesized by heterologous systems.

"RASSF1Allele" refers, respectively, to normal alleles of the RASSF1 locus as well as alleles of RASSF1 carrying variations that are associated with cancer.

"RASSF1 Locus", "RASSF1 Gene", "RASSF1 Nucleic Acids" or "RASSF1 Polynucleotide" each refer to polynucleotides, all of which are in the RASSF1 region, respectively, that are likely to be expressed in normal tissue, certain alleles of which are associated with a risk factor for smoking and unsuccessful smoking cessation in women. The RASSF1 locus is intended to include coding sequences, intervening sequences and regulatory elements controlling transcription and/or translation. The RASSF1 locus is intended to include all allelic variations of the DNA sequence.

These terms, when applied to a nucleic acid, refer to a nucleic acid which encodes a human RASSF1 polypeptide, fragment, homolog or variant, including, e.g., protein fusions or deletions. The nucleic acids of the present invention will possess a sequence which is either derived from, or substantially similar to a natural RASSF1-encoding gene or one having substantial homology with a natural RASSF1-encoding gene or a portion thereof.

The RASSF1 gene or nucleic acid includes normal alleles of the RASSF1 gene, respectively, including silent alleles having no effect on the amino acid sequence of the RASSF1 polypeptide as well as alleles leading to amino acid sequence variants of the RASSF1 polypeptide that do not substantially affect its function. These terms also include alleles having one or more mutations which adversely affect the function of the RASSF1 polypeptide. A mutation may be a change in the RASSF1 nucleic acid sequence which produces a deleterious change in the amino acid sequence of the RASSF1 polypeptide, resulting in partial or complete loss of RASSF1 function, respectively, or may be a change in the nucleic acid sequence which results in the loss of effective RASSF1 expression or the production of aberrant forms of the RASSF1 polypeptide.

The polynucleotide compositions of this invention include RNA, cDNA, genomic DNA, synthetic forms, and mixed polymers, both sense and antisense strands, and may be chemically or biochemically modified or may contain non-natural or derivatized nucleotide bases, as will be readily appreciated by those skilled in the art. Such modifications include, for example, labels, methylation, substitution of one or more of the naturally-occurring nucleotides with an analog, internucleotide modifications such as uncharged linkages (e.g., methyl phosphonates, phosphotriesters, phosphoramidates, carbamates, etc.), charged linkages (e.g., phosphorothioates, phosphorodithioates, etc.), pendent moieties (e.g., polypeptides), intercalators (e.g., acridine, psoralen, etc.), chelators, alkylators, and modified linkages (e.g., alpha anomeric nucleic acids, etc.). Also included are synthetic molecules that mimic polynucleotides in their ability to bind to a designated sequence via hydrogen bonding and other chemical interactions. Such molecules are known in the art and include, for example, those in which peptide linkages substitute for phosphate linkages in the backbone of the molecule.

The present invention provides recombinant nucleic acids comprising all or part of the RASSF1 region. The recombinant construct may be capable of replicating autonomously in a host cell. Alternatively, the recombinant construct may become integrated into the chromosomal DNA of the host cell. Such a recombinant polynucleotide comprises a polynucleotide of genomic, cDNA, semi-synthetic, or synthetic origin which, by virtue of its origin or manipulation, 1) is not associated with all or a portion of a polynucleotide with which it is associated in nature; 2) is linked to a polynucleotide other than that to which it is linked in nature; or 3) does not occur in nature. Where nucleic acid according to the invention includes RNA, reference to the sequence shown should be construed as reference to the RNA equivalent, with U substituted for T.

Therefore, recombinant nucleic acids comprising sequences otherwise not naturally occurring are provided by this invention. Although the wild-type sequence may be employed, it will often be altered, e.g., by deletion, substitution or insertion. cDNA or genomic libraries of various types may be screened as natural sources of the nucleic acids of the present invention, or such nucleic acids may be provided by amplification of sequences resident in genomic DNA or other natural sources, e.g., by PCR. The choice of cDNA libraries normally corresponds to a tissue source which is abundant in mRNA for the desired proteins. Phage libraries are normally preferred, but other types of libraries may be used. Clones of a library are spread onto plates, transferred to a substrate for screening, denatured and probed for the presence of desired sequences.

The DNA sequences used in this invention will usually comprise at least about five codons (15 nucleotides), more usually at least about 7–15 codons, and most preferably, at least about 35 codons. One or more introns may also be present. This number of nucleotides is usually about the minimal length required for a successful probe that would hybridize specifically with a RASSF1-encoding sequence. In this context, oligomers of as low as 8 nucleotides, more generally 8–17 nucleotides, can be used for probes, especially in connection with chip technology.

Techniques for nucleic acid manipulation are described generally, for example, in Sambrook et al., 1989 or Ausubel et al., 1992. Reagents useful in applying such techniques, such as restriction enzymes and the like, are widely known in the art and commercially available from such vendors as New England BioLabs, Boehringer Mannheim, Amersham, Promega, U.S. Biochemicals, New England Nuclear, and a number of other sources. The recombinant nucleic acid sequences used to produce fusion proteins of the present invention may be derived from natural or synthetic sequences. Many natural gene sequences are obtainable from various cDNA or from genomic libraries using appropriate probes. See, GenBank, National Institutes of Health.

As used herein, a "portion" of the RASSF1 locus or region or allele is defined as having a minimal size of at least about eight nucleotides, or preferably about 15 nucleotides, or more preferably at least about 25 nucleotides, and may have a minimal size of at least about 40 nucleotides. This definition includes all sizes in the range of 8–40 nucleotides as well as greater than 40 nucleotides. Thus, this definition includes nucleic acids of 8, 12, 15, 20, 25, 40, 60, 80, 100, 200, 300, 400, 500 nucleotides, or nucleic acids having any number of nucleotides within these ranges of values (e.g., 9, 10, 11, 16, 23, 30, 38, 50, 72, 121, etc., nucleotides), or nucleic acids having more than 500 nucleotides.

"RASSF1 protein" or "RASSF1 polypeptide" refers to a protein or polypeptide encoded by the RASSF1 locus, variants or fragments thereof. The term "polypeptide" refers to a polymer of amino acids and its equivalent and does not refer to a specific length of the product; thus, peptides, oligopeptides and proteins are included within the definition of a polypeptide. This term also does not refer to, or exclude modifications of the polypeptide, for example, glycosylations, acetylations, phosphorylations, and the like. Included within the definition are, for example, polypeptides containing one or more analogs of an amino acid (including, for example, unnatural amino acids, etc.), polypeptides with substituted linkages as well as other modifications known in the art, both naturally and non-naturally occurring. Ordinarily, such polypeptides will be at least about 50% homologous to the native RASSF1 sequence, preferably in excess of about 90%, and more preferably at least about 95% homologous. Also included are proteins encoded by DNA which hybridize under high or low stringency conditions, to RASSF1-encoding nucleic acids and closely related polypeptides or proteins retrieved by antisera to the RASSF1 protein(s).

The RASSF1 polypeptide may be in isolated and/or purified form, free or substantially free of material with which it is naturally associated. The polypeptide may, if produced by expression in a prokaryotic cell or produced synthetically, lack native post-translational processing, such as glycosylation. Alternatively, the present invention is also directed to polypeptides which are sequence variants, alleles or derivatives of the RASSF1 polypeptide. Such polypeptides may have an amino acid sequence which differs from the wild-type by one or more of addition, substitution, deletion or insertion of one or more amino acids.

"Operably linked" refers to a juxtaposition wherein the components so described are in a relationship permitting them to function in their intended manner. For instance, a promoter is operably linked to a coding sequence if the promoter affects its transcription or expression.

The terms "peptide mimetic" or "mimetic" are intended to refer to a substance which has the essential biological activity of the RASSF1 polypeptide. A peptide mimetic may be a peptide-containing molecule that mimics elements of protein secondary structure (Johnson et al., 1993). The underlying rationale behind the use of peptide mimetics is that the peptide backbone of proteins exists chiefly to orient amino acid side chains in such a way as to facilitate molecular interactions, such as those of antibody and antigen, enzyme and substrate or scaffolding proteins. A peptide mimetic is designed to permit molecular interactions similar to the natural molecule. A mimetic may not be a peptide at all, but it will retain the essential biological activity of natural RASSF1 polypeptide.

"Probes". Polynucleotide polymorphisms associated with RASSF1 alleles which are associated with cancer are detected by hybridization with a polynucleotide probe which forms a stable hybrid with that of the target sequence, under stringent to moderately stringent hybridization and wash conditions. If it is expected that the probes will be perfectly complementary to the target sequence, high stringency conditions will be used. Hybridization stringency may be lessened if some mismatching is expected, for example, if variants are expected with the result that the probe will not be completely complementary. Conditions are chosen which rule out non-specific/adventitious bindings, that is, which minimize noise. (It should be noted that, throughout this disclosure, if it is stated simply that "stringent" conditions are used, that it is meant to be read that "high stringency" conditions are used.) Since such indications identify neutral DNA polymorphisms as well as mutations, these indications need further analysis to demonstrate detection of a RASSF1 susceptibility allele.

Probes for RASSF1 alleles may be derived from the sequences of the RASSF1 region, its cDNA, functionally equivalent sequences, or the complements thereof. The probes may be of any suitable length, which span all or a portion of the RASSF1 region, and which allow specific hybridization to the region. If the target sequence contains a sequence identical to that of the probe, the probes may be short, e.g., in the range of about 8–30 base pairs, since the hybrid will be relatively stable under even stringent conditions. If some degree of mismatch is expected with the probe, i.e., if it is suspected that the probe will hybridize to a variant region, a longer probe may be employed which hybridizes to the target sequence with the requisite specificity.

The probes will include an isolated polynucleotide attached to a label or reporter molecule and may be used to isolate other polynucleotide sequences, having sequence similarity by standard methods. For techniques for preparing and labeling probes see, e.g., Sambrook et al., 1989 or Ausubel et al., 1992. Other similar polynucleotides may be selected by using homologous polynucleotides. Alternatively, polynucleotides encoding these or similar polypeptides may be synthesized or selected by use of the redundancy in the genetic code. Various codon substitutions may be introduced, e.g., by silent changes (thereby producing various restriction sites) or to optimize expression for a particular system. Mutations may be introduced to modify the properties of the polypeptide, perhaps to change the polypeptide degradation or turnover rate.

Probes comprising synthetic oligonucleotides or other polynucleotides of the present invention may be derived from naturally occurring or recombinant single- or double-stranded polynucleotides, or be chemically synthesized. Probes may also be labeled by nick translation, Klenow fill-in reaction, or other methods known in the art.

Portions of the polynucleotide sequence having at least about eight nucleotides, usually at least about 15 nucleotides, and fewer than about 6 kb, usually fewer than about 1.0 kb, from a polynucleotide sequence encoding RASSF1 are preferred as probes. This definition therefore includes probes of sizes 8 nucleotides through 6000 nucleotides. Thus, this definition includes probes of 8, 12, 15, 20, 25, 40, 60, 80, 100, 200, 300, 400 or 500 nucleotides or probes having any number of nucleotides within these ranges of values (e.g., 9, 10, 11, 16, 23, 30, 38, 50, 72, 121, etc., nucleotides), or probes having more than 500 nucleotides. The probes may also be used to determine whether mRNA encoding RASSF1 is present in a cell or tissue. The present invention includes all novel probes having at least 8 nucleotides, its complement or functionally equivalent nucleic acid sequences. The present invention does not include probes which exist in the prior art.

Similar considerations and nucleotide lengths are also applicable to primers which may be used for the amplification of all or part of the RASSF1 gene. Thus, a definition for primers includes primers of 8, 12, 15, 20, 25, 40, 60, 80, 100, 200, 300, 400, 500 nucleotides, or primers having any number of nucleotides within these ranges of values (e.g., 9, 10, 11, 16, 23, 30, 38, 50, 72, 121, etc. nucleotides), or primers having more than 500 nucleotides, or any number of nucleotides between 500 and 6000. The primers may also be used to determine whether mRNA encoding RASSF1 is present in a cell or tissue. The present invention includes all novel primers having at least 8 nucleotides derived from the RASSF1 locus for amplifying the RASSF1 gene, its complement or functionally equivalent nucleic acid sequences. The present invention does not include primers which exist in the prior art. That is, the present invention includes all primers having at least 8 nucleotides with the proviso that it does not include primers existing in the prior art.

"Protein modifications or fragments" are provided by the present invention for RASSF1 polypeptides or fragments thereof which are substantially homologous to primary structural sequence but which include, e.g., in vivo or in vitro chemical and biochemical modifications or which incorporate unusual amino acids. Such modifications include, for example, acetylation, carboxylation, phosphorylation, glycosylation, ubiquitination, labeling, e.g., with radionuclides, and various enzymatic modifications, as will be readily appreciated by those well skilled in the art. A variety of methods for labeling polypeptides and of substituents or labels useful for such purposes are well known in the art, and include radioactive isotopes such as $^{32}P$, ligands which bind to labeled antiligands (e.g., antibodies), fluorophores, chemiluminescent agents, enzymes, and antiligands which can serve as specific binding pair members for a labeled ligand. The choice of label depends on the sensitivity required, ease of conjugation with the primer, stability requirements, and available instrumentation. Methods of labeling polypeptides are well known in the art. See Sambrook et al., 1989 or Ausubel et al., 1992.

Besides substantially full-length polypeptides, the present invention provides for biologically active fragments of the polypeptides. Significant biological activities include ligand-binding, immunological activity and other biological activities characteristic of RASSF1 polypeptides. Immunological activities include both immunogenic function in a target immune system, as well as sharing of immunological epitopes for binding, serving as either a competitor or substitute antigen for an epitope of the RASSF1 protein. As used herein, "epitope" refers to an antigenic determinant of a polypeptide. An epitope could comprise three amino acids in a spatial conformation which is unique to the epitope. Generally, an epitope consists of at least five such amino acids, and more usually consists of at least 8–10 such amino acids. Methods of determining the spatial conformation of such amino acids are known in the art.

For immunological purposes, tandem-repeat polypeptide segments may be used as immunogens, thereby producing highly antigenic proteins. Alternatively, such polypeptides will serve as highly efficient competitors for specific binding. Production of antibodies specific for RASSF1 polypeptides or fragments thereof is described below.

The present invention also provides for fusion polypeptides, comprising RASSF1 polypeptides and fragments. Homologous polypeptides may be fusions between two or more RASSF1 polypeptide sequences or between the sequences of RASSF1 and a related protein. Likewise, heterologous fusions may be constructed which would exhibit a combination of properties or activities of the derivative proteins. For example, ligand-binding or other domains may be "swapped" between different new fusion polypeptides or fragments. Such homologous or heterologous fusion polypeptides may display, for example, altered strength or specificity of binding. Fusion partners include immunoglobulins, bacterial β-galactosidase, trpE, protein A, β-lactamase, alpha amylase, alcohol dehydrogenase and yeast alpha mating factor. See Godowski et al., 1988.

Fusion proteins will typically be made by either recombinant nucleic acid methods, as described below, or may be chemically synthesized. Techniques for the synthesis of polypeptides are described, for example, in Merrifield (1963).

"Protein purification" refers to various methods for the isolation of the RASSF1 polypeptides from other biological material, such as from cells transformed with recombinant nucleic acids encoding RASSF1, and are well known in the art. For example, such polypeptides may be purified by immunoaffinity chromatography employing, e.g., the antibodies provided by the present invention. Various methods of protein purification are well known in the art, and include those described in Deutscher, 1990 and Scopes, 1982.

The terms "isolated", "substantially pure", and "substantially homogeneous" are used interchangeably to describe a protein or polypeptide which has been separated from components which accompany it in its natural state. A monomeric protein is substantially pure when at least about 60 to 75% of a sample exhibits a single polypeptide sequence. A substantially pure protein will typically comprise about 60 to 90% W/W of a protein sample, more usually about 95%, and preferably will be over about 99% pure. Protein purity or homogeneity may be indicated by a number of means well known in the art, such as polyacrylamide gel electrophoresis of a protein sample, followed by visualizing a single polypeptide band upon staining the gel. For certain purposes, higher resolution may be provided by using HPLC or other means well known in the art which are utilized for purification.

A RASSF1 protein is substantially free of naturally associated components when it is separated from the native contaminants which accompany it in its natural state. Thus, a polypeptide which is chemically synthesized or synthesized in a cellular system different from the cell from which it naturally originates will be substantially free from its naturally associated components. A protein may also be rendered substantially free of naturally associated components by isolation, using protein purification techniques well known in the art.

A polypeptide produced as an expression product of an isolated and manipulated genetic sequence is an "isolated polypeptide", as used herein, even if expressed in a homologous cell type. Synthetically made forms or molecules expressed by heterologous cells are inherently isolated molecules.

"Recombinant nucleic acid" is a nucleic acid which is not naturally occurring, or which is made by the artificial combination of two otherwise separated segments of sequence. This artificial combination is often accomplished by either chemical synthesis means, or by the artificial manipulation of isolated segments of nucleic acids, e.g., by genetic engineering techniques. Such is usually done to replace a codon with a redundant codon encoding the same or a conservative amino acid, while typically introducing or removing a sequence recognition site. Alternatively, it is performed to join together nucleic acid segments of desired functions to generate a desired combination of functions.

"Regulatory sequences" refers to those sequences normally within 100 kb of the coding region of a locus, but they may also be more distant from the coding region, which affect the expression of the gene (including transcription of the gene, and translation, splicing, stability or the like of the messenger RNA).

"Substantial homology or similarity". A nucleic acid or fragment thereof is "substantially homologous" ("or substantially similar") to another if, when optimally aligned (with appropriate nucleotide insertions or deletions) with the other nucleic acid (or its complementary strand), there is nucleotide sequence identity in at least about 60% of the nucleotide bases, usually at least about 70%, more usually at least about 80%, preferably at least about 90%, and more preferably at least about 95–98% of the nucleotide bases.

Identity means the degree of sequence relatedness between two polypeptide or two polynucleotides sequences as determined by the identity of the match between two strings of such sequences. Identity can be readily calculated. While there exist a number of methods to measure identity between two polynucleotide or polypeptide sequences, the term "identity" is well known to skilled artisans (Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991). Methods commonly employed to determine identity between two sequences include, but are not limited to those disclosed in *Guide to Huge Computers*, Martin J. Bishop, ed., Academic Press, San Diego, 1994, and Carillo, H., and Lipman, D. (1988). Preferred methods to determine identity are designed to give the largest match between the two sequences tested. Such methods are codified in computer programs. Preferred computer program methods to determine identity between two sequences include, but are not limited to, GCG program package (Devereux et al. (1984), BLASTP, BLASTN, FASTA (Altschul et al. (1990); Altschul et al. (1997)).

As an illustration, by a polynucleotide having a nucleotide sequence having at least, for example, 95% "identity" to a reference nucleotide sequence of, e.g., SEQ ID NO: 1 is intended that the nucleotide sequence of the polynucleotide is identical to the reference sequence except that the polynucleotide sequence may include up to five point mutations per each 100 nucleotides of the reference nucleotide sequence of SEQ ID NO: 1. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5 or 3 terminal positions of the reference nucleotide sequence or anywhere between those terminal positions, interspersed either individually among nucleotides in the reference sequence or in one or more contiguous groups within the reference sequence.

Alternatively, substantial homology or (similarity) exists when a nucleic acid or fragment thereof will hybridize to another nucleic acid (or a complementary strand thereof) under selective hybridization conditions, to a strand, or to its complement. Selectivity of hybridization exists when hybridization which is substantially more selective than total lack of specificity occurs. Typically, selective hybridization will occur when there is at least about 55% homology over a stretch of at least about 14 nucleotides, preferably at least about 65%, more preferably at least about 75%, and most preferably at least about 90%. See, Kanehisa, 1984. The length of homology comparison, as described, may be over longer stretches, and in certain embodiments will often be over a stretch of at least about nine nucleotides, usually at least about 20 nucleotides, more usually at least about 24 nucleotides, typically at least about 28 nucleotides, more typically at least about 32 nucleotides, and preferably at least about 36 or more nucleotides.

Nucleic acid hybridization will be affected by such conditions as salt concentration, temperature, or organic solvents, in addition to the base composition, length of the complementary strands, and the number of nucleotide base mismatches between the hybridizing nucleic acids, as will be readily appreciated by those skilled in the art. Stringent temperature conditions will generally include temperatures in excess of 30° C., typically in excess of 37° C., and preferably in excess of 45° C. Stringent salt conditions will ordinarily be less than 1000 mM, typically less than 500 mM, and preferably less than 200 mM. However, the combination of parameters is much more important than the measure of any single parameter. The stringency conditions are dependent on the length of the nucleic acid and the base composition of the nucleic acid, and can be determined by techniques well known in the art. See, e.g., Wetmur and Davidson, 1968.

Thus, as herein used, the term "stringent conditions" means hybridization will occur only if there is at least 95% and preferably at least 97% identity between the sequences. Such hybridization techniques are well known to those of skill in the art. Stringent hybridization conditions are as defined above or, alternatively, conditions under overnight incubation at 42° C. in a solution comprising: 50% formamide, 5×SSC (150 mM NaCl, 15 mM trisodium citrate), 50 mM sodium phosphate (pH7.6), 5×Denhardt's solution, 10% dextran sulfate, and 20 µg/ml denatured, sheared salmon sperm DNA, followed by washing the filters in 0.1×SSC at about 65° C.

Probe sequences may also hybridize specifically to duplex DNA under certain conditions to form triplex or other higher order DNA complexes. The preparation of such probes and suitable hybridization conditions are well known in the art.

The terms "substantial homology" or "substantial identity", when referring to polypeptides, indicate that the polypeptide or protein in question exhibits at least about 30% identity with an entire naturally-occurring protein or a portion thereof, usually at least about 70% identity, more usually at least about 80% identity, preferably at least about 90% identity, and more preferably at least about 95% identity.

As an illustration, by a polypeptide having an amino acid sequence having at least, for example, 95% "identity" to a reference amino acid sequence of, e.g., SEQ ID NO: 2 is intended that the amino acid sequence of the polypeptide is identical to the reference sequence except that the polypeptide sequence may include up to five amino acid alterations per each 100 amino acids of the reference amino acid of SEQ ID NO: 2. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

Homology, for polypeptides, is typically measured using sequence analysis software. See, e.g., the Sequence Analysis Software Package of the Genetics Computer Group, University of Wisconsin Biotechnology Center, 910 University Avenue, Madison, Wis. 53705. Protein analysis software matches similar sequences using measures of homology assigned to various substitutions, deletions and other modifications. Conservative substitutions typically include substitutions within the following groups: glycine, alanine; valine, isoleucine, leucine; aspartic acid, glutamic acid; asparagine, glutamine; serine, threonine; lysine, arginine, and phenylalanine, tyrosine.

"Substantially similar function" refers to the function of a modified nucleic acid or a modified protein, with reference to the wild-type RASSF1 nucleic acid or wild-type RASSF1 polypeptide. The modified polypeptide will be substantially homologous to the wild-type RASSF1 polypeptide and will have substantially the same function. The modified polypeptide may have an altered amino acid sequence and/or may contain modified amino acids. In addition to the similarity of function, the modified polypeptide may have other useful properties, such as a longer half-life. The similarity of function (activity) of the modified polypeptide may be substantially the same as the activity of the wild-type RASSF1 polypeptide. Alternatively, the similarity of function (activity) of the modified polypeptide may be higher than the activity of the wild-type RASSF1 polypeptide. The modified polypeptide is synthesized using conventional techniques, or is encoded by a modified nucleic acid and produced using conventional techniques. The modified nucleic acid is prepared by conventional techniques. A nucleic acid with a function substantially similar to the wild-type RASSF1 gene function produces the modified protein described above.

A polypeptide "fragment", "portion" or "segment" is a stretch of amino acid residues of at least about five to seven contiguous amino acids, often at least about seven to nine contiguous amino acids, typically at least about nine to 13 contiguous amino acids and, most preferably, at least about 20 to 30 or more contiguous amino acids.

The polypeptides of the present invention, if soluble, may be coupled to a solid-phase support, e.g., nitrocellulose, nylon, column packing materials (e.g., Sepharose beads), magnetic beads, glass wool, plastic, metal, polymer gels, cells, or other substrates. Such supports may take the form, for example, of beads, wells, dipsticks, or membranes.

"Target region" refers to a region of the nucleic acid which is amplified and/or detected. The term "target sequence" refers to a sequence with which a probe or primer will form a stable hybrid under desired conditions.

The practice of the present invention employs, unless otherwise indicated, conventional techniques of chemistry, molecular biology, microbiology, recombinant DNA, genetics, and immunology. See, e.g., Maniatis et al., 1982; Sambrook et al., 1989; Ausubel et al., 1992; Glover, 1985; Anand, 1992; Guthrie and Fink, 1991. A general discussion of techniques and materials for human gene mapping, including mapping of human chromosome 1, is provided, e.g., in White and Lalouel, 1988.

Recombinant or chemically synthesized nucleic acids or vectors, transformation or transfection of host cells, transformed or transfected host cells and polypeptides are produced using conventional techniques, such as described in U.S. Pat. Nos. 5,837,492; 5,800,998 and 5,891,628, each incorporated herein by reference.

The goal of rational drug design is to produce structural analogs of biologically active polypeptides of interest or of small molecules with which they interact (e.g., agonists, antagonists, inhibitors) in order to fashion drugs which are, for example, more active or stable forms of the polypeptide, or which, e.g., enhance or interfere with the function of a polypeptide in vivo. Several approaches for use in rational drug design include analysis of three-dimensional structure, alanine scans, molecular modeling and use of anti-id antibodies. These techniques are well known to those skilled in the art, including those described in U.S. Pat. Nos. 5,837,492; 5,800,998 and 5,891,628, each incorporated herein by reference.

A substance identified as a modulator of polypeptide function may be peptide or non-peptide in nature. Non-peptide "small molecules" are often preferred for many in vivo pharmaceutical uses. Accordingly, a mimetic or mimic of the substance (particularly if a peptide) may be designed for pharmaceutical use.

The designing of mimetics to a known pharmaceutically active compound is a known approach to the development of pharmaceuticals based on a "lead" compound. This approach might be desirable where the active compound is difficult or expensive to synthesize or where it is unsuitable for a particular method of administration, e.g., pure peptides are unsuitable active agents for oral compositions as they tend to be quickly degraded by proteases in the alimentary canal. Mimetic design, synthesis and testing are generally used to avoid randomly screening large numbers of molecules for a target property.

Once the pharmacophore has been found, its structure is modeled according to its physical properties, e.g., stereochemistry, bonding, size and/or charge, using data from a range of sources, e.g., spectroscopic techniques, x-ray diffraction data and NMR. Computational analysis, similarity mapping (which models the charge and/or volume of a pharmacophore, rather than the bonding between atoms) and other techniques can be used in this modeling process. A template molecule is then selected, onto which chemical groups that mimic the pharmacophore can be grafted. The template molecule and the chemical groups grafted thereon can be conveniently selected so that the mimetic is easy to synthesize, is likely to be pharmacologically acceptable, and does not degrade in vivo, while retaining the biological activity of the lead compound. Alternatively, where the mimetic is peptide-based, further stability can be achieved by cyclizing the peptide, increasing its rigidity. The mimetic or mimetics found by this approach can then be screened to see whether they have the target property, or to what extent it is exhibited. Further optimization or modification can then be carried out to arrive at one or more final mimetics for in vivo or clinical testing.

Briefly, a method of screening for a substance which modulates activity of a polypeptide may include contacting one or more test substances with the polypeptide in a suitable reaction medium, testing the activity of the treated polypeptide and comparing that activity with the activity of the polypeptide in comparable reaction medium untreated with the test substance or substances. A difference in activity between the treated and untreated polypeptides is indicative of a modulating effect of the relevant test substance or substances.

Prior to, or as well as being screened for modulation of activity, test substances may be screened for ability to interact with the polypeptide, e.g., in a yeast two-hybrid system (e.g., Bartel et al., 1993; Fields and Song, 1989; Chevray and Nathans, 1992; Lee et al., 1995). This system may be used as a coarse screen prior to testing a substance for actual ability to modulate activity of the polypeptide. Alternatively, the screen could be used to screen test substances for binding to an RASSF1 specific binding partner, or to find mimetics of the RASSF1 protein.

Following identification of a substance which modulates or affects polypeptide activity, the substance may be further investigated. Furthermore, it may be manufactured and/or used in preparation, i.e., a manufacture or formulation, or a composition such as a medicament, pharmaceutical composition or drug. These may be administered to individuals.

In order to detect the presence of a methylated RASSF1 allele or an RASSF1 allele predisposing an individual to cancer, a biological sample such as blood is prepared and analyzed for the presence or absence of methylated or susceptibility alleles of RASSF1. Results of these tests and interpretive information are returned to the health care provider for communication to the tested individual. Such diagnoses may be performed by diagnostic laboratories, or, alternatively, diagnostic kits are manufactured and sold to health care providers or to private individuals for self-diagnosis. Suitable diagnostic techniques include those described herein as well as those described in U.S. Pat. Nos. 5,837,492; 5,800,998 and 5,891,628, each incorporated herein by reference.

Initially for the detection of alterations in the gene sequence, the screening method involves amplification of the relevant RASSF1 sequence. In another preferred embodiment of the invention, the screening method involves a non-PCR based strategy. Such screening methods include two-step label amplification methodologies that are well known in the art. Both PCR and non-PCR based screening strategies can detect target sequences with a high level of sensitivity.

The most popular method used today is target amplification. Here, the target nucleic acid sequence is amplified with polymerases. One particularly preferred method using polymerase-driven amplification is the polymerase chain reaction (PCR). The polymerase chain reaction and other polymerase-driven amplification assays can achieve over a million-fold increase in copy number through the use of polymerase-driven amplification cycles. Once amplified, the resulting nucleic acid can be sequenced or used as a substrate for DNA probes.

When the probes are used to detect the presence of the target sequences the biological sample to be analyzed, such as blood or serum, may be treated, if desired, to extract the nucleic acids. The sample nucleic acid may be prepared in various ways to facilitate detection of the target sequence, e.g. denaturation, restriction digestion, electrophoresis or dot blotting. The targeted region of the analyte nucleic acid usually must be at least partially single-stranded to form hybrids with the targeting sequence of the probe. If the sequence is naturally single-stranded, denaturation will not be required. However, if the sequence is double-stranded, the sequence will probably need to be denatured. Denaturation can be carried out by various techniques known in the art.

Analyte nucleic acid and probe are incubated under conditions which promote stable hybrid formation of the target sequence in the probe with the putative targeted sequence in the analyte. The region of the probes which is used to bind to the analyte can be made completely complementary to the targeted region of RASSF1. Therefore, high stringency conditions are desirable in order to prevent false positives. However, conditions of high stringency are used only if the probes are complementary to regions of the chromosome which are unique in the genome. The stringency of hybridization is determined by a number of factors during hybridization and during the washing procedure, including temperature, ionic strength, base composition, probe length, and concentration of formamide. These factors are outlined in, for example, Maniatis et al., 1982 and Sambrook et al., 1989. Under certain circumstances, the formation of higher order hybrids, such as triplexes, quadraplexes, etc., may be desired to provide the means of detecting target sequences.

Detection of the resulting hybrid, if any, is usually accomplished by the use of labeled probes. Alternatively, the probe may be unlabeled, but may be detectable by specific binding with a ligand which is labeled, either directly or indirectly. Suitable labels, and methods for labeling probes and ligands are known in the art, and include, for example, radioactive labels which may be incorporated by known methods (e.g., nick translation, random priming or kinasing), biotin, fluorescent groups, chemiluminescent groups (e.g., dioxetanes, particularly triggered dioxetanes), enzymes, antibodies, gold nanoparticles and the like. Variations of this basic scheme are known in the art, and include those variations that facilitate separation of the hybrids to be detected from extraneous materials and/or that amplify the signal from the labeled moiety. A number of these variations are reviewed in, e.g., Matthews and Kricka, 1988; Landegren et al., 1988; Mifflin, 1989; U.S. Pat. No. 4,868,105; and in EPO Publication No. 225,807.

As noted above, non-PCR based screening assays are also contemplated in this invention. This procedure hybridizes a nucleic acid probe (or an analog such as a methyl phosphonate backbone replacing the normal phosphodiester), to the low level DNA target. This probe may have an enzyme covalently linked to the probe, such that the covalent linkage does not interfere with the specificity of the hybridization. This enzyme-probe-conjugate-target nucleic acid complex can then be isolated away from the free probe enzyme conjugate and a substrate is added for enzyme detection. Enzymatic activity is observed as a change in color development or luminescent output resulting in a $10^3$–$10^6$ increase in sensitivity. For an example relating to the preparation of oligodeoxynucleotide-alkaline phosphatase conjugates and their use as hybridization probes, see Jablonski et al. (1986).

Two-step label amplification methodologies are known in the art. These assays work on the principle that a small ligand (such as digoxigenin, biotin, or the like) is attached to a nucleic acid probe capable of specifically binding RASSF1. Allele-specific probes are also contemplated within the scope of this example, and exemplary allele-specific probes include probes encompassing the predisposing mutations of this patent application.

In one example, the small ligand attached to the nucleic acid probe is specifically recognized by an antibody-enzyme conjugate. In one embodiment of this example, digoxigenin is attached to the nucleic acid probe. Hybridization is detected by an antibody-alkaline phosphatase conjugate which turns over a chemiluminescent substrate. For methods for labeling nucleic acid probes according to this embodiment see Martin et al., 1990. In a second example, the small ligand is recognized by a second ligand-enzyme conjugate that is capable of specifically complexing to the first ligand. A well known embodiment of this example is the biotin-avidin type of interactions. For methods for labeling nucleic acid probes and their use in biotin-avidin based assays see Rigby et al., 1977 and Nguyen et al., 1992.

The presence of a risk for the development of cancer can also be detected on the basis of the lack of expression of wild-type RASSF1 protein or the alteration of wild-type RASSF1 protein. Such alterations can be determined by sequence analysis in accordance with conventional techniques. More preferably, antibodies (polyclonal or monoclonal) are used to detect differences in, or the absence of RASSF1 peptides. Techniques for raising and purifying antibodies are well known in the art, and any such techniques may be chosen to achieve the preparations claimed in this invention. In a preferred embodiment of the invention, antibodies will immunoprecipitate RASSF1 proteins from solution as well as react with these proteins on Western or immunoblots of polyacrylamide gels. In another preferred embodiment, antibodies will detect RASSF1 proteins in paraffin or frozen tissue sections, using immunocytochemical techniques.

Preferred embodiments relating to methods for detecting RASSF1 or its poly-morphisms/mutations include enzyme linked immunosorbent assays (ELISA), radioimmunoassays (RIA), immunoradiometric assays (IRMA) and immunoenzymatic assays (IEMA), including sandwich assays using monoclonal and/or polyclonal antibodies. Exemplary sandwich assays are described by David et al., in U.S. Pat. Nos. 4,376,110 and 4,486,530, hereby incorporated by reference.

According to the present invention, a method is also provided of supplying wild-type RASSF1 function to a cell which carries a nonfunctioning, missing or mutant RASSF1 allele. Supplying such a function should allow normal functioning of the recipient cells. The wild-type gene or a part of the gene may be introduced into the cell in a vector such that the gene remains extrachromosomal. In such a situation, the gene will be expressed by the cell from the extrachromosomal location. More preferred is the situation where the wild-type gene or a part thereof is introduced into the mutant cell in such a way that it recombines with the endogenous mutant gene present in the cell. Such recombination requires a double recombination event which results in the correction of the gene mutation. Vectors for introduction of genes both for recombination and for extrachromosomal maintenance are known in the art, and any suitable vector may be used. Methods for introducing DNA into cells such as electroporation, calcium phosphate co-precipitation and viral transduction are known in the art, and the choice of method is within the competence of the practitioner. Conventional methods are employed, including those described in U.S. Pat. Nos. 5,837,492; 5,800,998; 5,891,628; and 6,017,524, each incorporated herein by reference.

Alternatively, peptides which have RASSF1 activity can be supplied to cells which carry a nonfunctioning, mutant or missing RASSF1 allele. Protein can be produced by expression of the cDNA sequence in bacteria, for example, using known expression vectors. Alternatively, the polypeptide(s) can be extracted from polypeptide-producing mammalian cells. In addition, the techniques of synthetic chemistry can be employed to synthesize the protein. Any of such techniques can provide the preparation of the present invention which comprises the RASSF1 protein. The preparation is substantially free of other human proteins. This is most readily accomplished by synthesis in a microorganism or in vitro. Active RASSF1 molecules can be introduced into cells by microinjection or by use of liposomes, for example. Alternatively, some active molecules may be taken up by cells, actively or by diffusion. Conventional methods are employed, including those described in U.S. Pat. Nos. 5,837,492; 5,800,998 and 5,891,628, each incorporated herein by reference.

Animals for testing therapeutic agents or for developing animal and cellular models can be selected after mutagenesis of whole animals or after treatment of germline cells or zygotes. Such treatments include insertion of polymorphic/mutant RASSF1 alleles, usually from a second animal species, as well as insertion of disrupted homologous genes. Alternatively, the endogenous RASSF1 gene of the animals may be disrupted by insertion or deletion mutation or other genetic alterations using conventional techniques (Capecchi, 1989; Valancius and Smithies, 1991; Hasty et al., 1991; Shinkai et al., 1992; Mombaerts et al., 1992; Philpott et al., 1992; Snouwaert et al., 1992; Donehower et al., 1992). These transgenic, transplacement and knock-out animals can also be used to screen drugs to be used for the treatment of cancer. Cell lines can also be derived from these animals for use as cellular models, or in drug screening. Conventional methods are employed, including those described in U.S. Pat. Nos. 5,837,492; 5,800,998 and 5,891,628, each incorporated herein by reference.

The identification of the association between the RASSF1 gene and cancer permits the early presymptomatic screening of individuals to identify those at risk for developing cancer. To identify such individuals, the alleles are screened as described herein or using conventional techniques, including but not limited to, one of the following methods: fluorescent in situ hybridization (FISH), direct DNA sequencing, PFGE analysis, Southern blot analysis, single stranded conformation analysis (SSCP), linkage analysis, RNase protection assay, allele-specific oligonucleotide (ASO), dot blot analysis and PCR-SSCP analysis. Also useful is the recently developed technique of DNA microchip technology. Such techniques are described in U.S. Pat. Nos. 5,837,492; 5,800,998 and 5,891,628, each incorporated herein by reference.

Genetic testing will enable practitioners to identify individuals at risk for devloping cancer. Presymptomatic diagnosis will enable better treatment of cancer, including the use of existing medical therapies. Genetic testing will also enable practitioners to identify those individuals, who have been diagnosed with cancer, in whom the diagnosis results from RASSF1.

The RASSF1 polypeptides, antibodies, peptides and nucleic acids of the present invention can be formulated in pharmaceutical compositions, which are prepared according to conventional pharmaceutical compounding techniques. See, for example, *Remington's Pharmaceutical Sciences*, 18th Ed. (1990, Mack Publishing Co., Easton, Pa.). The composition may contain the active agent or pharmaceutically acceptable salts of the active agent. These compositions may comprise, in addition to one of the active substances, a pharmaceutically acceptable excipient, carrier, buffer, stabilizer or other materials well known in the art. Such materials should be non-toxic and should not interfere with the efficacy of the active ingredient. The carrier may take a wide variety of forms depending on the form of preparation desired for administration, e.g., intravenous, oral, intrathecal, epineural or parenteral.

For oral administration, the compounds can be formulated into solid or liquid preparations such as capsules, pills, tablets, lozenges, melts, powders, suspensions or emulsions. In preparing the compositions in oral dosage form, any of the usual pharmaceutical media may be employed, such as, for example, water, glycols, oils, alcohols, flavoring agents, preservatives, coloring agents, suspending agents, and the like in the case of oral liquid preparations (such as, for example, suspensions, elixirs and solutions); or carriers such as starches, sugars, diluents, granulating agents, lubricants, binders, disintegrating agents and the like in the case of oral solid preparations (such as, for example, powders, capsules and tablets). Because of their ease in administration, tablets and capsules represent the most advantageous oral dosage unit form, in which case solid pharmaceutical carriers are obviously employed. If desired, tablets may be sugar-coated or enteric-coated by standard techniques. The active agent can be encapsulated to make it stable to passage through the gastrointestinal tract while at the same time allowing for passage across the blood brain barrier. See for example, WO 96/11698.

For parenteral administration, the compound may be dissolved in a pharmaceutical carrier and administered as either a solution or a suspension. Illustrative of suitable carriers are water, saline, dextrose solutions, fructose solutions, ethanol, or oils of animal, vegetative or synthetic origin. The carrier may also contain other ingredients, for example, preservatives, suspending agents, solubilizing agents, buffers and the like. When the compounds are being administered intrathecally, they may also be dissolved in cerebrospinal fluid.

The active agent is preferably administered in a therapeutically effective amount. The actual amount administered, and the rate and time-course of administration, will depend on the nature and severity of the condition being treated. Prescription of treatment, e.g. decisions on dosage, timing, etc., is within the responsibility of general practitioners or specialists, and typically takes account of the disorder to be treated, the condition of the individual patient, the site of delivery, the method of administration and other factors known to practitioners. Examples of techniques and protocols can be found in *Remington's Pharmaceutical Sciences*.

Alternatively, targeting therapies may be used to deliver the active agent more specifically to certain types of cell, by the use of targeting systems such as antibodies or cell specific ligands. Targeting may be desirable for a variety of reasons, e.g. if the agent is unacceptably toxic, or if it would otherwise require too high a dosage, or if it would not otherwise be able to enter the target cells.

Instead of administering these agents directly, they could be produced in the target cell, e.g. in a viral vector such as described above or in a cell based delivery system such as described in U.S. Pat. No. 5,550,050 and published PCT application Nos. WO 92/19195, WO 94/25503, WO 95/01203, WO 95/05452, WO 96/02286, WO 96/02646, WO 96/40871, WO 96/40959 and WO 97/12635, designed for implantation in a patient. The vector could be targeted to the specific cells to be treated, or it could contain regulatory elements which are more tissue specific to the target cells. The cell based delivery system is designed to be-implanted in a patient's body at the desired target site and contains a coding sequence for the active agent. Alternatively, the agent could be administered in a precursor form for conversion to the active form by an activating agent produced in, or targeted to, the cells to be treated. See for example, EP 425,731A and WO 90/07936.

The practice of the present invention employs, unless otherwise indicated, conventional techniques of chemistry, molecular biology, microbiology, recombinant DNA, genetics, immunology, cell biology, cell culture and transgenic biology, which are within the skill of the art. See, e.g., Maniatis et al., 1982; Sambrook et al., 1989; Ausubel et al., 1992; Glover, 1985; Anand, 1992; Guthrie and Fink, 1991; Harlow and Lane, 1988; Jakoby and Pastan, 1979; *Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., N.Y.); *Gene Transfer Vectors For Mammalian Cells* (J. H. Miller and M. P. Calos eds., 1987, Cold Spring Harbor Laboratory); *Methods In Enzymology*, Vols. 154 and 155 (Wu et al. eds.), *Immunochemical Methods In Cell And Molecular Biology* (Mayer and Walker, eds., Academic Press, London, 1987); *Handbook Of Experimental Immunology*, Volumes I–IV (D. M. Weir and C. C. Blackwell, eds., 1986); Hogan et al., Manipulating the Mouse Embryo, (Cold Spring Harbor Laboratory Press, Cold Spring Harbor, N.Y., 1986). A general discussion of techniques and materials for human gene mapping, including mapping of human chromosome 1, is provided, e.g., in White and Lalouel, 1988.

EXAMPLES

The present invention is further detailed in the following examples, which are offered by way of illustration and are not intended to limit the invention in any manner. Standard techniques well known in the art or the techniques specifically described below are utilized.

EXAMPLE 1

Materials and Methods

Cell lines and tissues. Cancer cell lines were obtained from the American Type Culture Collection (ATCC) and cultured in the recommended growth medium or in bronchial epithelial growth medium (Clonetics; San Diego, Calif.). All non-microdissected primary frozen lung tumors were classified and obtained from the Pathology Department of the City of Hope Medical Center (Duarte, Calif.).

cDNA isolation and DNA sequence determination. A human leukocyte cDNA library (Clontech, Palo Alto, Calif.), a human spleen cDNA library (Clontech), and human universal cDNA library array membranes (Stratagene, La Jolla, Calif.) were screened by hybridization with single stranded gene-specific PCR probes. PCR fragments for exons 1α, 2αβ and 2γ were amplified form genomic DNA using standard PCR conditions. The hybridization probes were made by repeated run-off polymerization of the respective PCR probes (Törmänen and Pfeifer, 1992). All described sequences were determined by cycle sequencing and run on an ABI377 automated DNA sequencer. The sequence homologies were identified using BLAST (Altschul et al., 1997).

Northern blot analysis. Total RNAs from cell lines were isolated by the guanidinium isothiocyanate method (RNAgents; Promega, Madison, Wis.). Poly(A) RNA was isolated using the Poly(A)Pure mRNA isolation kit (Ambion, Austin, Tex.). Two μg of poly(A) mRNA was separated on a 1% agarose-formaldehyde gel and transferred to a nylon membrane. The multiple tissue poly (A) Northern blots were purchased from Clontech. Hybridization was performed using single stranded PCR probes specific for exons 1β, 1β, 2αβ and 2γ.

RT-PCR analysis. RT-PCR was essentially performed as described (Szabo and Mann, 1995). Briefly, 0.5 μg of RNA was pre-associated with 50 pmoles of a lower primer from exon 4 (5'GATGAAGCCTGTGTAAGAACCGTCCT (SEQ ID NO:10)). After the RT reaction, half of the samples were pipetted into tubes containing PCR master mix and 50 pmoles of upper primer from exon 2αβ (5'CAGATTGCAAGTTCACCTGCCACTA (SEQ ID NO:11)) and the remaining half was added into tubes containing PCR mix and 50 pmoles of upper primer from exon 2γ (5 'CGGAGGCGCCTTCTTTCGAAATGACCT (SEQ ID NO:12)). PCR conditions were 95° C. for 1 min, 60° C. for 1 min and 74° C. for 2 min for 35 cycles. PCR products were separated on 2% TBE agarose gels, hybridized with the corresponding labeled probes and visualized by autoradiography.

Mutation screening. Exon sequences were amplified by mixing 200 ng of genomic DNA with 16 pmoles of each primer in 100 μl reaction buffer containing 100 μM of each dNTP and Taq polymerase (Boehringer, Mannheim) at 95° C. for 1 min, 55–60° C. for 1 min and 74° C. for 35 cycles. PCR products were purified using QIAquick PCR purification kit or by gel with the QIAEXII gel purification kits (Qiagen, Valencia, Calif.) and both strands were sequenced directly without subcloning.

Methylation analysis. DNA was isolated from cells and frozen tumors by digestion with 0.5 mg/ml proteinase K in 0.5% NP40, 0.5% SDS, 50 mM Tris, pH 7.6, and 25 mM EDTA, pH 8, followed by standard phenol-chloroform extraction and ethanol precipitation. The methylation status of the promoter region A was determined by a bisulfite genomic sequencing protocol (Clark et al., 1994). Briefly, 2 μg of genomic DNA was digested with EcoRI and precipitated. The DNA was denatured in 0.3 M NaOH for 15 min at 37° C. Cytosines were sulfonated in 3.12 M sodium bisulfite (Sigma; St. Louis, Mo.) and 5 mM hydroquinone (Sigma) in a thermocycler for 30 sec at 99° C. and for 15 min at 50° C. for 20 cycles. The DNA sample was desalted through a column (Wizard DNA Clean-Up System, Promega), desulfonated in 0.3 M NaOH and precipitated. DNA sequences were amplified by mixing 100 ng of bisulfite treated DNA with 50 pmoles of primer MU379 (5'GTTTTGGTAGTTTAATGAGTTTAGGTTTTTT (SEQ ID NO:13)) and 50 pmoles of primer ML730 (5'ACCCTCTTCCTCTAACACAATAAAACTAACC (SEQ ID NO:14)) in 100μl reaction buffer containing 200 μM of each dNTP and Taq polymerase (Boehringer Mannheim; Indianapolis, Ind.) at 95° C. for 1 min, 55° C. for 1 min and 74° C. for 2 min for 30 cycles. A semi-nested PCR was performed using 1/50 of the amplified products and an internal primer ML561 (5'CCCCACAATCCCTACACCCAAAT (SEQ ID NO:15)) and primer MU379 with similar conditions as described for the preceding PCR amplification. The PCR products were purified using QIAquick PCR purification kit (Qiagen, Valencia, Calif.). Products were directly sequenced to obtain average methylation levels. PCR products containing bisulfite resistant cytosines were ligated into the pCR2.1 vector (Invitrogen; Carlsbad, Calif.) and several clones were sequenced for confirmation.

Re-expression of RASSF1.A by 5-azadeoxycytidine treatment. A549 lung carcinoma and MDAMB231 breast carcinoma cells were treated with 5-aza-2'-deoxycytidine (5-Aza-CdR). 5×10$^6$ cells each were grown for four days in presence of different concentrations of 5-Aza-CdR. RNA was isolated and RT-PCR was performed as described above to analyze transcript A.

Cell growth assays. The RASSF1.A cDNA was cloned into the pcDNA3.1(+) vector (Invitrogen). 2 μg of cDNA-containing plasmid was transfected into A549 lung carcinoma cells using the lipofectamine method. Empty vector was transfected as a control. 5×10$^3$ vector- and RASSF1.A-transfected cells were grown on triplicate plates in two independent experiments. After G418 (1mg/ml) selection for 2 weeks, the colonies were stained and counted.

Colonies were isolated after G418 selection and RASSF1.A expression was confirmed by RT-PCR. Two vector- and two RASSF1.A-transfected clones were subjected to an anchorage-independent growth assay. 10$^4$ cells each were mixed with 1.5 ml of plating agar (0.3% in DMEM) and overlaid on 3 ml 0.5% agar. The plates were incubated for 14 days and stained. Colonies with a diameter greater than 100 μm were counted.

Tumor Studies. The same clones used for the soft agar assays were used to analyze tumor growth in nude mice. The work was done in accordance with institutional animal care guidelines. Cells were harvested, re-suspended in PBS and mixed 1:1 with Matrigel (Becton Dickson, Bedford Mass.).

300 μl (7×10⁶ cells) were injected subcutaneously into the right flank of female 5–6 week-old athymic BALB/c nude mice (Charles Rivers Laboratories; Wilmington, Mass.). There were four experimental groups of six to eight mice each. The tumors were measured with calipers weekly for 6 weeks. Tumor volume was calculated as length×height× width×0.5. After six weeks the mice were sacrificed and tumors were dissected and weighed. Tumor weights and volumes gave comparable results. Expression of RASSF1.A in the tumor cells was confirmed for several tumors by RT-PCR.

GenBank accession numbers. The longest cDNA sequences of RASSF1.A, RASSF1.B and RASSF1.C have been deposited into GenBank (accession numbers AF132675, AF132677, and AF132676, respectively).

EXAMPLE 2

Identification of the RASSF1 Gene

A cDNA encoding a candidate protein interacting with the human DNA excision repair protein XPA was isolated from a human keratinocyte cDNA library in the yeast two-hybrid system. A 1675 bp long cDNA was obtained. Sequence analysis using the BLAST search (National Center of Biotechnology Information) was performed. The nucleotide (nt) sequence matched the sequences of human cosmid clones LUCA12 and LUCA13 (Wei et al., 1996; GenBank accession numbers AC002481 and AC002455, respectively). Both cosmids are in the minimum homozygous deletion region of 120 kb (Sekido et al., 1998; and see FIG. 1A) that may contain the putative lung tumor supressor gene at 3p21.3. The C-terminus of the translated nt sequence of the obtained cDNA clone shows high homology (ca. 55% identity) to the murine Ras effector protein Nore1 and to the homologous rat protein Maxp1 (FIG. 1C). Nore1 interacts with Ras in a GTP-dependent manner and is the only candidate mammalian Ras effector, other than Raf, wherein the endogenous polypeptide has been shown to associate with Ras in vivo following receptor activation (Vavvas et al., 1998). Since the N-terminus of the initially obtained Ras effector homologue (REH) showed almost no homology to these proteins, we screened several additional cDNA libraries. We obtained three alternatively spliced transcripts: RASSF1.A, RASSF1.B and RASSF1.C (FIG. 1B).

All three transcripts have four common exons (3 to 6) at their 3' end. These exons encode a Ras association (RalGDS/AF-6) domain (RA) (Ponting and Benjamin, 1996). Transcript A has two 5' exons, designated 1α and 2αβ (FIG. 1B). This cDNA is 1873 bp long and contains an ORF of 340 amino acids (aas) with a calculated MW of 38.8 kDa. The N-terminus (H 52 to C 101) of RASSF1.A has high homology to a cystein-rich diacylglycerol/phorbol ester binding domain, also known as the protein kinase C conserved region 1 (C1) domain (Newton, 1995). Transcript RASSF1.B has the same exon 2αβ but the first exon 1β is different from that of transcript A (FIG. 1). In the first two exons no Kozak consensus sequence was found. The first AUG codon in the same frame as that of transcript A was localized at the 3' end of exon 3. Most likely the 1664 bp cDNA of RASSF1.B encodes only the Ras association domain. Transcript RASSF1.C is 1.7 kb long and transcription initiates in exon 2γ which has an AUG initiation codon. The cDNA encodes a 270 aa protein with a MW of 31.2 kDa. The protein sequence translated from the first exon 2γ has no similarity to Nore1 and any other known protein (FIG. 1C).

EXAMPLE 3

Expression of the RASSF1 Gene

To investigate expression of the RASSF1 gene we performed a detailed Northern blot analysis (FIG. 2). Human multiple tissue Northern blots were hybridized with different labeled PCR probes. A probe from exon 2γ hybridized with a major 1.8 kb long mRNA (FIG. 2D). This signal was present in 16 normal tissues and 8 human cancer cell lines. Using a probe from exon 2αβ an approximately 1.9 kb mRNA was obtained (FIG. 2A). All normal tissues and four cancer cell lines showed expression of this exon. However, in four cancer cell lines this band was completely missing (MOLT-4, Raji, A549 and G361). A very similar pattern was obtained using a probe from exon 1α (FIG. 2B). Using a probe specific for exon 1β which is specific for transcript B, the signals were much weaker than for transcripts A and C (FIG. 2C). Transcript B was mainly expressed in tissues containing cells from the hematopoetic system. On all blots we could detect at least two to three distinct signals migrating between 7.5 and 11 kb. With a probe specific for the 5 kb long intron between exons 2γ and 3 we obtained exactly the same length and pattern of signals on these blots. These longer mRNAs are most likely unspliced precursor mRNAs. Indeed, in the cancer cell lines, which do not express transcript A, only one precursor mRNA of 7.5 kb is present (FIG. 2D). These transcripts presumably initiate in the promoter located in CpG island C (FIG. 1B). In the cancer cell lines expressing transcript A two longer precursor mRNA are present (8.5 and 11 kb), which also hybridize to a probe located upstream of CpG island C (FIGS. 2 A, B). These transcripts most likely initiate in CpG island A. In the cancer cell lines not expressing transcript A, these two precursor mRNAs are absent.

Figure 3B:
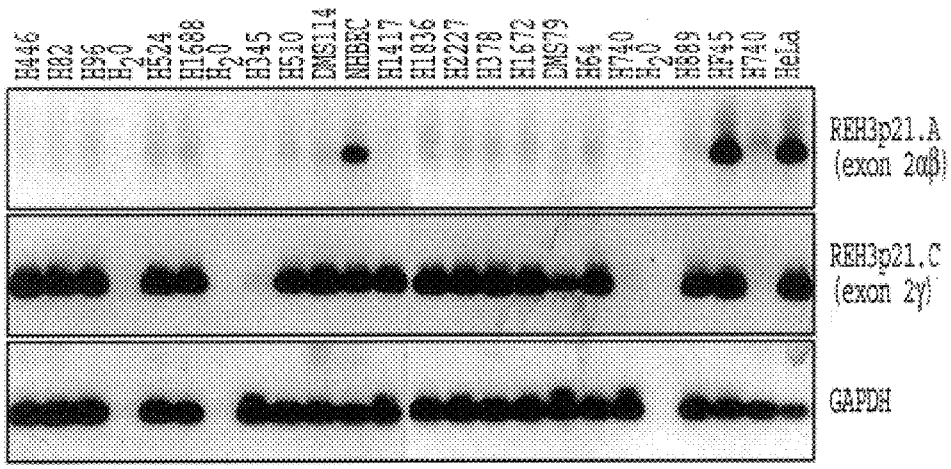

In FIG. 3A we analyzed the expression of RASSF1 in several other cancer and normal cell lines by Northern blot. All examined cell lines showed transcription of RASSF1.C when using a probe from exon 2γ (FIG. 3A). Hybridization of the blot with a probe from exon 2αβ showed that several cancer cell lines lacked the corresponding transcripts (FIG. 3A). Two small-cell lung carcinomas, a cervical carcinoma (C33A) and a mammary carcinoma (MDAMB231) had no detectable expression. AD293, SJSA and SKN-SH cells showed only traces of expression. In the hepatoma cell line HepG2 a smaller transcript of about 1.5 kb was present. Only colon carcinoma HT-29 and mammary carcinoma HS578-T showed a transcript level comparable to normal human bronchial epithelial cells (NHBEC) and normal human skin fibroblasts (HF57). Further, we analyzed 17 small-cell lung cancer cell lines by RT-PCR. In FIG. 3B we used a lower primer from exon 4 for the reverse transcriptase reaction and either an upper primer from the 5' end of exon 2αβ or a primer from the 5' end of exon 2γ for the PCR. The products were separated on a gel, blotted onto a membrane and hybridized with the corresponding probes (exon 2αβ or exon 2γ, respectively). Only NHBECs, fibroblasts (HF45) and HeLa cells gave products with the primer specific for exon 2αβ (FIG. 3B). This clearly demonstrates that none of the 17 SCLCs expresses transcript RASSF1.A, whereas 16 of the SCLCs expressed transcript RASSF1.C (FIG. 3B). In the homozygous deletion cell line H740 the transcript C is missing, as expected, and it is reduced in H345.

EXAMPLE 4

CpG Methylation Analysis

Figure 4B:
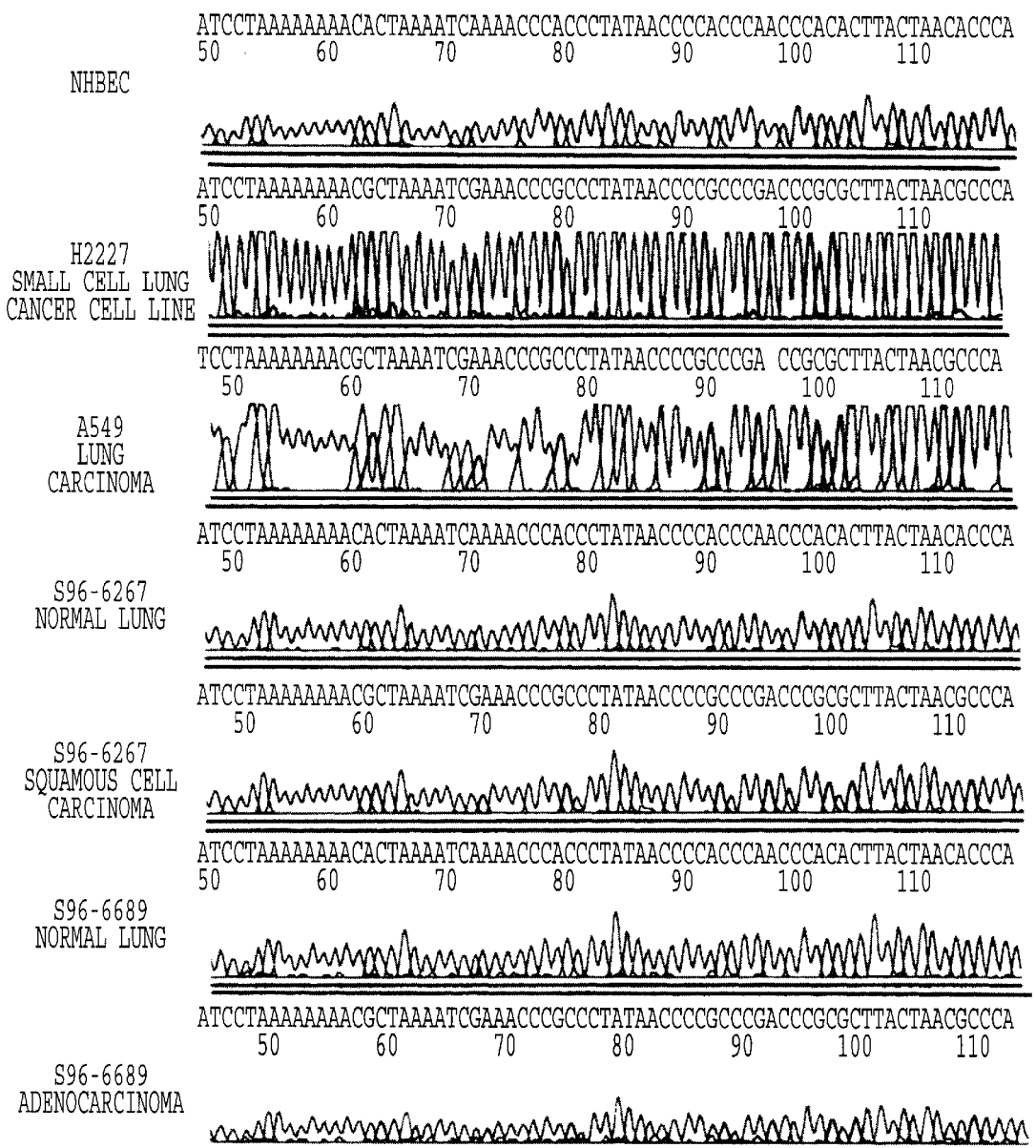

CpG methylation in mammalian DNA is one of the mechanisms responsible for gene silencing (Razin and Riggs, (1980). In addition to deletion or point mutation, the function of a tumor suppressor gene may be lost by promoter hypermethylation (Baylin et al., 1998; Jones and Laird, 1999; Costello et al., 2000; Eng et al., 2000). We used bisulfite sequencing of genomic DNA (Clark et al., 1994) to determine the methylation status of CpG island A where transcript A initiates. In this method, sodium bisulfite is used to convert all unmethylated cytosines to uracils, then to thymines during the subsequent PCR step. Since 5-methylcytosine remains non-reactive, all cytosines after sequence analysis present only methlyated cytosines. All guanines present after sequencing in FIG. 4B are therefore derived from methylated cytosines on the complementary strand.

Figure 4C:
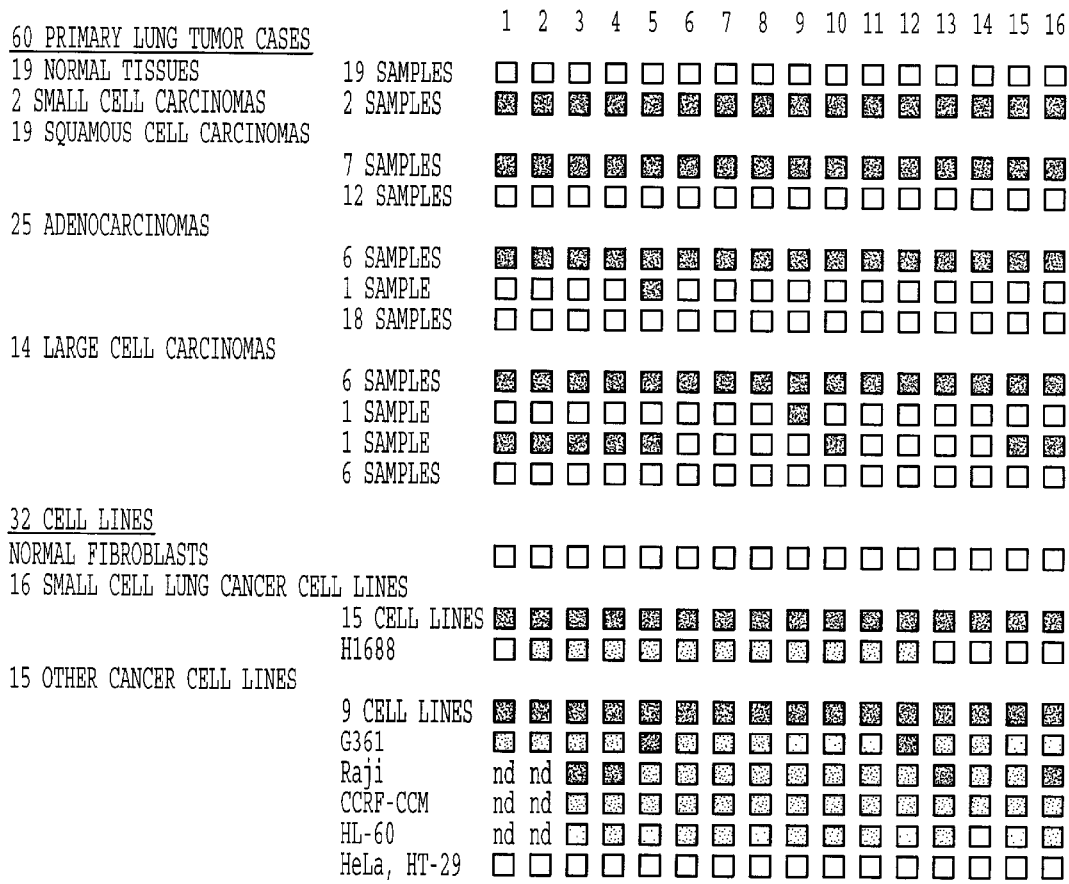

We analyzed 16 CpGs in a 204 bp fragment containing three Sp1 consensus binding sites and the putative transcription and translation initiation sites for transcript A. In NHBEC and fibroblast DNA, all Cs were deaminated to Us and then represented as As on the complementary strand (open squares in FIG. 4C), and are therefore unmethylated. 15 small-cell lung cancers were completely methylated in this region (black squares) and only one (H1688) was partially methylated (FIG. 4). From the 15 other cancer cell lines examined 9 were completely methylated (A549, MOLT-4,AD293, HepG2,SJSA, SAOS, SK-N-SH, C33A and MDAMB231). Four showed partial methylation (G361, Raji, CCRF-CCM, HL-60) and two were not methylated (HeLa and HT-29) (FIG. 4C). This correlates quite well with their expression levels (FIG. 3). Furthermore the methylation pattern of primary tumors was investigated. 58 non-small-cell lung carcinomas and two small-cell lung carcinoma were obtained from lung tumor patients at the City of Hope Medical Center.

The methylation status of the CpG island A was determined by the bisulfite technique and methylation positive samples were confirmed by subdloning and sequencing of several individual clones. FIG. 4B shows some of these results. All 19 normal lung tissue samples examined were unmethylated. Two primary small-cell lung tumors were completely methylated at all 16 CpG sites. Seven out of 19 squamous cell carcinomas were completely methylated. Seven adenocarcinomas and eight large cell carcinoma were at least partially methylated (FIG. 4C). We could not detect any methylation in CpG island C in any tumor or cell line tested (data not shown). This is consistent with the transcriptional activity of the promoter of RASSF1.C (FIGS. 2 and 3). Taken together, 38% of the NSCLC tumors and 100% of the SCLC tumors or cell lines were highly methylated in the promoter region of RASSF1.A.

EXAMPLE 5

Mutation Analysis

The cDNA of the RASSF1.A gene was sequenced to search for mutational events. No mutation was found in the 17 SCLC cell lines. In 41 primary NSCLCs, four missense mutations were identified: GAC(Asp129) to GAG(Glu129), ATT(Ile135) to ACT(Thr135), CGG(Arg257) to CAG (Gln257), and GCC(Ala336) to ACC (Thr336). A common polymorphism was found in exon 1α[AAG(Lys21)/CAG (Gln21)]. Expression of transcript A is lost in tumor cell lines with extensive methylation (FIGS. 2–4). For primary tumors, this analysis is more difficult because normal cells are almost invariably present along with tumor cells. However, we found a reduction (and in several cases a complete loss) of expression in primary tumors versus normal tissue by RT-PCR). The tumors with mutation were unmethylated in 3 out of 4 cases.

EXAMPLE 6

Analysis of Epigenetic Inactivation

Figure 5:
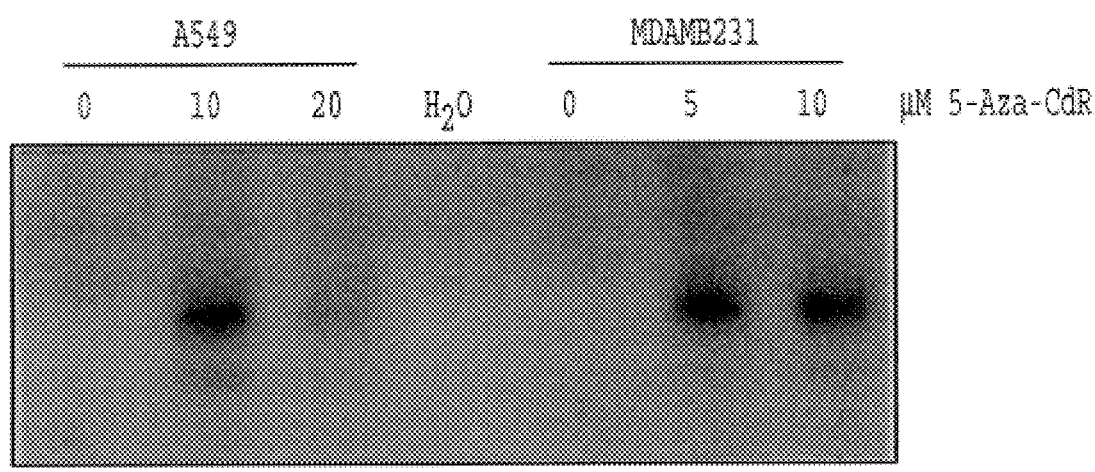
FIG. 5 shows re-expression of transcript A by treatment with 5-aza-2'-deoxycytidine (5-Aza-CdR). A549 and MDAMB231 cells were treated for 4 days with the indicated concentrations of 5-Aza-CdR. Transcript A was analyzed by RT-PCR.

Epigenetic inactivation of genes can be reversed by treatment of cells with the DNA methylation inhibitor 5-aza-2'-deoxycytidine (5-Aza-CdR). Two cell lines that did not express transcript A (A549 and MDAMB231) were treated with this compound. 5-Aza-CdR reactivated expression of RASSF1.A in both cell lines (FIG. 5) indicating that repression is at least in part mediated by methylation. The high level of epigenetic inactivation of the RASSF1.A gene indicates that this gene functions as a tumor suppressor in 3p21.3. Methylation is the dominant inactivation mechanism affecting this gene. Loss of heterozygosity at 3p21.3 (Kok et al., 1997; Hung et al., 1995; Wistuba et al., 1999; Sekido et al., 1998; Wei et al., 1996) and de novo methylation of CpG islands (Belinsky et al., 1998) may be common and early events in the pathogenesis of lung cancer.

EXAMPLE 7

RASSF1Affects Cell Growth

Figure 6A:
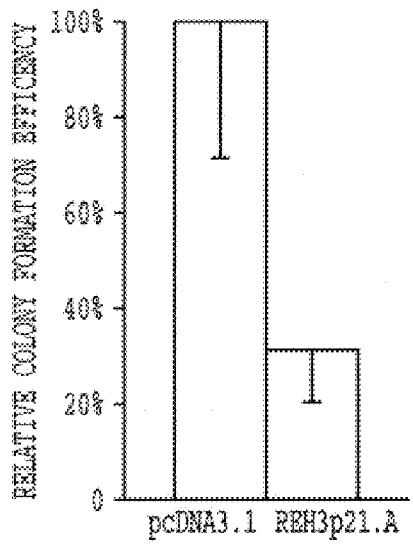
FIGS. 6A–6E show effect of RASSF1.A expression on cell growth characteristics. (A) Colony formation assay. A549 cells were transfected with vector (pcDNA3.1) or with the vector containing the cDNA of RASSF1.A. Colonies were counted after G418 selection for 14 days. (B–D) Anchorage-independent growth assay in soft agar. (B) Colonies with a diameter of greater than 100 μm were counted for two clones transfected with vector and cDNA, respectively. (C) A549 cells transfected with RASSF1.A cDNA (RASSF1.A-5). (D) A549 cells transfected with vector (pcDNA3.1-18). (E) Tumor formation in nude mice. Two vector transfected clones (pcDNA3.1-18 and pcDNA3.1-8) and two cDNA-transfected clones (RASSF1.A-5 and RASSF1.A-11) were injected into BALB/c nude mice. Tumor volume was determined weekly.
Figure 6B:
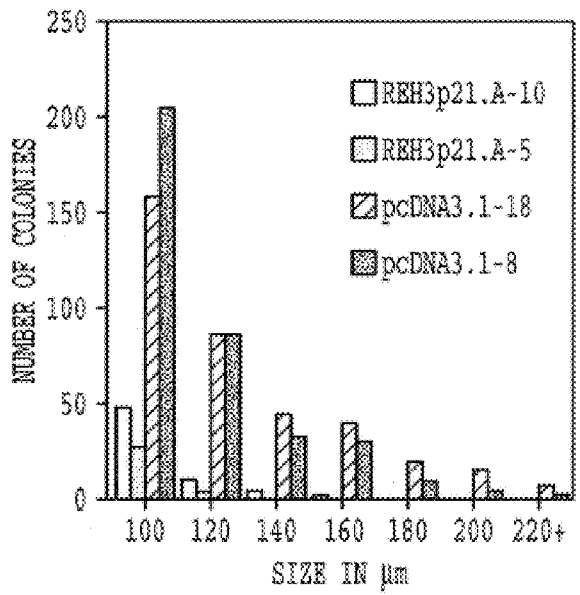
Figure 6C:
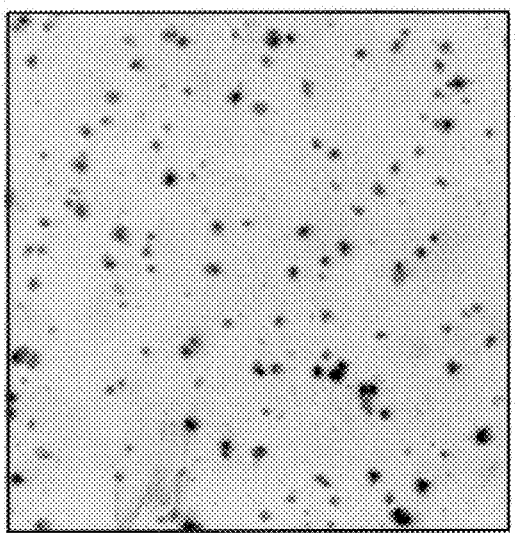
Figure 6D:
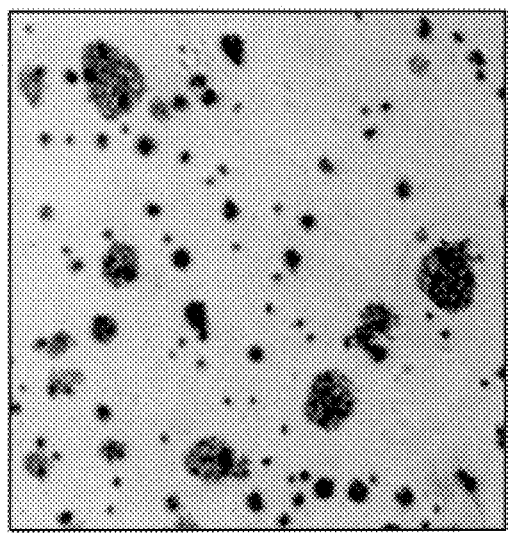
Figure 6E:
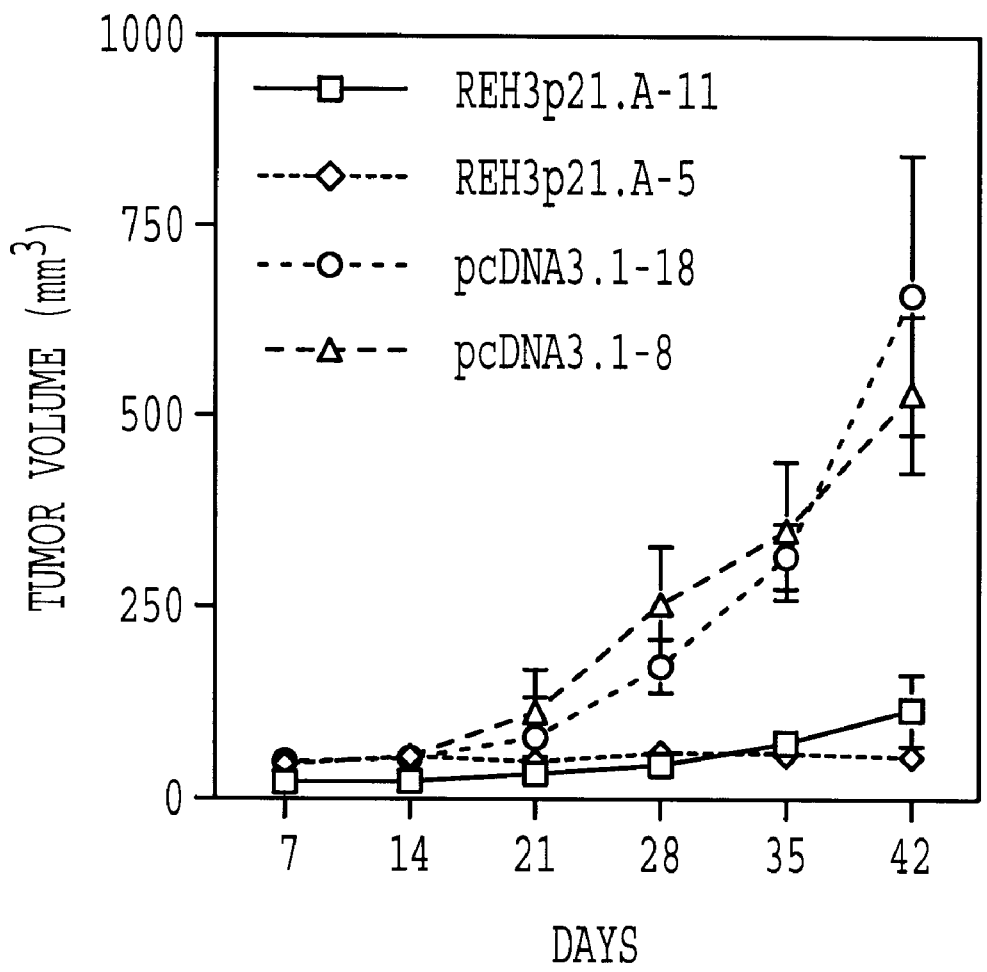

The presence of a Ras association domain and the high degree of homology with Nore1 suggest that this protein may function in a Ras signaling pathway or related pathway, perhaps as a negative regulator of cell growth. To determine if re-introduction of transcript A into lung cancer cells affects cell growth, A549 cells were transfected with the cDNA encoding transcript A (FIG. 6). Colony formation, as measured after G418 selection, was reduced to about one third of the vector control (FIG. 6A). Clones re-expressing transcript A and controls were subjected to soft agar cloning assays. Anchorage-independent growth in soft agar was strongly diminished in cells re-expressing RASSF1.A (FIG. 6B–D). The same clones were injected into athymic mice and assayed for tumor formation. Tumor size was strongly reduced in the groups of mice injected with A549 clones re-expressing transcript A compared to vector-transfected controls (FIG. 6E).

EXAMPLE 8

Therapeutical Use of RASSF1

Retroviral vectors containing transcript A are prepared as described in U.S. Pat. Nos. 5,691,198 and 6,017,521. Cells of the lung cancer cell line A549 are infected with the transcript A-containing retroviral vectors as described in these patents. As found in Example 7, A549 cells infected with the retroviral vectors containing transcript A showed a reduction in colony formation, and clones expressing transcript A showed a diminished anchorage-independent growth in soft agar when compared to the vector controls.

The tumorgenicity of A549 cells and the A549 clones expressing transcript A is tested by subcutaneous inoculation in nude mice as described in Example 1. At the high dose tested, all mice developed tumors with both the A549 cells and with the A549 clones expressing transcript A. However, the tumors in the mice receiving the A549 clones expressing transcript A grew at a strongly reduced rate compared to the tumors in mice receiving the unmodified A549 cells. Examples 7 and 8 demonstrate that expression of transcript A reproducibly reduces the rate of tumor growth.

EXAMPLE 9

Clinical Protocol for Tumor Suppressor Gene Expression in Small Cell Lung Cancer This example is provided to demonstrate a protocol for administering and assessing the efficacy and toxicity of the intralesional administration of retroviral constructs containing wild-type RASSF1 transcript A (wtA) (for tumors with mutated, deleted or non-expressed transcript A) into residual endobronchial SCLC which obstructs a bronchus and which is refractory to conventional therapy.

A LNSX retroviral vector construct containing the A transcript cDNA with a β-actin promoter (LNSX-wtA) is prepared as described in U.S. Pat. No. 6,017,521. Because recombination events may lead to the production of a replication-competent virus, a safe and efficient amphotropic packaging cell line is necessary for transfer of exogenous genes into human cancer cells. The packaging cell line employed is constructed and the presence of functioning retroviral genes is monitored as described in U.S. Pat. No. 6,017,521. Continued absence of infectious virus will be determined from transfection-infection experiments as described in U.S. Pat. No. 6,017,521. Lack of infectivity in these experiments will indicate absence of replication competent virus. Retroviral particles are generated as described in U.S. Pat. No. 6,017,521.

Preclinical studies are conducted by transducing the LNSX-wtA and control vecotor are transduced into A549 lung carcinoma cells (no expression of RASSF1.A). A549 cells that underwent one cycle of infection with the wtA construct but without G418 selection had reduced proliferation compared to cells that received either the unmodified vector or no treatment. Two cycles of transduction without G418 selection resulted in a further reduction in proliferation. Thus, retroviral mediated gene transfer of wtA into human lung cancer cells with non-expressing transcript A reduces the proliferation of those cells. The non-expression of the wtA is uniform in cultured cell lines as detected by immunohistochemistry.

A critical question is the ability of the retroviral constructs to transduce established tumor cells in vivo. This question is addressed by injecting A549 cells in the mouse right mainstem bronchus followed 3 days later by lavage with LNSX retroviral supernatant. LNSX is used so that the neo gene could be used as a marker for transduction. Tumors are harvested and the presence of the neo gene is assessed by Southern hybridization. The neo gene is detected in the DNA from the A549 cells indicating successful transduction of the retrovirus.

In proposed preferred treatment protocols, patients will undergo bronchoscopy to assess the degree of obstruction. As much gross tumor as possible should be resected endoscopically. Patients should preferably undergo bronchoscopy under topical or general anesthesia. A Stifcor™ transbronchial aspiration needle (21 g) will be passed through the biopsy channel of the bronchoscope. The residual tumor site will be injected with the appropriate retroviral supernatant. The volume will be no greater than 10 ml. Protamine will be added at a concentration of 5 μg/ml. This is 0.2% of the amount given intravenously to reverse heparinization. Injections will be circumferential and will be intratumor and submucosal. The injections will be repeated daily for five consecutive days. The treatment will be repeated monthly.

There are various criteria that one should consider as presenting the existence of a need for response or the existence of toxicity. To assist in determining the existence of toxicity, the tumor bed should be photographed prior to a course of therapy. The longest diameter and its perpendicular will be measured. Size will be reported as the product of the diameters. From these date, one can calculate from these numbers the rate of regrowth of the tumor.

The time to progression can also be measured from the first observation with reduction in tumor bulk until there is evidence of progressive disease. Progressive Disease is defined as an increase of ≧25% in the sum of the products of the diameters of the measured lesion. Patients must have received at least two courses of therapy before a designation of progression is made. The survival of patients will be measured from entry into protocol.

The possibility of causing malignancy in normal cells secondary to random insertion of the retroviral vector in the genome exists although this risk is thought to be very low. Tests of viral supernatant will be conducted to assure that no replication competent virus is present. Non-replicating bronchial epithelial cells will not take up the vector.

The retrovirus derived from the Moloney murine leukemia virus is modified so that it no longer contains intact viral genes. Thus, it cannot produce an intact infectious virus. Assays may be performed on the retroviral vector supernatant and the packaging cell to insure that replication competent virus is not present. Extensive safety studies have been performed on this retroviral construct in primates. Large infusions of infectious murine amphotrophic virus produce no acute pathologic effects. Primates have also received retroviral gene-modified autologous bone marrow cells with no evidence of toxicity as long as 4 years after infusion.

The neomycin resistance gene product, neomycin phosphotransferase, phosphorylates the 3' hydroxyl group of the aminohexose I of neomycin and its analogues. Amikacin, but not gentamicin and tobramycin which do not contain an hydroxyl at the 3" position, is inactivated. Thus, induction of the neomycin resistance gene would not exclude aminoglycosides or any other conventional antibiotic from use in these patients.

There are various criteria that one should consider employing in making a decision to discontinue therapy. For example, an increase in the endobronchial tumor after a minimum of 2 or more courses of therapy, or the development of unacceptable toxicity defined as unpredictable, irreversible, or Grade 4. Patient refusal of therapy due to a specific toxicity should be graded as 4 and an explanatory note recorded. One should also consider discontinuing therapy upon the occurrence of significant hemoptysis, coagulopathy, or progressive postobstructive pneumonia.

EXAMPLE 10

Methylation Status of RASSF1 in Primary Small Lung Carcinomas

To analyze the RASSF1 gene in primary small cell lung carcinomas (SCLCs), we determined the methylation status of the two CpG islands, in which the alternative RASSF1A and RASSF1C transcripts initiate (FIG. 1B). We used bisulfite sequencing of genomic DNA (Clark et al., 1994) to determine the methylation status of CpG dinucleotides. In this method, sodium bisulfite is used to convert all umnethylated cytosines to uracils, then to thymines during a subsequent PCR step. Since 5-methylcytosine remains nonreactive, all cytosines after sequence analysis represent only methylated cytosines.

More specifically, the data shown were obtained by direct sequencing of PCR products from bisulfite-treated DNA or from PCR products subcloned into plasmids (two primary tumors and matched normal tissue controls). Small cell lung carcinomas and the corresponding normal lung tissues were obtained from the Aichi Cancer Center Research Institute and the City of Hope National Medical Center. DNA was isolated from tumors, and the methylation status of the RASSF1A promoter region was determined by a bisulfite genomic sequencing protocol (Clark et al., 1994; Dammann et al., 2000). DNA sequences were amplified by mixing 100 ng of bisulfite-treated DNA with primers MU379 (5'GTTTTGGTAGTTTAATGAGTTTAGGTTTTTT (SEQ ID NO:13)) and ML730 (5'ACCCTCTTCCTCTAACACAATAAAACTAACC (SEQ ID NO:14)) in 100 µl reaction buffer containing 200 µM of each dNTP and Taq polymerase (Roche Diagnostics Corp.; Indianapolis, Ind.) and incubating at 95° C. for 15 sec, 55° C. for 15 sec and 74° C. for 30 sec, for 20 cycles. A semi-nested PCR was performed using 1/50 of the initially amplified products and an internal primer ML561 (5'CCCCACAATCCCTACACCCAAAT (SEQ ID NO:15)) and primer MU379 with similar conditions as described for the preceding PCR amplification, but for 30 cycles. PCR products were initially sequenced directly to obtain average methylation levels and then subcloned for confirmation.

Figure 7:
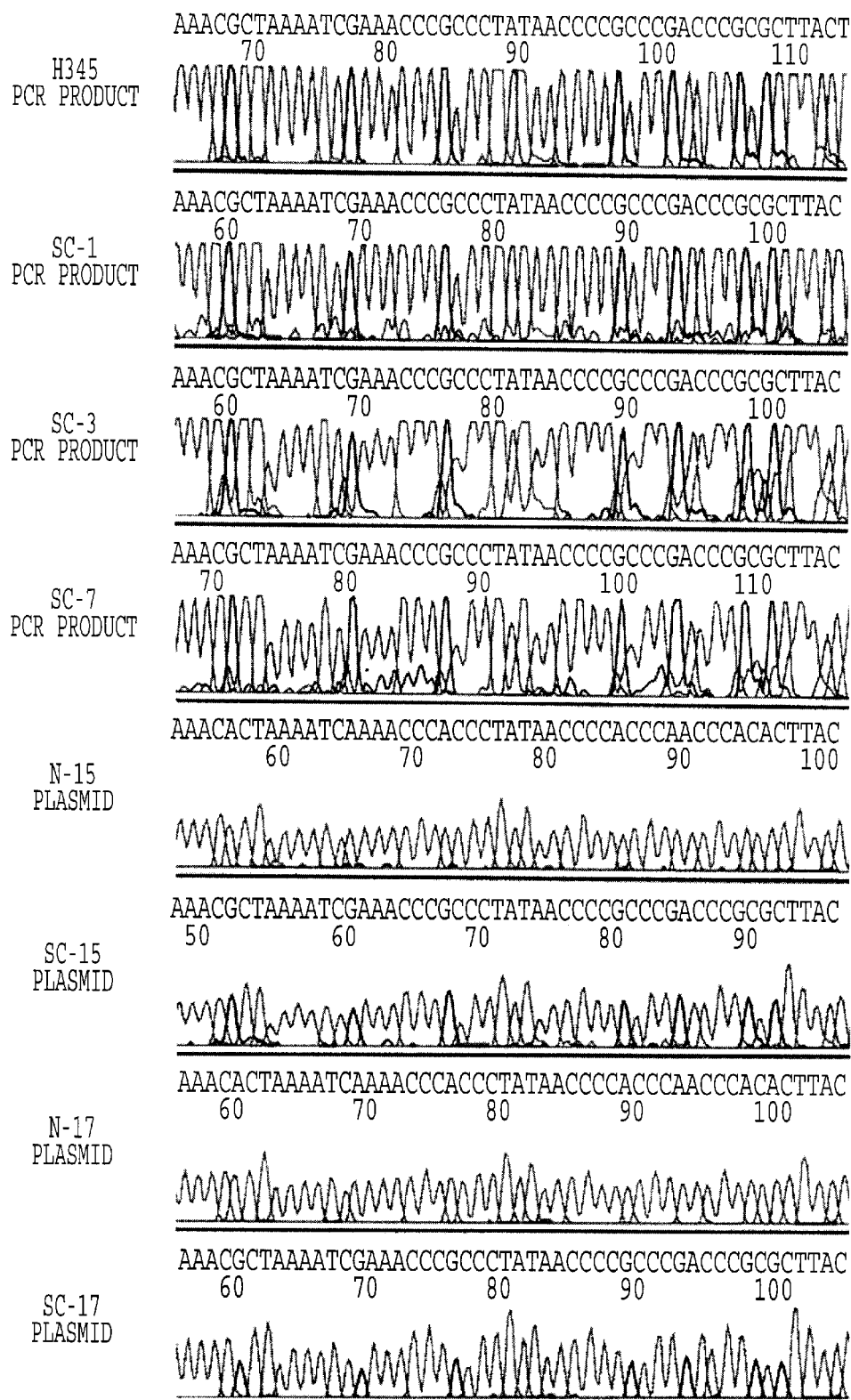
FIG. 7 shows methylation analysis for small cell lung carcinomas. Sequences of PCR products from bisulfite-treated DNA for the CpG island spanning the RASSF1A promoter were obtained from different cancer and normal samples. Methylated cytosines appear as a G signal in the complementary strand (bold Gs). The sequence is shown before bisulfite conversion in FIG. 4A. The position of a TaqI restriction site is underlined. Two Sp1 consensus sites are boxed.

All guanines present after sequencing in FIG. 7 are therefore derived from methylated cytosines on the complementary strand. We analyzed 16 CpGs in a 205 bp fragment containing three Sp1 consensus binding sites and the putative transcription and translation initiation sites of RASSF1A. In FIG. 7, one SCLC cell line (H345) shows complete methylation of the sequence analyzed. Further, we analyzed the methylation status of the RASSF1A promoter in 28 primary non-microdissected SCLC samples. Of the 28 samples analyzed, 22 (=79%) were methylated in the promoter region of RASSF1A. Five matching normal tissue samples were available. Several examples, including two matching tumor and normal tissues, are shown in FIG. 7. One of the normal tissue samples was methylated, but to a lower degree than the corresponding tumor (25% versus 80%). The other four normal matching tissue samples were unmethylated. In FIG. 7, five methylated primary small cell lung carcinomas are shown. We estimated from the sequence scans of the uncloned PCR products that the tumor samples SC-1, SC-3, and SC-7 showed more than 80% bisulfite modification-resistant cytosines at all CpGs analyzed. In total, more than 75% of the SCLC samples that were methylated contained more than 60% bisulfite-resistant cytosines at all CpG sequences. This high level of methylation indicates that a large fraction of the tumor cell population has the promoter of RASSF1A methylated. The sequence positions that were found methylated are indicated in FIG. 4A.

Since LOH at 3p21.3 occurs in almost 100% of all SCLC tumors (Whang-Peng et al., 1982; Naylor et al., 1987; Hibi et al., 1992; Kok et al., 1997; Wistuba et al., 2000; Girard et al., 2000; Lindblad-Toh et al., 2000), the remaining allele is silenced by methylation. The high methylation frequency of the RASSF1A promoter correlates well with the high LOH frequencies at 3p21.3 in SCLC.

Another methodology to analyze the PCR fragments obtained from bisulfite-modified DNA is by further digestion with a restriction enzyme that has a CpG in its recognition sequence (Xiong and Laird, 1997). TaqI (5'TCGA-3') or BstUI (5'CGCG-3') will cut only previously methylated DNA after bisulfite treatment and PCR. The consensus sequence will be lost by cytosine deamination in umnethylated samples. The analyzed 205 bp fragment of RASSF1A contains two TaqI restriction sites after bisulfite conversion of CpG-methylated DNA (sites 6 and 16 in FIG. 4A). Restriction digestion of PCR products obtained from DNA methylated at both TaqI sites results in three bands (90, 81 and 34 bp; the two larger ones migrating together).

For the restriction enzyme analysis of PCR products from bisulfite-treated DNA (Xiong and Laird, 1997), 20 ng of the PCR products were digested with 10 units of TaqI (for RASSF1A) or 10 units of BstUI (for RASSF1C) according to conditions specified by the manufacturer of the enzymes (New England Biolabs; Beverly, Mass.) and analyzed on a 2.2% TBE agarose gel. To determine the methylation status of the RASSF1C promoter region, PCR reactions similar to those described in above were performed. For the first PCR reaction primers M1305 (5'GTTTTTTGTGGTAGGTGGGGTTTG (SEQ ID NO:16)) and M1627 (5'AATCCRAATCCTCTTAACTACAATAACCAC (SEQ ID NO:17)) were used. For the nested PCR, the internal primers M1318 (GGTGGGGTTTGTGAGTGGAGTTT (SEQ ID NO:18)) and M1599 (5'ACTACTCRTCRTACTACTCCAAATCATTTC (SEQ ID NO:19)) were utilized.

Figure 8:
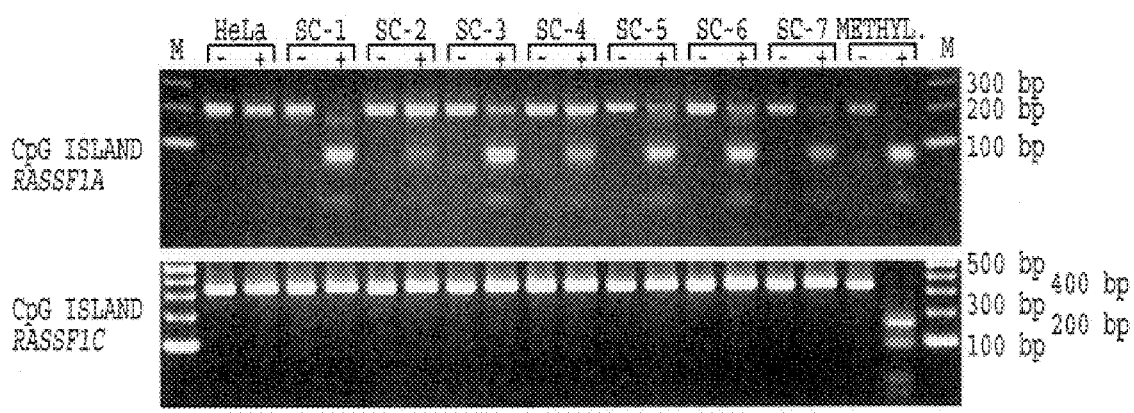
FIG. 8 shows methylation analysis of RASSF1A and RASSF1C by restriction digestion. PCR products from bisulfite-treated DNA obtained from HeLa cells, primary SCLCs (1–7) and in vitro methylated HeLa DNA (Methyl.) were digested (+) or mock-digested (−). The sizes of molecular weight markers (M) are shown on the right in base pairs.

PCR products obtained from DNA from HeLa cells were unmethylated (consistent with expression of RASSF1A in this cell line), whereas in vitro methylated HeLa DNA (Methyl.) was digested at these TaqI sites (FIG. 8). In FIG. 8, we analyzed seven primary small cell lung carcinomas by TaqI restriction (cases SC-1–7). The tumor samples showed approximately 60–95% methylation of the TaqI sites except for sample number SC-2, which was methylated at a level of 30%. For all the analyzed SCLCs the results obtained by restriction digestion and direct sequencing were practically identical. For almost half of the SCLC cases the methylation levels of these CpG sites were higher than 80%.

For comparison, we analyzed the CpG island promoter of RASSF1C. Expression analysis of RASSF1C in SCLC cell lines showed no reduction of transcription. In order to determine the methylation status of the CpG island promoter of RASSF1C in primary SCLCs, we performed restriction analysis of PCR amplified bisulfite-modified DNA. The analyzed 311 bp promoter fragment contains 38 CpGs, one Sp1 consensus binding site and the putative transcription and translation initiation sites of RASSF1C. This methylated fragment has five BstUI sites and digestion results in bands of 140, 89, 31, 21, 16, and 14 bp. The seven SCLCs with high methylation levels at the CpG island of RASSF1A showed no evidence for methylation in the CpG island of RASSF1C (FIG. 8). All analyzed SCLCs were unmethylated at all CpG sites in the promoter of RASSF1C and this was confirmed by direct sequencing.

Methylation and LOH are the major loss of function pathways for the RASSF1A gene since somatic mutations appear to be rare in this gene. We have found no mutations in 16 SCLC cell lines. Epigenetic silencing is a common mechanism for loss of tumor suppressor gene function in cancer. Promoter methylation of tumor suppressor genes, such as p16, and DNA repair genes, such as O6-methylguanine-DNA-methyltransferase, have been detected in DNA from sputum in patients with squamous cell lung cancer several years before clinical diagnosis (Palmisano et al., 2000). A similar methylation analysis of the RASSF1A promoter from sputum of smokers could serve as a sensitive early detection method for small cell lung cancer. This gene may be particularly relevant in this type of analysis, since RASSF1A promoter hypermethylation is a very frequent event, and LOH analysis of the same region predicts that it might be an early change in the pathogenesis of lung cancer.

In a recent study, Vos et al. (2000) have shown that RASSF1 binds RAS in a GTP-dependent manner. Overexpression of RASSF1C induced apoptosis (Vos et al., 2000). This pro-apoptotic effect of RASSF1C is enhanced by activated RAS and inhibited by dominant negative RAS. No epigenetic inactivation of RASSF1C has so far been shown in lung cancer (above). In primary SCLCs, no hypermethylation of the CpG island of RASSF1C could be detected (FIG. 8). Vos et al. (2000) reported a reduction of RASSF1C expression in ovarian tumor cell lines. Since isoforms A and C encode for the identical RAS association domain, it is very likely that RASSF1A will bind to RAS in the same manner as RASSF1C. Activated RAS proteins are usually associated with growth enhancement and transformation. However, RAS also induces growth inhibitory effects manifested by senescence (Serrano et al., 1997), terminal differentiation (Bar-Sagi and Feramisco, 1985) or apoptosis (Mayo et al., 1997; Chen et al., 1998; Downward, 1998; Shao et al., 2000). RASSF1 might be responsible for the RAS-dependent growth inhibition through its pro-apoptotic function (Vos et al., 2000). Loss of RASSF1 expression by methylation in human cancer may shift the balance of RAS activities towards a growth promoting effect without the necessity of RAS activating mutations. Indeed, RAS mutations are found in less than 1% of SCLCs (Mitsudomi et al., 1991; Wagner et al., 1993), whereas inactivation of RASSF1A is close to 80% or 100% by hypermethyation and LOH, respectively. This is consistent with the possibility that RASSF1A might be the tumor suppressor gene, which is associated with the early and frequent loss of the 3p21.3 locus in lung cancer development.

EXAMPLE 11

Analysis of RASSF1 in Breast Cancer

Cell lines and tissues. The breast cancer cell lines MCF7, MDAMB157, MDAMB231, T47D and ZR75-1 were obtained from the American Type Culture Collection (ATCC) and were cultured in the recommended growth medium. All non-microdissected primary frozen breast tumors were classified and obtained from the Pathology Department of the City of Hope National Medical Center (Duarte, Calif.). Each tumor was scored based on formation of tubules, nuclear pleomorphism and mitotic activity. Each of these was assigned a value of 1–3 and then the totals were added for a score and grade assignment (Simpson and Page, 1994).

Methylation analysis. DNA was isolated from cells and tumors, and the methylation status of the RASSF1A promoter region was determined by a bisulfite genomic sequencing protocol (Clark et al., 1994). Briefly, 1 µg of genomic DNA was denatured in 0.3 M sodium hydroxide for 15 min at 37° C. Cytosines were sulfonated in 3.12 M sodium bisulfite (Sigma; St. Louis, Mo.) and 5 mM hydroquinone (Sigma) in a thermocycler for 16 h at 55° C. The DNA samples were desalted through columns (Wizard DNA Clean-Up System, Promega), desulfonated in 0.3 M sodium hydroxide and precipitated. DNA sequences were amplified by mixing 100 ng of bisulfite treated DNA with primers MU379 (5'GTTTTGGTAGTTTAATGAGTTTAGGTTTTTT (SEQ ID NO:13) ) and ML730 (5'ACCCTCTTC-CTCTAACACAATAAAACTAACC (SEQ ID NO:14)) in 100 µl reaction buffer containing 200 µM of each dNTP and Taq polymerase (Roche Diagnostics Corp.; Indianapolis, Ind.) and incubating at 95° C. for 15 sec, 55° C. for 15 sec and 74° C. for 30 sec, for 20 cycles. A semi-nested PCR was performed using 1/50 of the initially amplified products and an internal primer ML561 (5'CCCCACAATCCCTACACCCAAAT (SEQ ID NO:15)) and primer MU379 with similar conditions as described for the preceding PCR amplification, but for 30 cycles. The PCR products were purified using QIAquick PCR purification kits (Qiagen, Valencia, Calif.). Products were sequenced directly to obtain average methylation levels. PCR products containing bisulfite resistant cytosines were ligated into the pCR2.1 vector (Invitrogen; Carlsbad, Calif.), and several clones were sequenced for confirmation. All described sequences were determined by cycle sequencing and run on an ABI 377 automated DNA sequencer. The percentage of methylated alleles was estimated from the relative peak heights of the G and A peaks at methylated CpG sequences after normalizing the A peak for the average peak height along the entire sequence and substracting the background for the G peak.

For the restriction enzyme analysis of PCR products from bisulfite-treated DNA (Xiong and Laird, 1997), 50 ng of the PCR products were digested with 10 units of TaqI (New England Biolabs; Beverly, Mass.) according to conditions specified by the manufacturer of the enzyme and analyzed on a 2.2% TBE agarose gel.

RT-PCR analysis. Total RNA from cells or tissues was isolated by the guanidinium isothiocyanate method (RNAgents: Promega). RT-PCR was essentially performed as described above. Briefly, 100 ng of RNA was pre-associated with of a lower primer from exon 4. After the RT reaction, half of the samples was pipetted into tubes containing PCR master mix and an upper primer from exon 2αβ and the remaining half was added into tubes containing PCR mix and an upper primer from exon 2γ. These conditions selectively amplify transcripts RASSF1A and RASSF1C, respectively. PCR conditions were 95° C. for 30 sec, 60° C. for 30 sec and 74° C. for 1 min, for 20 cycles for the RASSF1 gene and 15 cycles for the GAPD gene. These cycle numbers were chosen because they were in the exponential range of product amplification. PCR products were separated on 2% TBE agarose gels, blotted, hybridized with a labeled probe from exon 3, and visualized by autoradiography.

Re-expression of RASSF1A. Breast cancer cell lines were treated with 5-aza-2'-deoxycytidine (5-Aza-CdR; Sigma). 2×10$^6$ cells each were grown for four days in presence of different concentrations of 5-Aza-CdR. RNA was isolated and RT-PCR was performed as described above.

Mutation screening. Exon sequences were amplified by mixing 200 ng of genomic DNA with 16 pmoles of each exon-specific primer in 100 µl reaction buffer containing 200 µM of each dNTP and Taq polymerase (Roche Diagnostics Corp.) and incubating at 95° C. for 30 sec, 60° C. for 30 sec and 74° C. for 1 min, for 35 cycles. PCR products were purified using QIAquick PCR purification kit (Qiagen), and both strands were sequenced directly without subcloning.

LOH analysis. The microsatellite markers used were D3S4615/LUCA8.1 (Wistuba et al., 2000). For PCR amplification, one of the primers was end-labeled with α-$^{32}$ATP and T4 polynucleotide kinase (New England Biolabs). PCR was carried out in a 25 µl volume containing 50 ng of genomic DNA, 12.5 pmoles of each primer, 200 µM of each dNTP and Taq DNA polymerase (Roche Diagnostics Corp.) at 95° C. for 20 sec, 54° C. for 20 sec and 74° C. for 30 sec, for 35 cycles. PCR products were separated on an 8% denaturing polyacrylamide gel and visualized by autoradiography. LOH was defined as a more than 50% reduction of intensity in one of the two alleles as compared with that seen in the corresponding normal control.

In the above examples, we have shown that the transcript of the RASSF1A gene was missing in lung cancer cell lines and that loss of expression correlated with hypermethylation of the CpG island promoter sequence of RASSF1A. To elucidate the status of RASSF1A during breast cancer pathogenesis, we analyzed the methylation pattern of five breast cancer cell lines (MCF7, MDAMB157, MDAMB231, T47D and ZR75-1). We used bisulfite sequencing of genomic DNA to determine the methylation status of the CpG island, in which RASSF1A transcription initiates. In this method, sodium bisulfite is used to convert all unmethylated cytosines to uracils, then to thymines during the subsequent PCR step. Since 5-methylcytosine remains non-reactive, all cytosines after sequence analysis represent only methylated cytosines. All guanines present after sequencing in FIG. 9 are therefore derived from methylated cytosines on the complementary strand. We analyzed 16 CpGs in a 205 bp fragment containing three Sp1 consensus binding sites and the transcription and translation initiation sites of RASSF1A. All CpG sites in these five breast cancer cell lines were completely methylated (FIGS. 9, 10). Further, we analyzed the methylation status of the RASSF1A promoter in 45 primary breast cancer samples obtained from the City of Hope Medical Center (FIG. 9). Of the 45 mammary carcinomas analyzed, 28 (=62%) were methylated in the promoter region. The methylation data are summarized in Table 1. Forty-one of these 45 cases were ductal carcinomas representing all grades of invasion. Out of two lobular carcinomas analyzed, one was methylated and one colloid carcinoma was methylated. One phyllodes cystosarcoma was not methylated. All three grade I carcinomas were completely methylated in the RASSF1A promoter region. Of the 15 grade II carcinomas analyzed, 8 (=53%) were methylated, and 9 (=60%) of the 15 grade III carcinomas were methylated. The grades of 12 breast carcinomas were unknown and 8 (=67%) of these were methylated. From the 45 tumor cases, we analyzed 40 matching normal tissue samples. Three (7.5%) of these normal samples were methylated, but at a lower degree than the corresponding tumor samples.

TABLE 1

Summary of the Methylation Analysis

| Case | Methylation |
|---|---|
| 5 breast cancer cell lines (MCF7, MDAMB157, MDAM7B231, T47D and ZR75-1) | 5 (100%) |
| 45 primary breast tumors | 28 (62%) |
| 41 ductal carcinomas | 26 (63%) |
| 2 lobular carcinomas | 1 (50%) |
| 1 colloid carcinoma | methylated |
| 1 phyllodes cystosarcoma | unmethylated |
| 3 grade I | 3 (100%) |
| 15 grade II | 8 (53%) |
| 15 grade III | 9 (60%) |
| 12 grade unknown | 8 (67%) |
| 40 matching normal tissues | 3 (7.5%) |

Figure 9A:
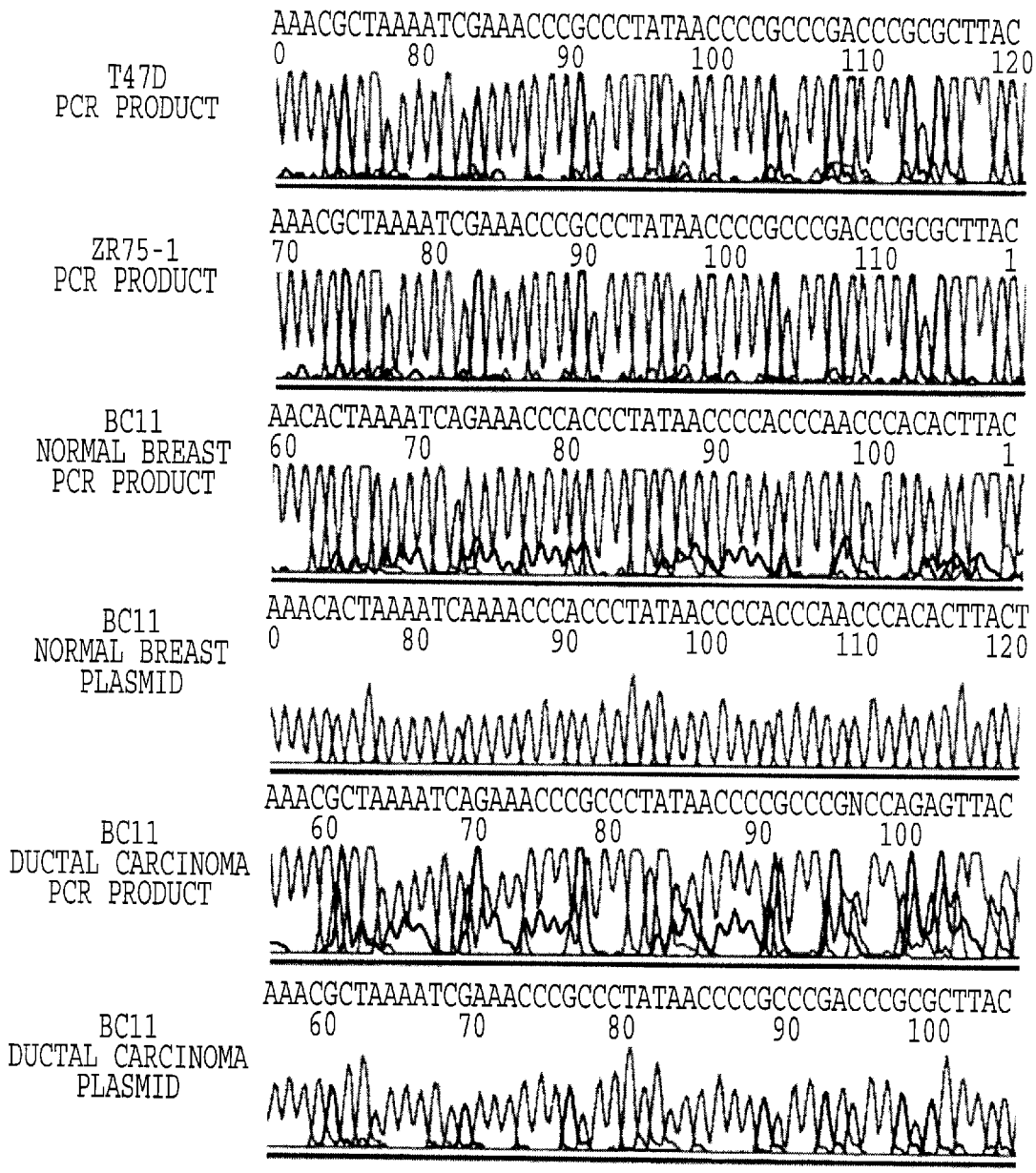
FIGS. 9A and 9B show methylation analysis of the RASSF1A gene in breast cancer. Sequences of PCR products from bisulfite-treated DNA for the CpG island spanning the RASSF1A promoter were obtained from different cancer and normal samples. Methylated cytosines appear as a G signal in the complementary strand (bold Gs). The sequence is shown before bisulfite conversion in FIG. 4A. The position of a TaqI restriction site is underlined. Two Sp1 consensus binding sites are boxed.

In FIG. 9A, a methylated ductal carcinoma (BC11) and its corresponding normal tissue is shown. The sequence of the PCR product of the carcinoma shows approximately 60% bisulfite modification-resistant cytosines at CpGs (shown as G peaks on the complementary strand). One problem with direct sequencing of PCR products from bisulfite-treated DNA is the common presence of an unspecific background signal of Gs in the sequencing scans (FIG. 9), which is also present in unmethylated samples where all Cs are converted. The ABI sequencing software unnaturally increases the G signal at non-CpG sites to somehow preserve a normal distribution of the four nucleotides. One way to eliminate this problem is to subclone the PCR fragments into plasmids. The flanking plasmid sequence has a normal distribution of all four nucleotides and therefore the data show no background in these samples (FIG. 9A). The disadvantage of the subcloning is that several subclones must be analyzed to obtain quantitative data. In the case of BC11, three of the seven analyzed subclones (43%) showed a pattern of complete methylation.

Figure 9B:
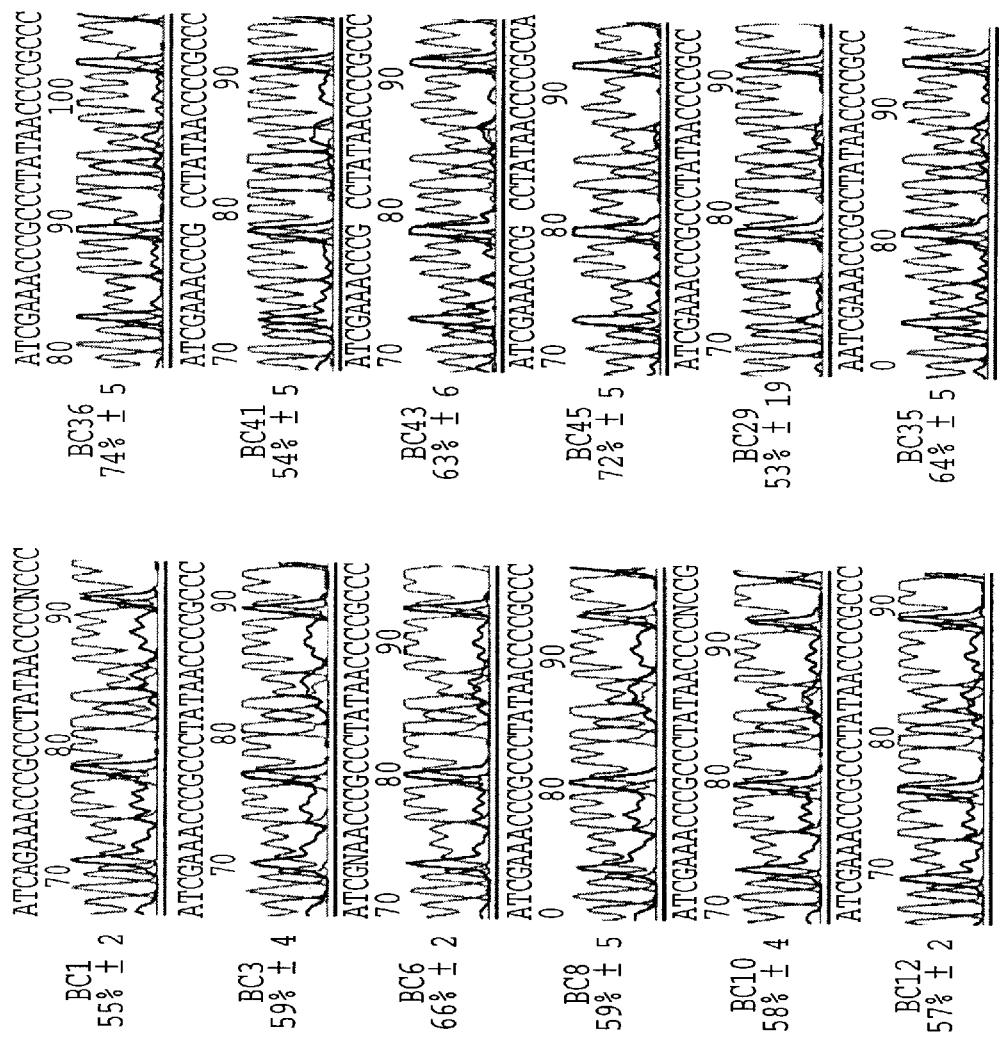
Figure 10:
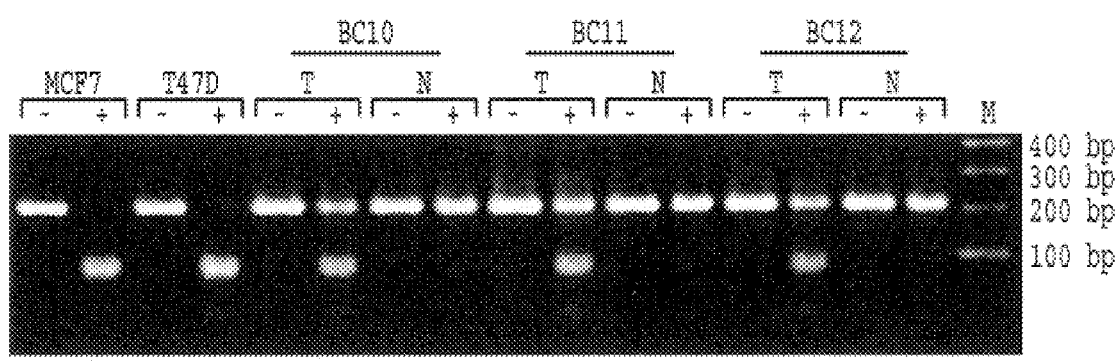
FIG. 10 shows methylation analysis of RASSF1A by restriction digestion with TaqI. PCR products from bisulfite-treated DNA obtained from different cell lines, primary tumors (T) and normal samples (N) were digested (+) or mock-digested (−) with TaqI. The sizes of molecular weight markers (M) are shown on the right in base pairs.

A larger series of sequencing data is shown in FIG. 9B. These non-microdissected breast tumors show an estimated frequency of methylated alleles of between 53% and 74%. With the exception of one CpG site in sample BC29, which showed only a low frequency of methylation, all other CpG sequences had a similarly uniform range of methylation levels of greater than 50% (FIG. 9B).

A second method to analyze the PCR fragments obtained from bisulfite-modified DNA is by further digestion with a restriction enzyme that has a CpG in its consensus sequence (Xiong and Laird, 1997). TaqI (5'TCGA-3') will cut only previously methylated DNA after bisulfite treatment and PCR. The consensus sequence will be lost in unmethylated samples. The analyzed 205 bp fragment has two TaqI sites. Restriction digestion of methylated fragments results in three bands (90, 81 and 34 bp; the two larger ones migrating together). PCR fragments from the breast cancer cell lines MCF7 and T47D showed complete methylation at these TaqI sites (FIG. 10). The restriction digest of MDAMB231, MDAMB157 and ZR75-1 also showed 100% methylation. In FIG. 10, we analyzed three primary ductal carcinomas by TaqI restriction (BC10, BC11 and BC12). The tumor samples showed approximately 50–60% methylation of the TaqI sites. The matching normal DNA samples were unmethylated. These data and several others confirm the results obtained by direct sequencing.

Figure 11:
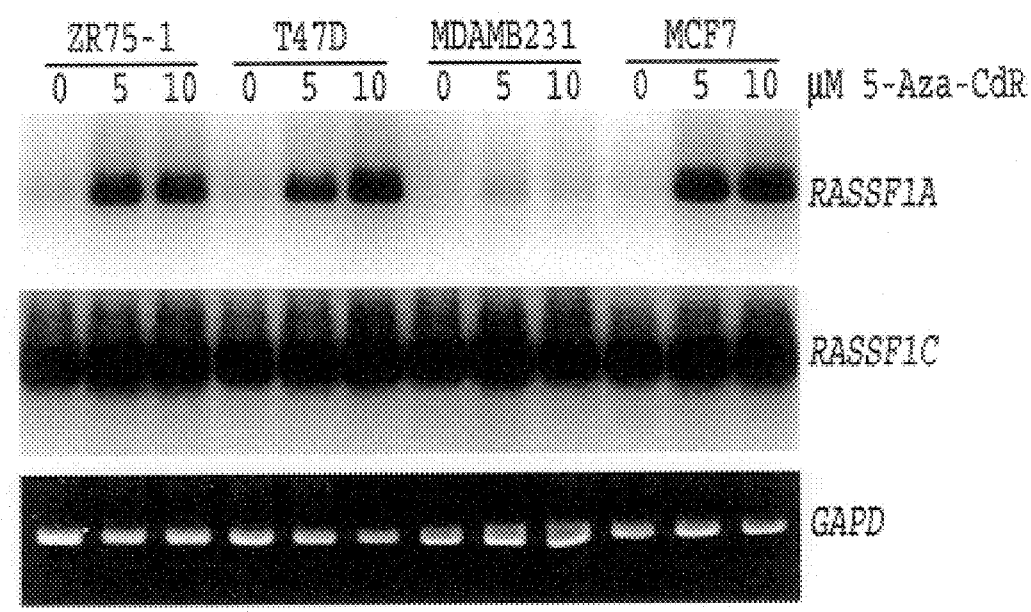
FIG. 11 shows expression and re-expression of RASSF1A by treatment with 5-aza-2'-deoxycytidine (5-Aza-CdR) in four breast cancer cell lines. The cell lines were treated for four days with the indicated concentrations of 5-Aza-CdR. RASSF1A and RASSF1C were analyzed by RT-PCR. Expression of GAPD was determined as a control for RNA integrity.

We analyzed the expression of RASSF1A in breast cancer cell lines by RT-PCR (FIG. 11). ZR75-1, T47D, MDAMB231 and MCF7 (FIG. 11), as well as MDAMB157, showed only traces of expression. At the same time, the alternative transcript RASSF1C was present at high levels in all cell lines. Epigenetic inactivation of genes by DNA methylation can be reversed by treatment with the DNA methylation inhibitor 5-aza-2'-deoxycytidine (5-Aza-CdR) (Jones and Taylor, 1980). The four cell lines were treated with this compound for four days at various concentrations. 5-Aza-CdR reactivated expression of RASSF1A in all four cell lines (FIG. 11).

Figure 12:
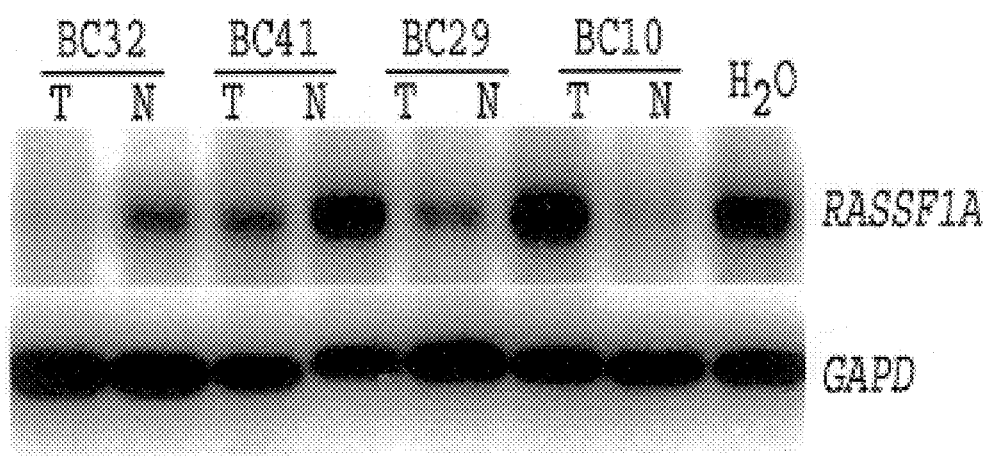
FIG. 12 shows expression of RASSF1A in primary breast cancer samples and matching normal tissue controls. RASSF1A and GAPD were analyzed by RT-PCR using PCR cycle numbers chosen to give product amplification in the exponential range.

We also performed RT-PCR on primary tumors (FIG. 12). This analysis is more difficult because normal cells are present and the RNA quality is not always very good. We were able to obtain good quality RNA from four matched samples of normal breast tissue and tumor in which the tumor DNA was methylated. In FIG. 12, we show by quantitative RT-PCR, that expression of RASSF1A is three- to ten-times lower in the tumor tissues compared to the normal matching tissues.

Mutation analysis was carried out to search for changes in the coding sequence of RASSF1A in those samples that were unmethylated. In the 17 samples analyzed, no base changes were found. A common polymorphism was identified in exon 1 [AAG(Lys21)/CAG(Gln21)].

In the previouis examples we have characterized the Ras association domain family 1A gene (RASSF1A). RASSF1A was epigentically inactivated in 40% of the analyzed primary non-small cell lung tumors and in several different cancer cell lines. In this example we demonstrate that in primary breast tumors the RASSF1A promoter is methylated at an even higher frequency (62%). The degree of methylation at CpG sites in these non-microdissected carcinomas ranged from 50 to 75% and was nearly 100% for all five analyzed breast cancer cell lines. A degree of methylation of more than 50% would suggest that either both alleles are methylated or that one allele is methylated and the other one is lost. LOH of 3p21for breast cancer was reported to be between 25 and 35% (Sato et al., 1991; Deng et al., 1994; Matsumoto et al., 1997; Driouch et al., 1998; Braga et al., 1999; Osborne et al., 2000). Using the microsatellite marker D3S4615/LUCA8.1, which is approximately 140 kb proximal to the RASSF1 gene, we found LOH in 3/19 (16%) of informative cases. Two of the samples with LOH were methylated.

Methylation and LOH may be the major loss of function pathways for the RASSF1A gene since somatic mutations appear to be rare in this gene. Interestingly, we could detect a constant methylation frequency of RASSF1A in all different grades of the mammary carcinomas. RASSF1A inactivation was already very high in grade I tumors (Table 1). Thus, methylation of RASSF1A may be an early event during breast cancer pathogenesis. We could detect some methylation in 7.5% of the samples, which were classified as normal tissue removed with tumor surgery. It will be interesting to investigate whether this methylation occurs as part of the aging process, a phenomenon which has been described for other genes (Ahuja et al., 1998).

Hypermethylation of the RASSF1A promoter appears to be the main mechanism of inactivation. Our data support the revised Knudson two-hit theory (Jones and Laird, 1999). In this new hypothesis epigenetic mechanisms of gene inactivation are included. Epigenetic silencing was shown to be a common mechanism for loss of function for several tumor suppressor genes including p16, VHL, MLH1 and also BRCA1.BRCA1 promoter methylation of sporadic breast carcinomas was at least four times less frequent compared to the hypermethylation of RASSF1A (Rice et al., 1998; Catteau et al., 1999; Esteller et al., 2000; Rice et al., 2000). The precise function of RASSF1A is still unclear and more biochemical and genetic data are needed to understand its role in tumorigenesis. In a recent study, Vos et al. have shown that RASSF1C binds RAS in a GTP-dependent manner, similar as its closest homologue, the mammalian Ras effector Nore1 (Vavvas et al., 1998). Over-expression of RASSF1C induced apoptosis. Since isoforms RASSF1A and RASSF1C share the identical RAS association domain, it is likely that RASSF1A will bind to RAS in the same manner as RASSF1C. Activated RAS proteins are usually associated with growth enhancement and transformation. However, RAS also can induce growth inhibitory effects manifested by senescence (Serrano et al., 1997), terminal differentiation (Bar-Sagi and Feramisco, 1985) or apoptosis (Downward, 1998). RASSF1 might be responsible for the RAS-dependent growth inhibition through its pro-apoptotic function (Vos et al., 2000). Loss of RASSF1 expression by methylation in human cancer may shift the balance of RAS activities towards a growth promoting effect without the necessity of RAS activating mutations.

None of the genes located within the 3p21.3 homozygous deletion region was found to be mutated in more than 5–10% of lung tumors (Lerman and Minna, 2000). This supports the assumption that the putative 3p21.3 tumor suppressor gene is inactivated by mechanisms other than mutation of the coding sequence. The high frequency of epigenetic inactivation of the RASSF1A gene in breast cancer supports its role as a putative tumor suppressor gene.

While the invention has been disclosed in this patent application by reference to the details of preferred embodiments of the invention, it is to be understood that the disclosure is intended in an illustrative rather than in a limiting sense, as it is contemplated that modifications will readily occur to those skilled in the art, within the spirit of the invention and the scope of the appended claims.

List of References

Ahrendt, S. A. et al. (1999). *J. Natl. Cancer Inst.* 91:332–339.
Ahuja, N. et al. (1998). *Cancer Res.* 58:5489–5494, 1998.
Altschul, S. F. et al. (1990). *J. Mol. Biol.* 215:403.
Altschul, S F, et al. (1997). *Nucl. Acids Res.* 25:3389–3402.
Anand, R (1992). *Techniques for the Analysis of Complex Genomes* (Academic Press).
Ausubel, F M, et al. (1992). *Current Protocols in Molecular Biology*, (John Wiley & Sons, New York, N.Y.).
Bar-Sagi, D. and Feramisco, J. R. (1985). *Cell* 42:841–848.
Bartel, P L, et al. (1993). *Cellular Interactions in Development: A Practical Approach*, Oxford University Press, pp. 153–179.
Baylin, S. B. et al. (1998). *Adv. Cancer Res.* 72:141–196.
Belinsky, S. A. et al. (1998). *Proc. Natl. Acad. Sci. U.S.A.* 95:11891–11896.
Biocomputing: Informatics and Genome Projects, Smith, D. W., ed., Academic Press, Press, NY (1993).
Blackwood, M. A. and Weber, B. L. (1998). *J. Clin. Oncol* 16:1969–1977.
Borman, S (1996). *Chemical & Engineering News*, December 9 issue, pp. 42–43.
Braga, E. et al. (1999). *FEBS Lett.* 54:215–219.
Capecchi, M R (1989). *Science* 244:1288.
Cariello, N F (1988). *Am. J. Human Genetics* 42:726–734.
Carillo, H. and Lipman, D. (1988). *SIAM J. Applied Math.* 48:1073.
Catteau, A. et al. (1999). *Oncogene.* 18:1957–1965.
Centers for Disease Control and Prevention (1997). *MMWR Mortality Wkly Rpt December 26* 46(51):1217–20.
Chee, M, et al. (1996). *Science* 274:610–614.
Chen, C. Y. et al. (1998). *J. Biol. Chem.*, 273, 16700–16709.
Chevray, P M and Nathans, D N (1992). *Proc. Natl. Acad. Sci. U.S.A* 89:5789–5793.
Chowdhury, P, et al. (1989). *Pharmacol. Biochem. Behav.* 33:591–594.
Chowdhury, P, et al. (1990). *Pancreas* 5:222–229.
Chowdhury, P, et al. (1991). *Regul. Pept.* 33:11–20.
Clark, S. J. et al. (1994). *Nucleic Acids Res.* 22:2990–2997.
Compton, J (1991). *Nature* 350:91–92.
*Computational Molecular Biology, Lesk*, A. M., ed., Oxford Univ. Press, NY (1988).
*Computer Analysis of Sequence Data*, Part I, Griffin, A. M., and Griffin, H. G., eds., Humana Press, NJ (1994).
Conner, B J, et al. (1983). *Proc. Natl. Acad. Sci. U.S.A* 80:278–282.
Conway, K. E. et al. (1996). *Cancer Res.* 60:6236–6242.
Costall, B, et al. (1991). *Neuropeptides* 19 Suppl:65–73.
Cotten, M, et al. (1990). *Proc. Natl. Acad. Sci. U.S.A* 87:4033–4037.
Crawley, J N and Corwin, R I (1994). *Peptides* 15:731–755.
Crawley, J N and Schwaber, J S (1984). *Brain Res.* 295:289–299.
Crisp, A, et al. (1999). *J. Adolesc.* 22:657–672.
Deng, G. et al. (1994). *Cancer Res.* 54:499–505.
DeRisi, J, et al. (1996). *Nat. Genet.* 14:457–460.
Deutscher, M (1990). *Meth. Enzymology* 182:83–89 (Academic Press, San Diego, Calif.).
Devereux, J et al. (1984). *Nucl. Acids Res.* 12(1):387.
Donehower, L A, et al. (1992). *Nature* 356:215.

Downward, J. (1998). *Curr. Opin. Genet. Dev.* 8:49–54.
Driouch, K. et al. (1998). *Cancer Res.* 8:2081–2086.
Editorial (1996). *Nature Genetics* 14:367–370.
Edwards, G L, et al. (1986). *Am. J. Physiol.* 251:R971–R977.
Elghanian, R, et al. (1997). *Science* 277:1078–1081.
Eng, C. et al. (2000). *Nature Genet.* 24:101–102.
Esteller, M. et al. (2000). *J. Natl. Cancer Inst.* 92:564–569.
Fahy, E, et al. (1991). *PCR Methods Appl.* 1:25–33.
Ferguson, A. T. et al. (2000). *Proc. Natl. Acad. Sci. U.S.A.* 97:6049–6054.
Fields, S and Song, O-K (1989). *Nature* 340:245–246.
Fink, H, et al. (1999). *Exp. Brain Res.* 123:77–83.
Finkelstein, J, et al. (1990). *Genomics* 7:167–172.
Fodor, SPA (1997). *Science* 277:393–395.
Ford, D. and Easton, D. F. (1995). *Br. J. Cancer.* 72:805–812.
Fu, D-J., et al. (1998). *Nat. Biotechnol.* 16:381–384.
Fujii, H. et al. (1998). *Oncogene.* 16:2159–2164.
Funakoshi, A, et al. (1994). *Biochem. Biophys. Res. Commun.* 199:482–488.
Futreal, P. A. et al. (1994). *Science.* 266:120–122.
Fuze, K, et al. (1985). *Acta Physiol Scand.* 125:437–443
Giovino G A, et al. (1995). *Epidemiol. Rev.* 17:48–65.
Girard, L. et al. (2000). *Cancer Res.* 60:4894–4906.
Glover, D (1985). *DNA Cloning*, I and II (Oxford Press).
Goding (1986). *Monoclonal Antibodies: Principles and Practice,* 2d ed. (Academic Press, NY).
Godowski, P J, et al. (1988). *Science* 241:812–816.
Graff, J. R. et al. (1995). *Cancer Res.* 55:5195–5199.
Graff, J. R. et al. (2000). *J. Biol. Chem.* 275:2727–2732,.
Grompe, M (1993). *Nature Genetics* 5:111–117.
Grompe, M, et al. (1989). *Proc. Natl. Acad. Sci. U.S.A.* 86:5855–5892.
*Guide to Huge Computers*, Martin J. Bishop, ed., Academic Press, San Diego, Calif. (1994).
Guthrie, G and Fink G R (1991). *Guide to Yeast Genetics and Molecular Biology* (Academic Press).
Hacia, J G, et al. (1996). *Nature Genetics* 14:441–447.
Harada, S, et al. (1998). *Alcholism: Clin. and Exp. Res.* 22:93S–96S.
Harlow, E and Lane, D (1988). *Antibodies. A Laboratory Manual* (Cold Spring Harbor Laboratory, Cold Spring Harbor, N.Y.).
Hasty, P K, et al. (1991). *Nature* 350:243.
Heath, A C and Martin, N G (1993). *Addictive Behaviors* 18:19–34.
Herman, J. G. and Baylin, S. B. (2000). *Curr. Top. Microbiol. Immunol.* 249:35–54.
Herman, J. G. et al. (1996). *Proc Natl Acad Sci U.S.A* 93:9821–9826
Hibi, K. et al. (1992). *Oncogene* 7:445–449.
Hung, J. et al. (1995). *JAMA* 273:558–563.
Hunter, C. P. (2000). *Cancer.* 88:1193–1202.
Huse, W D, et al. (1989). *Science* 246:1275–1281.
Ingvarsson, S. (1999). *Semin. Cancer Biol.* 9:277–288.
Innis, M A, et al. (1990). *PCR Protocols: A Guide to Methods and Applications* (Academic Press, San Diego, Calif.).
Ishiguro, H, et al. (1999). *Psychiatry Res.* 85:209–213.
Jablonski, E, et al. (1986). *Nucl. Acids Res.* 14:6115–6128.
Jensen, R T, et al. (1989). *Trends Pharmacol. Sci.* 10:418–423.
Jones, P. A. and Laird, P. W. (1999). *Nature Genet.* 21:163–167.
Jones, P. A. and Taylor, S. M. (1980). *Cell* 20:85–93.
Kanehisa, M (1984). *Nucl. Acids Res.* 12:203–213.
Kendrick, J S and Merritt, R K (1996). *Am. J. Obstet. Gynecol.* 175:528–535.
Kinszler, K W, et al. (1991). *Science* 251:1366–1370.
Klesges, R C, et al. (1999). *Ann. Behavioral Medicine* 11:134–143.
Knudson, A. G., Jr. (1971). *Proc. Natl. Acad. Sci. U.S. A.* 68:820–823.
Kohler, G and Milstein, C (1975). *Nature* 256:495–497.
Kok, K. et al. (1997). *Adv. Cancer Res.* 71:27–92.
Kraemer, F B, et al. (1993). *J. Lipid Res.* 34:663–672.
Lancaster, J. M. et al. (1996). *Nature Genet.* 13:238–240.
Landegren, U, et al. (1988). *Science* 242:229–237.
Lee, J E, et al. (1995). *Science* 268:836–844.
Lerman, M. I. and Minna, J. D. (2000). *Cancer Res.* 60:6116–6133.
Lindblad-Toh, K. et al. (2000). *Nature Biotechnol.* 18:1001–1005.
Lipshutz, R J, et al. (1995). *BioTechniques* 19:442–447.
Lockhart, D J, et al. (1996). *Nature Biotechnology* 14:1675–1680.
Maniatis, T, et al. (1982). *Molecular Cloning: A Laboratory Manual* (Cold Spring Harbor Laboratory, Cold Spring Harbor, N.Y.).
Martin, R, et al. (1990). *BioTechniques* 9:762–768.
Matsumoto, S. et al. (1997). *Genes Chromosomes Cancer.* 20:268–274.
Matthews, J A and Kricka, L J (1988). *Anal. Biochem.* 169:1.
Mayo, M. W. et al. (1997). *Science* 278:1812–1815.
Merrifield, B (1963). *J. Am. Chem. Soc.* 85:2149–2156.
Mifflin, T E (1989). *Clinical Chem.* 35:1819–1825.
Miki, Y. et al. (1999). Semin. *Cancer Biol.* 9:277–288.
Mitsudomi, T. et al. (1991). *Oncogene* 6:1353–1362.
Modrich, P (1991). *Ann. Rev. Genet.* 25:229–253.
Mombaerts, P, et al. (1992). *Cell* 68:869.
Nass, S. J. et al. (2000). *Cancer Res.* 60:4346–4348.
Naylor, S. L. et al. (1987). *Nature* 329:451–454.
Newton, A. C. (1995). *Curr. Biol.* 5:973–976.
Newton, C R, et al. (1989). *Nucl. Acids Res.* 17:2503–2516.
Nguyen, Q, et al. (1992). *BioTechniques* 13:116–123.
Novack, D F, et al. (1986). *Proc. Natl. Acad. Sci. U.S.A* 83:586–590.
Orita, M, et al. (1989). *Proc. Natl Acad. Sci. U.S.A* 86:2766–2770.
Osborne, R. J. and Hamshere, M. G. A. (2000). *Cancer Res.* 60:3706–3712.
Ottaviano, Y. L. et al. (1994). *Cancer Res.* 54:2552–2555.
Palmisano, W. A. et al. (2000). *Cancer Res.* 60:5954–5958.
Peto, J. et al. (1999). *J. Natl. Cancer Inst.* 91:943–949.
Philpott, K L, et al. (1992). *Science* 256:1448.
Ponting, C. P. and Benjamin, D. R. (1996). *Trends Biochem. Sci.* 21:422–425.
Raman, V. et al. (2000). *Nature.* 405:974–978.
Rasmussen K, et al. (1996). *Neuro Report* 10:1050–1052.
Razin, A. and Riggs, A. D. (1980). *Science* 210:604–610.
*Remington's Pharmaceutical Sciences,* 18th Ed. (1990, Mack Publishing Co., Easton, Pa.).
Rice, J. C. et al. (1998). *Oncogene.* 17:1807–1812.
Rice, J. C. et al. (2000). *Carcinogenesis.* 21:1761–1765.
Rigby, P W J, et al. (1977). *J. Mol. Biol.* 113:237–251.
Ruano, G and Kidd, K K (1989). *Nucl. Acids Res.* 17:8392.
Sambrook, J, et al. (1989). *Molecular Cloning: A Laboratory Manual,* 2nd Ed. (Cold Spring Harbor Laboratory, Cold Spring Harbor, N.Y.).
Sato, T. et al. (1991). *Cancer Res.* 51:5794–5799.
Scharf, S J, et al. (1986). *Science* 233:1076–1078.
Scopes, R (1982). *Protein Purification: Principles and Practice,* (Springer-Verlag, N.Y.).

Sekido, Y. et al. (1998). *Oncogene* 16:3151–3157.
*Sequence Analysis in Molecular Biology*, von Heinje, G., Academic Press (1987).
*Sequence Analysis Primer*, Gribskov, M. and Devereux, J., eds., M Stockton Press, NY (1991)
Serrano, M. et al. (1997). *Cell* 88:593–602.
Shao, J. et al. (2000). *J. Biol. Chem.* 275:22916–22924.
Sheffield, V C, et al. (1989). *Proc. Natl. Acad. Sci. U.S.A* 86:232–236.
Shenk, T E, et al. (1975). *Proc. Natl. Acad. Sci. U.S.A* 72:989–993.
Shinkai, Y, et al. (1992). *Cell* 68:855.
Shoemaker, D D, et al. (1996). *Nature Genetics* 14:450–456.
Simpson, J. F. and Page, D. L. (1994). *Am. J. Clin. Pathol.* 102:S3–S8.
Smith, G P and Gibbs, J (1994). *Ann. N.Y. Acad. Sci.* 713:236–41.
Snouwaert, J N, et al. (1992). *Science* 257:1083.
Sorensin, G, and Pechacek, T F (1987). *J. Behav. Med.* 10:129–137.
Spargo, C A, et al. (1996). *Mol. Cell. Probes* 10:247–256.
Steer, R A, et al. (1994). *J. Pers. Assess.* 62:525–536.
Szabo, P. E. and Mann, J. R. (1995). *Genes Dev.* 9:1857–1868.
Teng, D. H. et al. (1996). *Nature Genet.* 13:241–244.
Törmänen, V. T. and Pfeifer, G. P. (1992). *Oncogene* 7:1729–1736.
True, W R, et al. (1997). *Addiction* 92:1277–1287.
Valancius, V and Smithies, O (1991). *Mol. Cell Biol.* 11:1402.
Vavvas, D. et al. (1998). *J. Biol. Chem.* 273:5439–5442.
Vos, M. D. et al. (2000). *J. Biol. Chem.* 275:35669–35672.
Wagner, S. N. et al. (1993). *Virchows Arch. B* 63:325–329.
Walker, G T, et al. (1992). *Nucl. Acids Res.* 20:1691–1696.
Wang, Z, et al. (1998). *Am. J. Medical Genetics* 81:228–234.
Wartell, R M, et al. (1990). *Nucl. Acids Res.* 18:2699–2705.
Wei, M.-H. et al. (1996). *Cancer Res.* 56:1487–1492.
Wetmur, J G and Davidson, N (1968). *J. Mol. Biol.* 31:349–370.
Whang-Peng, J. et al. (1982). *Science* 215:181–182.
White, M B, et al. (1992). *Genomics* 12:301–306.
White, R and Lalouel J M (1988). *Annu. Rev. Genet.* 22:259–279.
Widschwendter, M. et al. (2000). *J. Natl. Cancer Inst.* 92:826–832.
Winders, S E and Grunberg, N E (1989). *Ann. Behavioral Medicine* 11:125–133.
Wistuba, I. I. et al. (1999). *Oncogene* 18:643–650.
Wistuba, I. I. et al. (2000). *Cancer Res.*, 60, 1949–1960.
Wu, D Y and Wallace, R B (1989). *Genomics* 4:560–569.
Xiong, Z. and Laird, P. W. (1997). *Nucleic Acids Res* 25:2532–2534.
Yoshida, T. et al. (2000). *Carcinogenesis.* 21:2193–2201.

Patents and Patent Applications
European Patent Application Publication No. 0332435.
EPO Publication No. 225,807.
EP 425,731A.
WO 90/07936.
WO 92/19195.
WO 94/25503.
WO 95/01203.
WO 95/05452.
WO 96/02286.
WO 96/02646.
WO 96/11698.
WO 96/40871.
WO 96/40959.
WO 97/12635.
U.S. Pat. No. 3,817,837.
U.S. Pat. No. 3,850,752.
U.S. Pat. No. 3,939,350.
U.S. Pat. No. 3,996,345.
U.S. Pat. No. 4,275,149.
U.S. Pat. No. 4,277,437.
U.S. Pat. No. 4,366,241.
U.S. Pat. No. 4,376,110.
U.S. Pat. No. 4,486,530.
U.S. Pat. No. 4,683,195.
U.S. Pat. No. 4,683,202.
U.S. Pat. No. 4,816,567.
U.S. Pat. No. 4,868,105.
U.S. Pat. No. 5,270,184.
U.S. Pat. No. 5,409,818.
U.S. Pat. No. 5,455,166.
U.S. Pat. No. 5,550,050.
U.S. Pat. No. 5,691,198.
U.S. Pat. No. 5,800,998.
U.S. Pat. No. 5,837,492.
U.S. Pat. No. 5,891,628.
U.S. Pat. No. 6,017,524.

---

What is claimed is:

1. A method for detecting expression of a gene associated with cancer in a human, comprising analyzing a sample from said human for expression of a RASSF1.A isoform of a RASSF1 gene, or for methylation of a RASSF1 gene, wherein methylation of said gene, or non-expression of said isoform is associated with cancer.

2. The method of claim 1, wherein methylation of the RASSF1 gene is detected.

3. A method for determining whether a human subject has or is at risk for developing cancer comprising the steps of:
   a) obtaining a sample from a subject, said sample comprising nucleic acid molecules containing an RASSF1 gene, wherein a transcript of said RASSF1 gene is of an RASSF1.A isoform; and
   b) detecting (i) the methylation of the RASSF1 gene, (ii) non-expression of the RASSF1.A isoform gene, or (iii) the presence or absence in the gene of said subject a genetic polymorphism selected from the group consisting of
      1) a DNA molecule comprising the nucleotide sequence set forth in SEQ ID NO:1 having GAC (Asp129) substituted by GAG (Glu129);
      2) a DNA molecule comprising the nucleotide sequence set forth in SEQ ID NO:1 having ATT (Ile135) substituted by ACT (Thr135);
      3) a DNA molecule comprising the nucleotide sequence set forth in SEQ ID NO:1 having CGG (Arg257) substituted by CAG (Gln257);
      4) a DNA molecule comprising the nucleotide sequence set forth in SEQ ID NO:1 having GCC (Ala336) substituted by ACC (Thr336);
      wherein (i) the methylation of the gene, (ii) non-expression of the isoform, or (iii) the presence of said genetic polymorphism identifies a subject that has or is at risk for developing cancer.

4. The method of claim 3, wherein methylation of the RASSF1 gene is detected.

5. The method of claim 3, wherein said genetic polymorphism is detected.

6. The method of claim 2, wherein methylation of the promoter is detected.

7. The method of claim 4, wherein methylation of the promoter is detected.

8. A method for determining whether a human subject has or is at risk for developing cancer comprising detecting the presence or absence of an RNA transcript consisting of nucleotides 39-1058 of SEQ ID NO:1 in which U is substituted for T, wherein the absence of said transcript identifies a subject that has or is at risk for developing cancer.

* * * * *

UNITED STATES PATENT AND TRADEMARK OFFICE
CERTIFICATE OF CORRECTION

PATENT NO. : 6,596,488 B2
DATED : July 22, 2003
INVENTOR(S) : Pfeifer et al.

It is certified that error appears in the above-identified patent and that said Letters Patent is hereby corrected as shown below:

<u>Column 41,</u>
Line 46, "MDAM7B231" should read -- MDAMB231 --

Signed and Sealed this

Twenty-fifth Day of May, 2004

JON W. DUDAS
*Acting Director of the United States Patent and Trademark Office*

SEQUENCE LISTING

```
<160> NUMBER OF SEQ ID NOS: 19

<210> SEQ ID NO 1
<211> LENGTH: 1873
<212> TYPE: DNA
<213> ORGANISM: Homo sapiens
<220> FEATURE:
<221> NAME/KEY: CDS
<222> LOCATION: (39)..(1058)

<400> SEQUENCE: 1
agcgcccaaa gccagcgaag cacgggccca accgggcc atg tcg ggg gag cct gag      56
                                          Met Ser Gly Glu Pro Glu
                                          1               5 ctc att gag ctg cgg gag ctg gca ccc gct ggg cgc gct ggg aag ggc      104
Leu Ile Glu Leu Arg Glu Leu Ala Pro Ala Gly Arg Ala Gly Lys Gly
         10                  15                  20
```

```
cgc acc cgg ctg gag cgt gcc aac gcg ctg cgc atc gcg cgg ggc acc      152
Arg Thr Arg Leu Glu Arg Ala Asn Ala Leu Arg Ile Ala Arg Gly Thr
        25                  30                  35 gcg tgc aac ccc aca cgg cag ctg gtc cct ggc gtg ggc cac cgc ttc      200
Ala Cys Asn Pro Thr Arg Gln Leu Val Pro Gly Val Gly His Arg Phe
    40                  45                  50 cag ccc gcg ggg ccc gcc acg cac acg tgg tgc gac ctc tgt ggc gac      248
Gln Pro Ala Gly Pro Ala Thr His Thr Trp Cys Asp Leu Cys Gly Asp
55                  60                  65                  70 ttc atc tgg ggc gtc gtg cgc aaa ggc ctg cag tgc gcg cat tgc aag      296
Phe Ile Trp Gly Val Val Arg Lys Gly Leu Gln Cys Ala His Cys Lys
                75                  80                  85 ttc acc tgc cac tac cgc tgc cgc gcg ctc gtc tgc ctg gac tgt tgc      344
Phe Thr Cys His Tyr Arg Cys Arg Ala Leu Val Cys Leu Asp Cys Cys
            90                  95                 100 ggg ccc cgg gac ctg ggc tgg gaa ccc gcg gtg gag cgg gac acg aac      392
Gly Pro Arg Asp Leu Gly Trp Glu Pro Ala Val Glu Arg Asp Thr Asn
        105                 110                 115 gtg gac gag cct gtg gag tgg gag aca cct gac ctt tct caa gct gag      440
Val Asp Glu Pro Val Glu Trp Glu Thr Pro Asp Leu Ser Gln Ala Glu
    120                 125                 130 att gag cag aag atc aag gag tac aat gcc cag atc aac agc aac ctc      488
Ile Glu Gln Lys Ile Lys Glu Tyr Asn Ala Gln Ile Asn Ser Asn Leu
135                 140                 145                 150 ttc atg agc ttg aac aag gac ggt tct tac aca ggc ttc atc aag gtt      536
Phe Met Ser Leu Asn Lys Asp Gly Ser Tyr Thr Gly Phe Ile Lys Val
                155                 160                 165 cag ctg aag ctg gtg cgc cct gtc tct gtg ccc tcc agc aag aag cca      584
Gln Leu Lys Leu Val Arg Pro Val Ser Val Pro Ser Ser Lys Lys Pro
            170                 175                 180 ccc tcc ttg cag gat gcc cgg cgg ggc cca gga cgg ggc aca agt gtc      632
Pro Ser Leu Gln Asp Ala Arg Arg Gly Pro Gly Arg Gly Thr Ser Val
        185                 190                 195 agg cgc cgc act tcc ttt tac ctg ccc aag gat gct gtc aag cac cta      680
Arg Arg Arg Thr Ser Phe Tyr Leu Pro Lys Asp Ala Val Lys His Leu
    200                 205                 210 cat gtg ctg tca cgc aca agg gca cgt gaa gtc att gag gcc ctg ctg      728
His Val Leu Ser Arg Thr Arg Ala Arg Glu Val Ile Glu Ala Leu Leu
215                 220                 225                 230 cga aag ttc ttg gtg gta gat gac ccc gcg aag ttt gca ctc ttt gag      776
Arg Lys Phe Leu Val Val Asp Asp Pro Arg Lys Phe Ala Leu Phe Glu
                235                 240                 245 cgc gct gag cgt cac ggc caa gtg tac ttg cgg aag ctg ttg gat gat      824
Arg Ala Glu Arg His Gly Gln Val Tyr Leu Arg Lys Leu Leu Asp Asp
            250                 255                 260 gag cag ccc ctg cgg ctg cgg ctc ctg gca ggg ccc agt gac aag gcc      872
Glu Gln Pro Leu Arg Leu Arg Leu Leu Ala Gly Pro Ser Asp Lys Ala
        265                 270                 275 ctg agc ttt gtc ctg aag gaa aat gac tct ggg gag gtg aac tgg gac      920
Leu Ser Phe Val Leu Lys Glu Asn Asp Ser Gly Glu Val Asn Trp Asp
    280                 285                 290 gcc ttc agc atg cct gaa cta cat aac ttc cta cgt atc ctg cag cgg      968
Ala Phe Ser Met Pro Glu Leu His Asn Phe Leu Arg Ile Leu Gln Arg
295                 300                 305                 310 gag gag gag gag cac ctc cgc cag atc ctg cag aag tac tcc tat tgc     1016
Glu Glu Glu Glu His Leu Arg Gln Ile Leu Gln Lys Tyr Ser Tyr Cys
                315                 320                 325 cgc cag aag atc caa gag gcc ctg cac gcc tgc ccc ctt ggg              1058
Arg Gln Lys Ile Gln Glu Ala Leu His Ala Cys Pro Leu Gly
```

-continued

```
                330          335          340
tgacctcttg taccccagg tggaaggcag acagcaggca gcgccaagtg cgtgccgtgt   1118
gagtgtgaca gggccagtgg ggcctgtgga atgagtgtgc atggaggccc tcctgtgctg   1178
ggggaatgag cccagagaac agcgaagtag cttgctccct gtgtccacct gtgggtgtag   1238
ccaggtatgg ctctgcaccc ctctgccctc attactgggc cttagtgggc cagggctgcc   1298
ctgagaagct gctccaggcc tgcagcagga gtggtgcaga cagaagtctc ctcaattttt   1358
gtctcagaag tgaaaatctt ggagaccctg caaacagaac agggtcatgt ttgcaggggt   1418
gacggccctc atctatgagg aaaggttttg gatcttgaat gtggtctcag gatatcctta   1478
tcagagctaa gggtgggtgc tcagaataag gcaggcattg aggaagagtc ttggtttctc   1538
tctacagtgc caactcctca cacaccctga ggtcaggag tgctggctca cagtacagca   1598
tgtgccttaa tgcttcatat gaggaggatg tccctgggcc agggtctgtg tgaatgtggg   1658
cactggccca ggttcatacc ttatttgcta atcaaagcca gggtctctcc ctcaggtgtt   1718
ttttatgaag tgcgtgaatg tatgtaatgt gtggtggcct cagctgaatg cctcctgtgg   1778
ggaaaggggt tggggtgaca gtcatcatca gggcctgggg cctgagagaa ttggctcaat   1838
aaagatttca agatccaaaa aaaaaaaaaa aaaaa                              1873
```

<210> SEQ ID NO 2
<211> LENGTH: 340
<212> TYPE: PRT
<213> ORGANISM: Homo sapiens

<400> SEQUENCE: 2

```
Met Ser Gly Glu Pro Glu Leu Ile Glu Leu Arg Glu Leu Ala Pro Ala
1               5                   10                  15

Gly Arg Ala Gly Lys Gly Arg Thr Arg Leu Glu Arg Ala Asn Ala Leu
            20                  25                  30

Arg Ile Ala Arg Gly Thr Ala Cys Asn Pro Thr Arg Gln Leu Val Pro
        35                  40                  45

Gly Arg Gly His Arg Phe Gln Pro Ala Gly Pro Ala Thr His Thr Trp
    50                  55                  60

Cys Asp Leu Cys Gly Asp Phe Ile Trp Gly Val Val Arg Lys Gly Leu
65                  70                  75                  80

Gln Cys Ala His Cys Lys Phe Thr Cys His Tyr Arg Cys Arg Ala Leu
                85                  90                  95

Val Cys Leu Asp Cys Cys Gly Pro Arg Asp Leu Gly Trp Glu Pro Ala
            100                 105                 110

Val Glu Arg Asp Thr Asn Val Asp Glu Pro Val Glu Trp Glu Thr Pro
        115                 120                 125

Asp Leu Ser Gln Ala Glu Ile Glu Gln Lys Ile Lys Glu Tyr Asn Ala
    130                 135                 140

Gln Ile Asn Ser Asn Leu Phe Met Ser Leu Asn Lys Asp Gly Ser Tyr
145                 150                 155                 160

Thr Gly Phe Ile Lys Val Gln Leu Lys Leu Val Arg Pro Val Ser Val
                165                 170                 175

Pro Ser Ser Lys Lys Pro Pro Ser Leu Gln Asp Ala Arg Arg Gly Pro
            180                 185                 190

Gly Arg Gly Thr Ser Val Arg Arg Thr Ser Phe Tyr Leu Pro Lys
        195                 200                 205

Asp Ala Val Lys His Leu His Val Leu Ser Arg Thr Arg Ala Arg Glu
    210                 215                 220
```

```
Val Ile Glu Ala Leu Leu Arg Lys Phe Leu Val Asp Asp Pro Arg
225                 230                 235                 240

Lys Phe Ala Leu Phe Glu Arg Ala Glu Arg His Gly Gln Val Tyr Leu
            245                 250                 255

Arg Lys Leu Leu Asp Asp Glu Gln Pro Leu Arg Leu Arg Leu Leu Ala
        260                 265                 270

Gly Pro Ser Asp Lys Ala Leu Ser Phe Val Leu Lys Glu Asn Asp Ser
            275                 280                 285

Gly Glu Val Asn Trp Asp Ala Phe Ser Met Pro Glu Leu His Asn Phe
        290                 295                 300

Leu Arg Ile Leu Gln Arg Glu Glu Glu His Leu Arg Gln Ile Leu
305                 310                 315                 320

Gln Lys Tyr Ser Tyr Cys Arg Gln Lys Ile Gln Glu Ala Leu His Ala
            325                 330                 335

Cys Pro Leu Gly
            340

<210> SEQ ID NO 3
<211> LENGTH: 1664
<212> TYPE: DNA
<213> ORGANISM: Homo sapiens
<220> FEATURE:
<221> NAME/KEY: CDS
<222> LOCATION: (282)..(848)

<400> SEQUENCE: 3
ggcctctctg cctgtggcct tccggccggt ttccagacgc ccaggtggcc aacattagag      60
tccgcgtagc agtgtgagat tgcaagttca cctgccacta ccgctgccgc gcgctcgtct     120
gcctggactg ttgcgggccc cgggacctgg gctgggaacc cgcggtggag cgggacacga     180
acgtggacga gcctgtggag tgggagacac ctgacctttc tcaagctgag attgagcaga     240
agatcaagga gtacaatgcc cagatcaaca gcaacctctt c atg agc ttg aac aag     296
                                              Met Ser Leu Asn Lys
                                                1               5 gac ggt tct tac aca ggc ttc atc aag gtt cag ctg aag ctg gtg cgc     344
Asp Gly Ser Tyr Thr Gly Phe Ile Lys Val Gln Leu Lys Leu Val Arg
         10                  15                  20 cct gtc tct gtg ccc tcc agc aag aag cca ccc tcc ttg cag gat gcc     392
Pro Val Ser Val Pro Ser Ser Lys Lys Pro Pro Ser Leu Gln Asp Ala
     25                  30                  35 cgg cgg ggc cca gga cgg ggc aca agt gtc agg cgc cgc act tcc ttt     440
Arg Arg Gly Pro Gly Arg Gly Thr Ser Val Arg Arg Arg Thr Ser Phe
 40                  45                  50 tac ctg ccc aag gat gct gtc aag cac ctg cat gtg ctg tca cgc aca     488
Tyr Leu Pro Lys Asp Ala Val Lys His Leu His Val Leu Ser Arg Thr
 55                  60                  65 agg gca cgt gaa gtc att gag gcc ctg ctg cga aag ttc ttg gtg gtg     536
Arg Ala Arg Glu Val Ile Glu Ala Leu Leu Arg Lys Phe Leu Val Val
 70                  75                  80                  85 gat gac ccc cgc aag ttt gca ctc ttt gag cgc gct gag cgt cac ggc     584
Asp Asp Pro Arg Lys Phe Ala Leu Phe Glu Arg Ala Glu Arg His Gly
         90                  95                 100 caa gtg tac ttg cgg aag ctg ttg gat gat gag cag ccc ctg cgg ctg     632
Gln Val Tyr Leu Arg Lys Leu Leu Asp Asp Glu Gln Pro Leu Arg Leu
        105                 110                 115 cgg ctc ctg gca ggg ccc agt gac aag gcc ctg agc ttt gtc ctg aag     680
Arg Leu Leu Ala Gly Pro Ser Asp Lys Ala Leu Ser Phe Val Leu Lys
        120                 125                 130
```

-continued

```
gaa aat gac tct ggg gag gtg aac tgg gac gcc ttc agc atg cct gaa    728
Glu Asn Asp Ser Gly Glu Val Asn Trp Asp Ala Phe Ser Met Pro Glu
    135                 140                 145 cta cat aac ttc cta cgt atc ctg cag cgg gag gag gag gag cac ctc    776
Leu His Asn Phe Leu Arg Ile Leu Gln Arg Glu Glu Glu Glu His Leu
150                 155                 160                 165 cgc cag atc ctg cag aag tac tcc tat tgc cgc cag aag atc caa gag    824
Arg Gln Ile Leu Gln Lys Tyr Ser Tyr Cys Arg Gln Lys Ile Gln Glu
                170                 175                 180 gcc ctg cac gcc tgc ccc ctt ggg tgacctcttg taccccagg tggaaggcag    878
Ala Leu His Ala Cys Pro Leu Gly
                185 acagcaggca gcgccaagtg cgtgccgtgt gagtgtgaca gggccagtgg ggcctgtgga    938
atgagtgtgc atggaggccc tcctgtgctg ggggaatgag cccagagaac agcgaagtag    998
cttgctccct gtgtccacct gtgggtgtag ccaggtatgg ctctgcaccc ctctgccctc   1058
attactgggc cttagtgggc cagggctgcc ctgagaagct gctccaggcc tgcagcagga   1118
gtggtgcaga cagaagtctc ctcaatttttt gtctcagaag tgaaaatctt ggagaccctg   1178
caaacagaac aggtcatgt ttgcagggt gacggccctc atctatgagg aaggttttg    1238
gatcttgaat gtggtctcag gatatcctta tcagagctaa gggtgggtgc tcagaataag   1298
gcaggcattg aggaagagtc ttggtttctc tctacagtgc caactcctca cacaccctga   1358
ggtcagggag tgctggctca cagtacagca tgtgccttaa tgcttcatat gaggaggatg   1418
tccctgggcc agggtctgtg tgaatgtggg cactggccca ggttcatacc ttatttgcta   1478
atcaaagcca gggtctctcc ctcaggtgtt tttttatgaa gtgcgtgaat gtatgtaatg   1538
tgtggtggcc tcagctgaat gcctcctgtg gggaaagggg ttggggtgac agtcatcatc   1598
agggcctggg gcctgagaga attggctcaa taaagatttc aagatcctca aaaaaaaaa    1658
aaaaaa                                                              1664
```

<210> SEQ ID NO 4
<211> LENGTH: 189
<212> TYPE: PRT
<213> ORGANISM: Homo sapiens

<400> SEQUENCE: 4

```
Met Ser Leu Asn Lys Asp Gly Ser Tyr Thr Gly Phe Ile Lys Val Gln
1               5                   10                  15

Leu Lys Leu Val Arg Pro Val Ser Val Pro Ser Ser Lys Lys Pro Pro
                20                  25                  30

Ser Leu Gln Asp Ala Arg Arg Gly Pro Gly Arg Gly Thr Ser Val Arg
            35                  40                  45

Arg Arg Thr Ser Phe Tyr Leu Pro Lys Asp Ala Val Lys His Leu His
    50                  55                  60

Val Leu Ser Arg Thr Arg Ala Arg Glu Val Ile Glu Ala Leu Leu Arg
65                  70                  75                  80

Lys Phe Leu Val Val Asp Asp Pro Arg Lys Phe Ala Leu Phe Glu Arg
                85                  90                  95

Ala Glu Arg His Gly Gln Val Tyr Leu Arg Lys Leu Leu Asp Asp Glu
            100                 105                 110

Gln Pro Leu Arg Leu Arg Leu Leu Ala Gly Pro Ser Asp Lys Ala Leu
        115                 120                 125

Ser Phe Val Leu Lys Glu Asn Asp Ser Gly Glu Val Asn Trp Asp Ala
130                 135                 140
```

```
Phe Ser Met Pro Glu Leu His Asn Phe Leu Arg Ile Leu Gln Arg Glu
145                 150                 155                 160

Glu Glu Glu His Leu Arg Gln Ile Leu Gln Lys Tyr Ser Tyr Cys Arg
                165                 170                 175

Gln Lys Ile Gln Glu Ala Leu His Ala Cys Pro Leu Gly
            180                 185

<210> SEQ ID NO 5
<211> LENGTH: 1692
<212> TYPE: DNA
<213> ORGANISM: Homo sapiens
<220> FEATURE:
<221> NAME/KEY: CDS
<222> LOCATION: (12)..(821)

<400> SEQUENCE: 5
cgggtacggc t atg ggc gag gcg gag gcg cct tct ttc gaa atg acc tgg      50
             Met Gly Glu Ala Glu Ala Pro Ser Phe Glu Met Thr Trp
               1               5                  10 agc agc acg acg agc agt ggc tac tgc agc caa gag gac tcg gac tcg      98
Ser Ser Thr Thr Ser Ser Gly Tyr Cys Ser Gln Glu Asp Ser Asp Ser
    15                  20                  25 gag ctc gag cag tac ttc acc gcg cga acc tcg cta gct cgc agg ccg     146
Glu Leu Glu Gln Tyr Phe Thr Ala Arg Thr Ser Leu Ala Arg Arg Pro
30                  35                  40                  45 cgc cgg gac cag gac gag cct gtg gag tgg gag aca cct gac ctt tct     194
Arg Arg Asp Gln Asp Glu Pro Val Glu Trp Glu Thr Pro Asp Leu Ser
                50                  55                  60 caa gct gag att gag cag aag atc aag gag tac aat gcc cag atc aac     242
Gln Ala Glu Ile Glu Gln Lys Ile Lys Glu Tyr Asn Ala Gln Ile Asn
            65                  70                  75 agc aac ctc ttc atg agc ttg aac aag gac ggt tct tac aca ggc ttc     290
Ser Asn Leu Phe Met Ser Leu Asn Lys Asp Gly Ser Tyr Thr Gly Phe
        80                  85                  90 atc aag gtt cag ctg aag ctg gtg cgc cct gtc tct gtg ccc tcc agc     338
Ile Lys Val Gln Leu Lys Leu Val Arg Pro Val Ser Val Pro Ser Ser
    95                  100                 105 aag aag cca ccc tcc ttg cag gat gcc cgg cgg ggc cca gga cgg ggc     386
Lys Lys Pro Pro Ser Leu Gln Asp Ala Arg Arg Gly Pro Gly Arg Gly
110                 115                 120                 125 aca agt gtc agg cgc cgc act tcc ttt tac ctg ccc aag gat gct gtc     434
Thr Ser Val Arg Arg Arg Thr Ser Phe Tyr Leu Pro Lys Asp Ala Val
                130                 135                 140 aag cac ctg cat gtg ctg tca cgc aca agg gca cgt gaa gtc att gag     482
Lys His Leu His Val Leu Ser Arg Thr Arg Ala Arg Glu Val Ile Glu
            145                 150                 155 gcc ctg ctg cga aag ttc ttg gtg gtg gat gac ccc gcc aag ttt gca     530
Ala Leu Leu Arg Lys Phe Leu Val Val Asp Asp Pro Arg Lys Phe Ala
        160                 165                 170 ctc ttt gag cgc gct gag cgt cac ggc caa gtg tac ttg cgg aag ctg     578
Leu Phe Glu Arg Ala Glu Arg His Gly Gln Val Tyr Leu Arg Lys Leu
    175                 180                 185 ttg gat gat gag cag ccc ctg cgg ctg cgg ctc ctg gca ggg ccc agt     626
Leu Asp Asp Glu Gln Pro Leu Arg Leu Arg Leu Leu Ala Gly Pro Ser
190                 195                 200                 205 gac aag gcc ctg agc ttt gtc ctg aag gaa aat gac tct ggg gag gtg     674
Asp Lys Ala Leu Ser Phe Val Leu Lys Glu Asn Asp Ser Gly Glu Val
                210                 215                 220 aac tgg gac gcc ttc agc atg cct gaa cta cat aac ttc cta cgt atc     722
Asn Trp Asp Ala Phe Ser Met Pro Glu Leu His Asn Phe Leu Arg Ile
```

```
                           225                 230                 235
ctg cag cgg gag gag gag gag cac ctc cgc cag atc ctg cag aag tac      770
Leu Gln Arg Glu Glu Glu Glu His Leu Arg Gln Ile Leu Gln Lys Tyr
            240                 245                 250 tcc tat tgc cgc cag aag atc caa gag gcc ctg cac gcc tgc ccc ctt      818
Ser Tyr Cys Arg Gln Lys Ile Gln Glu Ala Leu His Ala Cys Pro Leu
        255                 260                 265 ggg tgacctcttg taccccagg tggaaggcag acagcaggca gcgccaagtg            871
Gly
270 cgtgccgtgt gagtgtgaca gggccagtgg ggcctgtgga atgagtgtgc atggaggccc    931 tcctgtgctg ggggaatgag cccagagaac agcgaagtag cttgctccct gtgtccacct    991 gtgggtgtag ccaggtatgg ctctgcaccc ctctgccctc attactgggc cttagtgggc   1051 cagggctgcc ctgagaagct gctccaggcc tgcagcagga gtggtgcaga cagaagtctc   1111 ctcaattttt gtctcagaag tgaaaatctt ggagaccctg caaacagaac agggtcatgt   1171 ttgcagggt gacggccctc atctatgagg aaaggttttg gatcttgaat gtggtctcag    1231 gatatcctta tcagagctaa gggtgggtgc tcagaataag gcaggcattg aggaagagtc   1291 ttggtttctc tctacagtgc caactcctca cacaccctga ggtcagggag tgctggctca   1351 cagtacagca tgtgccttaa tgcttcatat gaggaggatg tccctgggcc agggtctgtg   1411 tgaatgtggg cactggccca ggttcatacc ttattgctaa tcaaagccag ggtctctccc   1471 tcaggtgttt tttatgaagt gcgtgaatgt atgtaatgtg tggtggcctc agctgaatgc   1531 ctcctgtggg gaaggggtt ggggtgacag tcatcatcag ggcctgggc ctgagagaat     1591 tggctcaata aagatttcaa gatccaaaaa aaaaaaaaa aaaaaaaaa aaaaaaaaa      1651 aaaaaaaaa aaaaaaaaa aaaaaaaaa aaaaaaaaa a                           1692

<210> SEQ ID NO 6
<211> LENGTH: 270
<212> TYPE: PRT
<213> ORGANISM: Homo sapiens

<400> SEQUENCE: 6

Met Gly Glu Ala Glu Ala Pro Ser Phe Glu Met Thr Trp Ser Ser Thr
1               5                   10                  15

Thr Ser Ser Gly Tyr Cys Ser Gln Glu Asp Ser Asp Ser Glu Leu Glu
            20                  25                  30

Gln Tyr Phe Thr Ala Arg Thr Ser Leu Ala Arg Arg Pro Arg Arg Asp
        35                  40                  45

Gln Asp Glu Pro Val Glu Trp Glu Thr Pro Asp Leu Ser Gln Ala Glu
    50                  55                  60

Ile Glu Gln Lys Ile Lys Glu Tyr Asn Ala Gln Ile Asn Ser Asn Leu
65                  70                  75                  80

Phe Met Ser Leu Asn Lys Asp Gly Ser Tyr Thr Gly Phe Ile Lys Val
                85                  90                  95

Gln Leu Lys Leu Val Arg Pro Val Ser Val Pro Ser Ser Lys Lys Pro
            100                 105                 110

Pro Ser Leu Gln Asp Ala Arg Arg Gly Pro Gly Arg Gly Thr Ser Val
        115                 120                 125

Arg Arg Arg Thr Ser Phe Tyr Leu Pro Lys Asp Ala Val Lys His Leu
    130                 135                 140

His Val Leu Ser Arg Thr Arg Ala Arg Glu Val Ile Glu Ala Leu Leu
145                 150                 155                 160
```

```
Arg Lys Phe Leu Val Val Asp Asp Pro Arg Lys Phe Ala Leu Phe Glu
                165                 170                 175

Arg Ala Glu Arg His Gly Gln Val Tyr Leu Arg Lys Leu Leu Asp Asp
            180                 185                 190

Glu Gln Pro Leu Arg Leu Arg Leu Ala Gly Pro Ser Asp Lys Ala
        195                 200                 205

Leu Ser Phe Val Leu Lys Glu Asn Asp Ser Gly Glu Val Asn Trp Asp
    210                 215                 220

Ala Phe Ser Met Pro Glu Leu His Asn Phe Leu Arg Ile Leu Gln Arg
225                 230                 235                 240

Glu Glu Glu Glu His Leu Arg Gln Ile Leu Gln Lys Tyr Ser Tyr Cys
                245                 250                 255

Arg Gln Lys Ile Gln Glu Ala Leu His Ala Cys Pro Leu Gly
                260                 265                 270

<210> SEQ ID NO 7
<211> LENGTH: 413
<212> TYPE: PRT
<213> ORGANISM: Mus musculus

<400> SEQUENCE: 7

Met Ala Ser Pro Ala Ile Gly Gln Arg Pro Tyr Pro Leu Leu Leu Asp
1               5                   10                  15

Pro Glu Pro Pro Arg Tyr Leu Gln Ser Leu Gly Gly Thr Glu Pro Pro
            20                  25                  30

Pro Pro Ala Arg Pro Arg Arg Cys Ile Pro Thr Ala Leu Ile Pro Ala
        35                  40                  45

Ala Gly Ala Ser Glu Asp Arg Gly Gly Arg Ser Gly Arg Arg Asp
    50                  55                  60

Pro Glu Pro Thr Pro Arg Asp Cys Arg His Ala Arg Pro Val Arg Pro
65                  70                  75                  80

Gly Leu Gln Pro Arg Leu Arg Leu Arg Pro Gly Ser His Arg Pro Arg
                85                  90                  95

Asp Val Arg Ser Ile Phe Glu Gln Pro Gln Asp Pro Arg Val Leu Ala
                100                 105                 110

Glu Arg Gly Glu Gly His Arg Phe Val Glu Leu Ala Leu Arg Gly Gly
            115                 120                 125

Pro Gly Trp Cys Asp Leu Cys Gly Arg Glu Val Leu Arg Gln Ala Leu
    130                 135                 140

Arg Cys Ala Asn Cys Lys Phe Thr Cys His Ser Glu Cys Arg Ser Leu
145                 150                 155                 160

Ile Gln Leu Asp Cys Arg Gln Lys Gly Gly Pro Ala Leu Asp Arg Arg
                165                 170                 175

Ser Pro Gly Ser Thr Leu Thr Pro Thr Leu Asn Gln Asn Val Cys Lys
            180                 185                 190

Ala Val Glu Glu Thr Gln His Pro Pro Thr Ile Gln Glu Ile Lys Gln
        195                 200                 205

Lys Ile Asp Ser Tyr Asn Ser Arg Glu Lys His Cys Leu Gly Met Lys
    210                 215                 220

Leu Ser Glu Asp Gly Thr Tyr Thr Gly Phe Ile Lys Val His Leu Lys
225                 230                 235                 240

Leu Arg Arg Pro Val Thr Val Pro Ala Gly Ser Gly Pro Ser Pro Ser
                245                 250                 255

Met Asp Ala Ile Lys Glu Val Asn Pro Ala Ala Thr Thr Asp Lys Arg
```

-continued

```
                        260                     265                     270
Thr Ser Phe Tyr Leu Pro Leu Asp Ala Ile Lys Gln Leu His Ile Ser
            275                     280                     285
Ser Thr Thr Thr Val Ser Glu Val Ile Gln Gly Leu Leu Lys Lys Phe
        290                     295                     300
Met Val Asp Asn Pro Gln Lys Phe Ala Leu Phe Lys Arg Ile His
305                     310                     315                     320
Lys Asp Gly Gln Val Leu Phe Gln Lys Leu Ser Ile Ala Asp Tyr Pro
                    325                     330                     335
Leu Tyr Leu Arg Leu Leu Ala Gly Pro Asp Thr Asp Val Leu Ser Phe
                340                     345                     350
Val Leu Lys Glu Asn Glu Thr Gly Glu Val Glu Trp Asp Ala Phe Ser
            355                     360                     365
Ile Pro Glu Leu Gln Asn Phe Leu Thr Ile Leu Glu Lys Glu Gln
    370                     375                     380
Asp Lys Ile His Gln Leu Gln Lys Lys Tyr Asn Lys Phe Arg Gln Lys
385                     390                     395                     400
Leu Glu Glu Ala Leu Arg Glu Ser Gln Gly Lys Pro Gly
                405                     410

<210> SEQ ID NO 8
<211> LENGTH: 413
<212> TYPE: PRT
<213> ORGANISM: Rattus norvegicus

<400> SEQUENCE: 8

Met Ala Ser Pro Ala Ile Gly Gln Arg Pro Tyr Pro Leu Leu Leu Asp
1               5                   10                  15
Pro Glu Pro Pro Arg Tyr Leu Gln Ser Leu Gly Gly Thr Glu Pro Pro
                20                  25                  30
Pro Pro Ala Arg Pro Arg Cys Ile Pro Thr Ala Leu Ile Ser Ala
            35                  40                  45
Ser Gly Ala Ser Glu Gly Arg Gly Ser Arg Arg Asn Ala Arg Gly Asp
        50                  55                  60
Pro Glu Pro Thr Pro Arg Asp Cys Arg His Ala Arg Pro Val Arg Pro
65                  70                  75                  80
Gly Leu Gln Gln Arg Leu Arg Arg Pro Gly Ser His Arg Pro Arg
                    85                  90                  95
Asp Val Arg Ser Ile Phe Glu Gln Pro Gln Asp Pro Arg Val Leu Ala
                100                     105                     110
Glu Arg Gly Glu Gly His Arg Phe Ala Glu Leu Ala Leu Arg Gly Gly
            115                     120                     125
Pro Gly Trp Cys Asp Leu Cys Gly Arg Glu Val Leu Arg Gln Ala Leu
        130                     135                     140
Arg Cys Ala Asn Cys Lys Phe Thr Cys His Pro Glu Cys Arg Ser Leu
145                     150                     155                     160
Ile Gln Leu Asp Cys Arg Gln Lys Glu Gly Pro Ala Leu Asp Arg Gln
                    165                     170                     175
Ser Pro Glu Ser Thr Leu Thr Pro Thr Phe Asn Lys Asn Val Cys Lys
                180                     185                     190
Ala Val Glu Glu Thr Gln His Pro Pro Thr Ile Gln Glu Ile Lys Gln
            195                     200                     205
Lys Ile Asp Ser Tyr Asn Ser Arg Glu Lys His Cys Leu Gly Met Lys
        210                     215                     220
```

```
Leu Ser Glu Asp Gly Thr Tyr Thr Gly Phe Ile Lys Val His Leu Lys
225                 230                 235                 240

Leu Arg Arg Pro Val Thr Val Pro Ala Gly Ile Arg Pro Gln Ser Ile
            245                 250                 255

Tyr Asp Ala Ile Lys Glu Val Asn Pro Ala Thr Thr Asp Lys Arg
            260                 265                 270

Thr Ser Phe Tyr Leu Pro Leu Asp Ala Ile Lys Gln Leu His Ile Ser
            275                 280                 285

Ser Ser Thr Thr Val Ser Glu Val Ile Gln Gly Leu Leu Lys Lys Phe
            290                 295                 300

Met Val Val Asp Asn Pro Gln Lys Phe Ala Leu Phe Lys Arg Ile His
305                 310                 315                 320

Lys Asp Gly Gln Val Leu Phe Gln Lys Leu Ser Ile Ala Asp Cys Pro
                325                 330                 335

Leu Tyr Leu Arg Leu Leu Ala Gly Pro Asp Thr Asp Val Leu Ser Phe
            340                 345                 350

Val Leu Lys Glu Asn Glu Thr Gly Asp Val Glu Trp Asp Ala Phe Ser
            355                 360                 365

Ile Pro Glu Leu Gln Asn Phe Leu Thr Ile Leu Glu Lys Glu Glu Gln
370                 375                 380

Asp Lys Ile His Gln Leu Gln Lys Lys Tyr Asn Lys Phe Arg Gln Lys
385                 390                 395                 400

Leu Glu Glu Ala Leu Arg Glu Ser Gln Gly Lys Pro Gly
                405                 410

<210> SEQ ID NO 9
<211> LENGTH: 205
<212> TYPE: DNA
<213> ORGANISM: pcr product

<400> SEQUENCE: 9
ccccacagtc cctgcaccca ggtttccatt gcgcggctct cctcagctcc ttcccgccgc    60
ccagtctgga tcctggggga ggcgctgaag tcggggcccg ccctgtggcc ccgcccggcc   120
cgcgcttgct agcgcccaaa gccagcgaag cacgggccca accgggccat gtcgggggag   180
cctgagctca ttgagctgcg ggagc                                        205

<210> SEQ ID NO 10
<211> LENGTH: 26
<212> TYPE: DNA
<213> ORGANISM: oligonuleotide primer

<400> SEQUENCE: 10
gatgaagcct gtgtaagaac cgtcct                                        26

<210> SEQ ID NO 11
<211> LENGTH: 25
<212> TYPE: DNA
<213> ORGANISM: oligonucleotide primer

<400> SEQUENCE: 11
cagattgcaa gttcacctgc cacta                                         25

<210> SEQ ID NO 12
<211> LENGTH: 27
<212> TYPE: DNA
<213> ORGANISM: oligonucleotide primer

<400> SEQUENCE: 12
```

```
cggaggcgcc ttctttcgaa atgacct                                    27

<210> SEQ ID NO 13
<211> LENGTH: 31
<212> TYPE: DNA
<213> ORGANISM: oligonucleotide primer

<400> SEQUENCE: 13
gttttggtag tttaatgagt ttaggttttt t                               31

<210> SEQ ID NO 14
<211> LENGTH: 31
<212> TYPE: DNA
<213> ORGANISM: oligonucleotide primer

<400> SEQUENCE: 14
accctcttcc tctaacacaa taaaactaac c                               31

<210> SEQ ID NO 15
<211> LENGTH: 23
<212> TYPE: DNA
<213> ORGANISM: oligonucleotide primer

<400> SEQUENCE: 15
ccccacaatc cctacaccca aat                                        23

<210> SEQ ID NO 16
<211> LENGTH: 24
<212> TYPE: DNA
<213> ORGANISM: oligonucleotide primer

<400> SEQUENCE: 16 gtttttgtg gtaggtgggg tttg                                        24

<210> SEQ ID NO 17
<211> LENGTH: 30
<212> TYPE: DNA
<213> ORGANISM: oligonucleotide primer

<400> SEQUENCE: 17
aatccraatc ctcttaacta caataaccac                                 30

<210> SEQ ID NO 18
<211> LENGTH: 23
<212> TYPE: DNA
<213> ORGANISM: oligonucleotide primer

<400> SEQUENCE: 18
ggtggggttt gtgagtggag ttt                                        23

<210> SEQ ID NO 19
<211> LENGTH: 30
<212> TYPE: DNA
<213> ORGANISM: oligonucleotide primer

<400> SEQUENCE: 19
actactcrtc rtactactcc aaatcatttc                                 30
```